US012767954B2

(12) United States Patent
Lee

(10) Patent No.: US 12,767,954 B2
(45) Date of Patent: Oct. 20, 2026

(54) COMPOSITIONS AND METHODS FOR ALTERING STEM LENGTH IN SOLANACEAE

(71) Applicant: UNIVERSITY OF FLORIDA RESEARCH FOUNDATION, INCORPORATED, Gainesville, FL (US)

(72) Inventor: Tong Geon Lee, Lithia, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 412 days.

(21) Appl. No.: 18/260,161

(22) PCT Filed: Jan. 5, 2022

(86) PCT No.: PCT/US2022/070033
§ 371 (c)(1),
(2) Date: Jun. 30, 2023

(87) PCT Pub. No.: WO2022/150811
PCT Pub. Date: Jul. 14, 2022

(65) Prior Publication Data

US 2024/0084320 A1 Mar. 14, 2024

Related U.S. Application Data

(60) Provisional application No. 63/135,048, filed on Jan. 8, 2021.

(51) Int. Cl.

| | |
|---|---|
| ***C12N 9/22*** | (2006.01) |
| ***A01H 6/82*** | (2018.01) |
| ***C12N 15/82*** | (2006.01) |

(52) U.S. Cl.
CPC ......... *C12N 15/8262* (2013.01); *A01H 6/825* (2018.05); *C12N 9/22* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,217,863 | A | 6/1993 | Cotton et al. |
| 5,468,613 | A | 11/1995 | Erlich et al. |
| 5,595,890 | A | 1/1997 | Newton et al. |
| 5,616,464 | A | 4/1997 | Albagli et al. |
| 5,762,876 | A | 6/1998 | Lincoln et al. |
| 5,800,944 | A | 9/1998 | Blonsky et al. |
| 5,876,930 | A | 3/1999 | Livak et al. |
| 5,945,283 | A | 8/1999 | Kwok et al. |
| 6,004,744 | A | 12/1999 | Goelet et al. |
| 6,013,431 | A | 1/2000 | Söderlund et al. |
| 6,030,787 | A | 2/2000 | Livak et al. |
| 6,090,558 | A | 7/2000 | Butler et al. |
| 6,503,710 | B2 | 1/2003 | Gut et al. |
| 6,613,509 | B1 | 9/2003 | Chen |
| 6,799,122 | B2 | 9/2004 | Benson |
| 6,913,879 | B1 | 7/2005 | Schena |
| 6,996,476 | B2 | 2/2006 | Najarian |
| 7,238,476 | B2 | 7/2007 | Mckeown et al. |
| 7,250,252 | B2 | 7/2007 | Katz et al. |
| 7,270,981 | B2 | 9/2007 | Armes et al. |
| 7,282,355 | B2 | 10/2007 | Shi |
| 7,297,485 | B2 | 11/2007 | Bornarth et al. |
| 7,312,039 | B2 | 12/2007 | Barany et al. |
| 2019/0374655 | A1 | 12/2019 | Kabadi et al. |
| 2020/0045901 | A1 * | 2/2020 | Lee ........................ A01H 1/045 |
| 2020/0140874 | A1 | 5/2020 | Barten et al. |

FOREIGN PATENT DOCUMENTS

WO WO-2018213538 A1 * 11/2018 ............. A01H 6/825

OTHER PUBLICATIONS

Wang et al., (GHFPF1 positively regulates shade avoidance responses via interacting with GHNF-ya3 in Cotton. Dec. 13, 2024. Industrial Crops and Products, vol. 223, p. 120193 (Year: 2024).*
Wang et al. (Studies on the Effects of fpf1 Gene on Artemisia annua Flowering Time and on the Linkage between Flowering and Artemisinin Biosynthesis. 2004 Planta Medica, vol. 70, No. 4, Apr. 2004, pp. 347-352 (Year: 2004).*
Das et al. (Variation of gene expression in plants is influenced by gene architecture and structural properties of promoters. 2019. PLoS ONE 14(3): e0212678 (Year: 2019).*
Lee et al. (Fine Mapping of the brachytic Locus on the Tomato Genome. 2018. Journal of the American Society for Horticultural Science, vol. 143, No. 4, pp. 239-247 (Year: 2018).*
(Y) Fernandez-Pozo et al. (The Sol Genomics Network (SGN)—from genotype to phenotype to breeding. 2015. Nucleic Acids Res. vol. 43 (Database issue): D1036-41 (Year: 2015).*
(Z) Guo et al. (OsFPFL4 is Involved in the Root and Flower Development by Affecting Auxin Levels and ROS Accumulation in Rice (*Oryza sativa*). 2020. Rice 13, 2 (Year: 2020).*
International Search Report and Written Opinion for International Application No. PCT/US2022/070033, dated Jun. 14, 2022, (14 pages), United States Patent and Trademark Office, US.
Gebhardt, Christiane. "The Historical Role of Species From the Solanaceae Plant Family in Genetic Research," *Theoretical and Applied Genetics*, vol. 129, No. 12, pp. 2281-2294, Dec. 2016, (Epub: Oct. 15, 2016), DOI: 10.1007/s00122-016-2804-1.

(Continued)

*Primary Examiner* — Jason Deveau Rosen
*Assistant Examiner* — Christian Jose Ordaz
(74) *Attorney, Agent, or Firm* — Alston & Bird LLP

(57) ABSTRACT

Described are CRISPR constructs and systems that can be used to generate brachytic Solanaceae plants rapidly and efficiently. Also described are methods of introducing a brachytic phenotype into a Solanaceae plant having one or more other desired traits using the described CRISPR constructs and systems to generate loss of function mutations in one or more brachytic loci in the plant.

18 Claims, 6 Drawing Sheets

Specification includes a Sequence Listing.

(56) References Cited

OTHER PUBLICATIONS

Lee, Tong Geon et al. "Fine Mapping of the Brachytic Locus on the Tomato Genome," *Journal of the American Society for Horticultural Science*, vol. 143, No. 4, Jul. 2018, pp. 239-247, DOI: 10.21273/JASHS04423-18.

Lee, Man Bo et al. "A Mutant Allele of the Flowering Promoting Factor 1 Gene at the Tomato Brachytic Locus Reduces Plant Height With High Quality Fruit," *Plant Direct*, pp. 1-16, Jun. 17, 2022, DOI: 10.1002/pld3.422.

Shattuck-Eidens, Donna M. et al. "DNA Sequence Variation Within Maize and Melon: Observations From Polymerase Chain Reaction Amplication and Direct Sequencing," *Genetics*, vol. 126, No. 1, pp. 207-217, Sep. 1, 1990, DOI: 10.1093/genetics/126.1.207.

Sjölander, Kimmer. "Phylogenomic Inference of Protein Molecular Function: Advances and Challenges," *Bioinformatics*, vol. 20, No. 2, pp. 170-179, Jan. 22, 2004, DOI: 10.1093/bioinformatics/bth021.

Xie, Kabin et al. "RNA-Guided Genome Editing in Plants Using a CRISPR-Cas System," *Molecular Plant*, vol. 6, No. 6, pp. 1975-1983, Nov. 2013. DOI: doi.10.1093/mp/sst119.

NCBI Reference Sequence No. XP_015086900, "flowering-promoting factor 1-like protein 3 [Solanum pennellii]," Jan. 28, 2019. [Retrieved from the Internet Aug. 14, 2019: <URL: https://www.ncbi.nlm.nih.gov/protein/XP_015086900>].

NCBI Reference Sequence No. XP_016557588.1, "Predicted: flowering-promoting factor 1-like protein 3 [Capsicum annuum]," May 5, 2016 [Retrieved from the Internet Aug. 15, 2019: <URL: https://www.ncbi.nlm.nih.gov/protein/XP_016557588.1>].

NCBI Reference Sequence No. XP_006342791, "Predicted: flowering-promoting factor 1-like protein 3 [Solanum tuberosum]," Jan. 5, 2016. [Retrieved from the Internet Aug. 14, 2019: <URL: https://www.ncbi.nlm.nih.gov/protein/XP_006342791>].

* cited by examiner

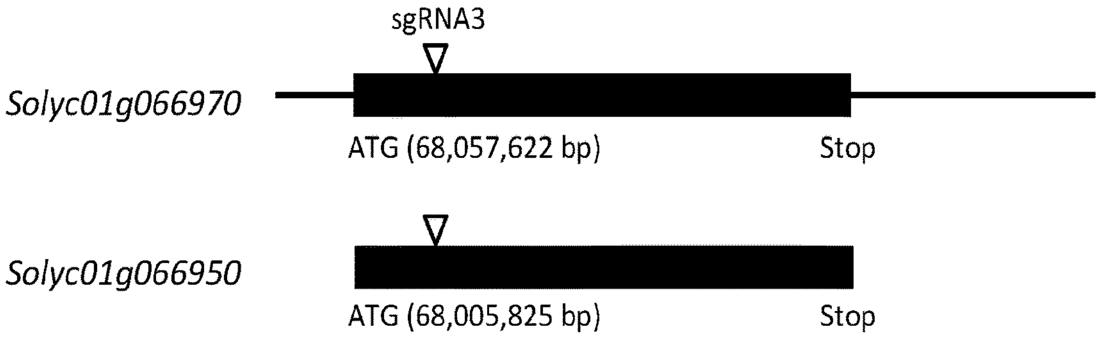

WT *Solyc01g066950* TCGCACCGTGAAAGTCACCG (SEQ ID NO: 105)
WT *Solyc01g066970* TCGCACCGTGGAAGTCACCG (SEQ ID NO: 106)

| | *Solyc01g066950* | | *Solyc01g066970* |
|---|---|---|---|
| WT | CCG**TCGCACCGTGAAAGTCA** **CCG**AGG | (52,311 BP) | CCG**TCGCA** **CCGTGGAAGTCACCG**GGG |
| br.7[CR] | CCG**TCGCACCGTGAAAGTCA** **CCG**AGG | (52,311 BP) | CCG**TCGCAACCGTGGAAGTCACCG**GGG |
| br.57.1[CR] | CCG**TCGCACCGTGA-----A** **CCG**AGG | (52,311 BP) | CCG**TCGCA** **CCGTGG-----ACCG**GGG |
| br.57.2[CR] | CCGT**CGCACCGTGAAAGTCAACCG**AGG | (52,311 BP) | CCG**TCGCA** **CCGTGG-----ACCG**GGG |
| | Δ 68,005,223 bp | | Δ 68,057,560 bp |

FIG. 5.

COMPOSITIONS AND METHODS FOR ALTERING STEM LENGTH IN SOLANACEAE

CROSS-REFERENCE TO RELATED APPLICATIONS

This application is a national phase filing of International Application No. PCT/US2022/070033, filed Jan. 5, 2022, which claims the benefit of U.S. Provisional Application No. 63/135,048, filed Jan. 8, 2021, the content of each is incorporated herein by reference.

REFERENCE TO A SEQUENCE LISTING SUBMITTED AS A TEXT FILE VIA EFS WEB

The Sequence Listing written in file 572399_T18366WO001_SeqListing.txt is 88 kilobytes in size, was created on Dec. 16, 2021, and is hereby incorporated by reference.

BACKGROUND

Tomato is the most valuable horticultural crop worldwide (Food and Agriculture Organization of the United Nations). Fresh-market and processing tomatoes are the two most commonly consumed types of tomatoes and account for more than $2.6 billion in annual farm cash receipts in the United States alone (United States Department of Agriculture Economic Research Service (USDA ERS)). Unlike processing tomatoes, which have been successfully adapted for farm machinery for nearly all aspects of production, field production of fresh-market tomatoes continues to heavily rely on manual labor (Davis and Estes, 1993 USDA ERS; Van Sickle and McAvoy 2015 USDA ERS).

Most field-grown fresh-market tomato varieties have determinate vines with upright growth. Because of their heavy large fruits (typical 110-250 g for fresh-market fruits versus <80 g for processing fruits) and the higher quality requirement of exterior standards, displacement of those plants, especially fruits laying on the soil, significantly reduces yield and quality by damages from human activities, machineries and soilborne pathogens (Adelana, B. O. 1980. Relationship between lodging, morphological characters and yield of tomato cultivars. Scientia Hort. 13:143-148). Manual practices such as staking and tying are required to sustain the current production of marketable fresh-market tomatoes.

Current compact growth habit (CGH) tomato plants, while being determinate, and having shortened internodes, a spreading characteristic (with increased side branching), and a concentrated fruit setting (producing fruits over a narrow time interval) suffer from insufficient fruit size. There presently are no commercial large-fruited, fresh-market tomatoes that show CGH. Development of fresh market tomato lines that hold fruits off the ground without the support of stakes throughout a season, adapt to high plant density per the unit area, and produce high quality fresh-market fruit of economically viable size would be of significant benefit to the tomato industry. Further, such tomato lines may also enable machine harvesting, reducing the dependence on farm labor.

Introduction of the brachytic trait into normal phenotype tomatoes resulted in tomatoes with shortened internodes. Since the introduction of brachytic (br) into fresh-market tomato breeding programs in 1980s, the locus has been shown to be the primary source of the shortened internode phenotype. It is notable that no evidence for a significant negative correlation observed between marketable fruit harvests and the br has been reported in a peer-reviewed forum. Identification of genes or mutations that results in plants with shortened stem length A reduced plant height driven by shortened stems is beneficial for improving crop yield potential. The presence of br is an important consideration in developing tomatoes intended for mechanical harvest. There is a need to breed new genes that optimize phenotypes for such mechanization into fresh-market adapted tomato cultivars.

SUMMARY

Regulation of stem length is an important target trait in plant breeding and genetics. Described are tomato brachytic loci that control stem length. Disruption of these brachytic loci result in plants having shortened internode length. Described are compositions and methods for generating plants having shortened internode length.

Described are loci responsible for the brachytic phenotype in plants of the family Solanaceae (brachytic locus). The loci are open reading frames located at Solyc01g066950, Solyc01g066970, Solyc06g005530, and Solyc12g099610 of *S. lycopersicum*. Solanaceae plants homozygous for loss of function alleles at one or more of these loci have shortened internode length. In some embodiments, Solanaceae plants heterozygous for loss of function alleles at one or more of these loci may have shortened internode length.

Described are CRISPR constructs and systems that can be used to generate brachytic Solanaceae plants rapidly and efficiently. A brachytic phenotype can be introduced into a Solanaceae plant having one or more other desired traits by using the described CRISPR constructs and systems to generate loss of function mutations in one or more brachytic loci in the desired plant. The described CRISPR constructs and systems can be used to introduce a loss of function mutation at one or more of the open reading frames located at Solyc01g066950, Solyc01g066970, Solyc06g005530, and Solyc12g099610. The described CRISPR constructs can be further combined with a CRISPR construct or system for introducing a loos of function mutation in an open reading frame located at Solyc01g066980.

In some embodiments, the CRISPR constructs are used to introduce a mutant brachytic allele into a Solanaceae plant. The modified plants is then used to introgress the brachytic allele into other genetic backgrounds. The resultant plants have shortened internodes. The shortened internodes lead to shorter plants that do not require staking.

The methods can be used to introduce a brachytic phenotype into a Solanaceae plant having a desired characteristic, such as fruit size, fruit number and/or fruit quality. In some embodiments, the brachytic plants do not require staking. In some embodiments, the brachytic plants provide a suitable plant habit for machine harvest. Normal tomato plants may require tying 3-4 times per season. Having shorter tomato plants reduces tying cost (materials & labor costs) under current horticultural practices/cultivation systems. In some embodiments, the described brachytic plants are tied, 0, 1, or 2 times per year. In some embodiments, the described brachytic plants require fewer tyings than normal plants. In some embodiments, the number of tyings of the described brachytic plants during the season is reduced by 1, 2, 3, or 4 times compared to normal plants without the brachytic mutations/disruptions.

CRISPR constructs and systems for directed modification (disruption) of one or more brachytic loci in Solanaceae are described. The modification can be a deletion, a missense mutation, a nonsense mutation, an insertion mutation of a combination of these.

In some embodiments the CRISPR constructs and systems are used to generate genetically modified Solanaceae plants carrying a one or more loss of functions brachytic loci alleles and having a brachytic phenotype. The transgenic plants can then be used to produce progeny brachytic plants. Any of the described CRISPR constructs and systems can be used to generate a transgenic Solanaceae plant carrying a loss of function brachytic locus allele. The described CRISPR constructs and systems can be used to introduce loss of function mutations in one or more of the reading frames located at Solyc01g066950, Solyc01g066970, Solyc06g005530, and Solyc12g099610. The described CRISPR constructs can be further combined with a CRISPR construct or system for introducing a loss of function mutation into an open reading frame located at Solyc01g066980. The CRISPR constructs and systems can be used to introduce loss of function mutations into two or more reading frames simultaneously, sequentially, or a combination thereof A Solanaceae plant can be a *S. Solanum* or a *Capsicum* plant. A *Solanum* plant can be a *S. melongena* (eggplant) plant, a *S. tuberosum* (potato) plant, or a tomato plant. A *Capsicum* plant can be a *C. annuum* (pepper) plant or a *C. frutescens* (tabasco pepper) plant. The term tomato includes but is not limited to any species of tomato. In some embodiments, tomato plant can be a *Solanum lycopersicum* plant, a *S. pimpinellifolium* plant, or a *S. pennellii* plant. In some embodiments, the tomato plant is a *Solanum lycopersicum* plant.

In some embodiments, methods of producing brachytic plants and methods of genetically modifying a plant to produce a brachytic plant using a Clustered Regularly Interspaced Short Palindromic Repeats (CRISPR)/CRISPR-associated (Cas) system are described. In some embodiments, brachytic plants created using a CRISPR system are described. In some embodiments, nucleic acids for producing a brachytic plant using a CRISPR system are described.

BRIEF DESCRIPTION OF THE DRAWINGS

FIG. 5. Diagram illustrating two flowering promoting factor 1 (FPF1) genes (Solyc01g066950 and Solyc01g066970), the centromere-proximal homologs of brachytic. A CRISPR-Cas9 system utilizing a single-guide RNA that targeted a sequence region with only a single nucleotide difference (boxed) between the two homologous FPF1s (i.e., "A" at 68,005,223 bp on Solyc01g066950 and "G" at 68,057,560 bp on Solyc01g066970) as used to generate loss of function mutations. The first nucleotide position of the each start codon is given. Sequences of three different mutants (br.7$^{CR}$, br.57.1$^{CR}$, br.57.2$^{CR}$) are shown. Deletions and insertions are indicated by blue dashes and underlines, respectively. The sequence gap length between two genes is shown in parentheses. WT=wild-type.

| Plant | Allele | Sequence | SEQ ID NO: |
|---|---|---|---|
| WT | Solyc01g066950 | CCGTCGCACCGTG AAAGTCACCGAGG | 107 |
| | Solyc01g066970 | CCGTCGCACCGTG GAAGTCACCGGGG | 108 |
| br.7$^{CR}$ | Solyc01g066950 | CCGTCGCACCGTG AAAGTCACCGAGG | 109 |
| | Solyc01g066970 | CCGTCGCAACCGT GGAAGTCACCGGG G | 110 |
| br.57.1$^{CR}$ | Solyc01g066950 | CCGTCGCACCGTG AACCGAGG | 111 |
| | Solyc01g066970 | CCGTCGCACCGTG GACCGGGG | 112 |
| br.57.2$^{CR}$ | Solyc01g066950 | CCGTCGCACCGTG AAAGTCAACCGAG G | 113 |
| | Solyc01g066970 | CCGTCGCACCGTG GACCGGGG | 114 |

Figure 6:
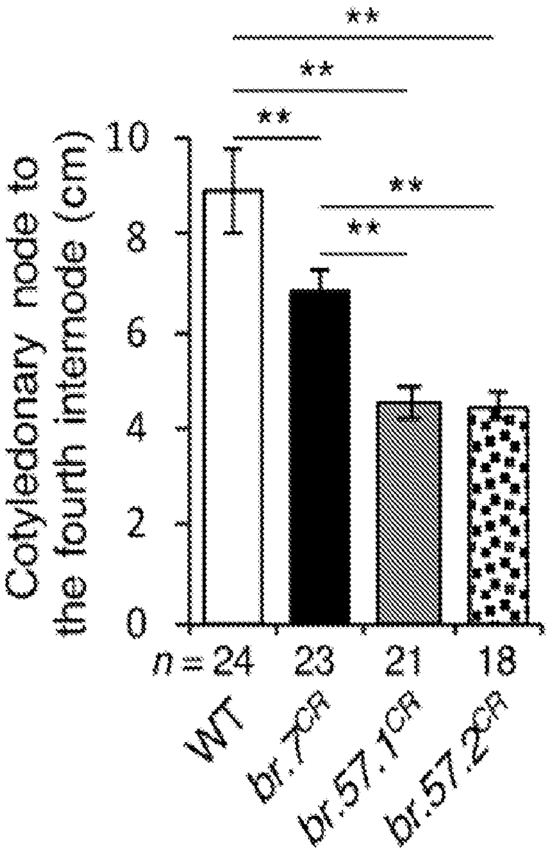

FIG. 6. Graph illustrating reduced plant height in plants harboring mutated brachytic homologs at Solyc01g066950 and Solyc01g066970. Stem lengths of 6-week-old plants are shown. Mutants are transgene-free, homozygous M2 generation. The n value represents the total number of plants for each genotype evaluated. **p<0.01 based on one-way ANOVA in conjunction with a two-tailed Tukey's HSD multiple comparison test. Error bars indicate 95% confidence intervals.

DETAILED DESCRIPTION

I. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (Ausbel et al., eds., John Wiley & Sons, Inc. 2001; Transgenic Plants: Methods and Protocols (Leandro Pena, ed., Humana Press, 1st edition, 2004); and, *Agrobacterium* Protocols (Wan, ed., Humana Press, 2nd edition, 2006). As appropriate, procedures involving the use of commercially available kits and reagents are generally carried out in accordance with manufacturer defined protocols and/or parameters unless otherwise noted.

The use of "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

The term "about" or "approximately" indicates within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0 to 20%, 0 to 10%, 0 to 5%, or up to 1% of a given value. Where particular values are described in the application and claims, unless otherwise stated the term "about" meaning within an acceptable error range for the particular value should be assumed.

All ranges are to be interpreted as encompassing the endpoints in the absence of express exclusions such as "not including the endpoints"; thus, for example, "within 10-15" includes the values 10 and 15. One skilled in the art will understand that the recited ranges include the end values, as whole numbers in between the end values, and where practical, rational numbers within the range (e.g., the range 5-10 includes 5, 6, 7, 8, 9, and 10, and where practical, values such as 6.8, 9.35, etc.). When values are expressed as approximations, by use of the antecedent "about," it will be understood that the particular value forms a further aspect. For example, if the value "about 10" is disclosed, then "10" is also disclosed.

The term "nucleic acid" refers to deoxyribonucleotides or ribonucleotides and polymers thereof ("polynucleotides") in either single- or double-stranded form. Unless specifically limited, the term polynucleotide encompasses nucleic acids containing known analogues of natural nucleotides which have similar binding properties as the reference nucleic acid and are metabolized in a manner similar to naturally occurring nucleotides. Unless specifically limited, the term polynucleotide encompasses nucleic acids having one or more modified nucleotides. Modified nucleotides can modify binding properties or alter in vitro or in vivo stability. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a sequence comparison algorithms, or by manual alignment and visual inspection.

The term "plant" includes whole plants, plant organs (e.g., leaves, stems, flowers, roots, reproductive organs, embryos and parts thereof, etc.), seedlings, seeds and plant cells and progeny thereof. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

"Early flowering" refers to increasing the ability of the plant to exhibit early flowering as compared to a matching control plant (e.g., a similar plant not having the brachytic phenotype). In some embodiments, early flowering indicates a shorter time period between germination to the time in which the first flower opens. In some embodiments, increasing early flowering of a population of plants increases the number or percentage of plants having an early flowering. In some embodiments, early flowering enables the plant to produce more flowers, fruits, pods and seeds without changing plant maturity period. Early flowering can also lead to increased yield by providing a longer grain filling or fruit maturation period.

The term "locus" refers to a position on the genome that corresponds to a measurable characteristic (e.g., a trait) or gene. A locus can be a genomic region or section of DNA (the locus) which correlates with a variation in a phenotype. A locus can comprise a single or multiple genes or other genetic information within a contiguous genomic region or linkage group.

"Introgression" or "introgressing" of a brachytic locus means introduction of a brachytic locus from a donor plant comprising the brachytic locus into a recipient plant by standard breeding techniques, wherein selection can be done phenotypically by means of observation of the internodal length or plant height, or selection can be done with the use of brachytic markers through marker-assisted breeding, or combinations of these. The process of introgressing is often referred to as "backcrossing" when the process is repeated two or more times. In introgressing or backcrossing, the "donor" parent refers to the parental plant with the desired gene or locus to be introgressed. The "recipient" parent (used one or more times) or "recurrent" parent (used two or more times) refers to the parental plant into which the gene or locus is being introgressed. Selection is started in the F1 or any further generation from a cross between the recipient plant and the donor plant, suitably by using markers as identified herein. The skilled person is however familiar with creating and using new molecular markers that can identify or are linked to the brachytic locus.

A "homolog" or "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologs (orthologous sequences) and paralogs (paralogous sequences). Homologous genes, for example, typically descend from a common ancestral DNA sequence, either through a speciation event (orthologous genes) or a genetic duplication event (paralogous genes). "Orthologous" genes are genes in different species that evolved from a common ancestral gene by speciation. Orthologs typically retain the same function in the course of evolution. "Paralogous" genes include genes related by duplication within a genome. Paralogs can evolve new functions in the course of evolution.

Compositions or methods "comprising" or "including" one or more recited elements may include other elements not specifically recited. For example, a composition that "comprises" or "includes" a marker may contain the marker alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

The term "and/or" refers to and encompasses any and all possible combinations of one or more of the associated listed items, as well as the lack of combinations when interpreted in the alternative ("or"). The term "or" refers to any one member of a particular list and also includes any combination of members of that list.

The singular forms of the articles "a," "an," and "the" include plural references unless the context clearly dictates otherwise. For example, the term "a marker" or "at least one marker" can include a plurality of markers, including mixtures thereof.

An "RNA-guided DNA endonuclease" is an enzyme (endonuclease) that uses RNA-DNA complementarity to identify target sites for sequence-specific double-stranded DNA (dsDNA) cleavage. An RNA-guided DNA endonuclease may be, but is not limited to, a zCas9 nuclease, a Cas9 nuclease, type II Cas nuclease, an nCas9 nuclease, a type V Cas nuclease, a Cas12a nuclease, a Cas12b nuclease, a Cas12c nuclease, a CasY nuclease, a CasX nuclease, a Cas12i nuclease, or an engineered RNA-guided DNA endonuclease.

A "guide RNA" (gRNA) comprises an RNA sequence (tracrRNA) bound by Cas and a spacer sequence (crRNA) that hybridizes to a target sequence and defines the genomic target to be modified. The tracrRNA and crRNA may be linked to form a "single chimeric guide RNA" (sgRNA).

The term "CRISPR RNA (crRNA)" has been described in the art (e.g., in Makarova et al. (2011) *Nat Rev Microbiol* 9:467-477; Makarova et al. (2011) *Biol Direct* 6:38; Bhaya et al. (2011) *Annu Rev Genet* 45:273-297; Barrangou et al. (2012) *Annu Rev Food Sci Technol* 3:143-162; Jinek et al. (2012) *Science* 337:816-821; Cong et al. (2013) *Science* 339:819-823; Mali et al. (2013) *Science* 339: 823-826; and Hwang et al. (2013) *Nature Biotechnol* 31:227-229). A crRNA contains a sequence (spacer sequence or guide sequence) that hybridizes to a target sequence in the genome. A target sequence can be any sequence that is unique compared to the rest of the genome and is adjacent to a protospacer-adjacent motif (PAM).

A "protospacer-adjacent motif" (PAM) is a short sequence recognized by the CRISPR complex. The precise sequence and length requirements for the PAM differ depending on the CRISPR system used, but PAMs are typically 2-5 base pair sequences adjacent the protospacer (i.e., target sequence). Non-limiting examples of PAMs include NGG, NNGRRT, NN[A/C/T]RRT, NGAN, NGCG, NGAG, NGNG, NGC, and NGA.

A "trans-activating CRISPR RNA" (tracrRNA) is an RNA species facilitates binding of the RNA-guided DNA endonuclease (e.g., Cas) to the guide RNA.

A "CRISPR system" comprises a guide RNA, either as a crRNA and a tracrRNA (dual guide RNA) or an sgRNA, and RNA-guided DNA endonuclease. The guide RNA directs sequence-specific binding of the RNA-guided DNA endonuclease to a target sequence. In some embodiments, the RNA-guided DNA endonuclease contains a nuclear localization sequence. In some embodiments, the CRISPR system further comprises one or more fluorescent proteins and/or one or more endosomal escape agents. In some embodiments, the gRNA and RNA-guided DNA endonuclease are provided in a complex. In some embodiments, the gRNA and RNA-guided DNA endonuclease are provided in one or more expression constructs (CRISPR constructs) encoding the gRNA and the RNA-guided DNA endonuclease. Delivery of the CRISPR construct(s) to a cell results in expression of the gRNA and RNA-guided DNA endonuclease in the cell. The CRISPR system can be, but is not limited to, a CRISPR class 1 system, a CRISPR class 2 system, a CRISPR/Cas system, a CRISPR/Cas9 system, a CRISPR/zCas9 system and a CRISPR/Cas3 system.

A "regenerant" is a plant produced from a plant tissue cell, such as a genetically modified plant tissue cell.

II. Overview

Described are compositions, including CRISPR constructs, for modifying one or more brachytic loci in a plant and methods of using the compositions for producing plants having a brachytic phenotype (i.e., brachytic plants). In some embodiments, the plant is a Solanaceae plant A Solanaceae plant can be, but is not limited to, a *Solanum* or a *Capsicum* plant. A *Solanum* plant can be, but is not limited to, a *S. melongena* (eggplant) plant, *S. tuberosum* (potato) plant, or a tomato plant. A *Capsicum* plant can be, but is not limited to, a *C. annuum* (pepper) plant or a *C. frutescens* (tabasco pepper) plant. In some embodiments, the Solanaceae plant is a tomato plant. The term tomato is not limited to any species or variety of tomato. In some embodiments, tomato plant can be a *Solanum lycopersicum* plant, a *S. pimpinellifolium* plant, or a *S. pennellii* plant. In some embodiments, the tomato plant is a *Solanum lycopersicum* plant.

In some embodiments, the brachytic loci are homologs of the Br gene located at Solyc01g066980 (also termed flowering promoting factor 1 or FPF1).

In some embodiments, nucleic acids for producing brachytic plants using CRISPR systems are described. The CRISPR systems can target one or more of the brachytic loci. The nucleic acids include, but are not limited to, nucleic acids comprising crRNAs or gRNAs and nucleic acids encoding crRNAs or gRNAs.

In some embodiments, methods of producing brachytic Solanaceae plants and methods of genetically modifying a Solanaceae plant to produce a brachytic plant using a CRISPR system are described.

In some embodiments, Solanaceae plants having a brachytic phenotype produced using any one or more of the described CRISPR constructs are described.

A "brachytic plant" is characterized by having shortened internodes without a substantial corresponding reduction in the number of size of other plant parts (brachytic phenotype). Shortened internodes drive shortened stem length/plant height compared to normal plants. Brachytic (shortened) internodes are distinguishable from a dwarf-mediated phenotype in which all parts are shortened. In some embodiments, the brachytic plants also have accelerated or early flowering.

A "brachytic locus" comprises a locus that corresponds to the brachytic measurable trait (phenotype). Plants homozygous for a loss of function mutation at a brachytic locus exhibit the brachytic phenotype, i.e., the plants have a shorter internode length compared to otherwise genetically similar plants that are not homozygous for the loss of function mutation at the brachytic locus. Plants homozygous for a wild-type gene at a brachytic locus exhibit normal growth with respect to the brachytic phenotype. Plants heterozygous at the brachytic locus, carrying one wild-type brachytic allele and one loss of function brachytic allele, may exhibit intermediate growth characteristics with respect to the brachytic phenotype. Brachytic loci include homologs and paralogs of SEQ ID NO: 21 or 22 (Solyc01g066980 locus) in tomato plants and orthologs thereof in other Solanaceae plants. In some embodiments, a brachytic locus is selected from the group consisting of: a Solyc01g066950 locus, a Solyc01g066970 locus, a Solyc06g005530 locus, and a Solyc12g099610 locus, and orthologs thereof.

A "Solyc01g066950 locus" comprises Solyc01g066950.1.1: SEQ ID NO: 2 (DNA).

A "Solyc01g066970 locus" comprises Solyc01g066970.2.1: SEQ ID NO: 7 (DNA).

A "Solyc06g005530 locus" comprises Solyc06g005530.2.1: SEQ ID NO: 12 (DNA).

A "Solyc12g099610 locus" comprises Solyc12g099610.1.1: SEQ ID NO: 17 (DNA).

A "Solyc01g066980 locus" comprises Solyc01g066980.2.1: SEQ ID NO: 102 (DNA).

In some embodiments, the brachytic locus includes sequence 5' and/or 3' of the coding sequence. In some embodiments, a "Solyc01g066950 locus" comprises Solyc01g066950.1.1: SEQ ID NO: 1 (DNA). In some embodiments, a "Solyc01g066970 locus" comprises Solyc01g066970.2.1: SEQ ID NO: 6 (DNA). In some embodiments, a "Solyc06g005530 locus" comprises Solyc06g005530.2.1: SEQ ID NO: 11 (DNA). In some embodiments, a "Solyc12g099610 locus" comprises Solyc12g099610.1.1: SEQ ID NO: 16 (DNA). In some embodiments, a "Solyc01g066980 locus" comprises Solyc01g066980.2.1: SEQ ID NO: 102 (DNA; US202010045901).

The described brachytic loci can be targeted to genetically modify Solanaceae plants to yield a brachytic phenotype. Solanaceae plants having a loss of function mutation in both alleles (homozygous plants) of one or more of the brachytic loci have shortened internodes compared to the otherwise genetically identical plants homozygous for wild-type alleles and the brachytic loci. Solanaceae plants having a loss of function mutation in one alleles (heterozygous plants) of one or more of the brachytic loci may have shortened internodes compared to the otherwise genetically identical plants homozygous for wild-type alleles and the brachytic loci.

III. CRISPR Systems

Described are nucleic acids for producing brachytic plants using a CRISPR (e.g., CRISPR/Cas) system are described. The described nucleic acids can be used to target modification/mutation of one or more brachytic loci in a plant.

A CRISPR system comprises an RNA-guided DNA endonuclease enzyme and a CRISPR RNA. In some embodiments, a CRISPR RNA is part of a guide RNA. In some embodiments, the RNA-guided DNA endonuclease enzyme is a Cas9 protein. In some embodiments, a CRISPR system comprises one or more nucleic acids encoding an RNA-guided DNA endonuclease enzyme (such as, but not limited to a Cas9 protein) and a guide RNA. A guide RNA can comprise a CRISPR RNA (crRNA) and a trans-activating CRISPR RNA (tracrRNA), either as separate molecules or a single chimeric guide RNA (sgRNA). The guide RNA contains a guide sequence having complementarity to a sequence in the target gene genomic region. The Cas protein can be introduced into the plant in the form of a protein or a nucleic acid (DNA or RNA) encoding the Cas protein (e.g., operably linked to a promoter expressible in the plant). The guide RNA can be introduced into the plant in the form of RNA or a DNA encoding the guide RNA (e.g., operably linked to a promoter expressible in the plant). In some embodiments, the CRISPR system can be delivered to a plant or plant cell via a bacterium. The bacterium can be, but is not limited to, *Agrobacterium tumefaciens.*

The CRISPR system is designed to target one or more of the described brachytic loci. The CRISPR/Cas system can be, but is not limited to, a CRISPR class 1 system, CRISPR class 2 system, CRISPR/Cas system, a CRISPR/Cas9 system, a CRISPR/zCas9 system or CRISPR/Cas3 system.

Guide sequences suitable for forming gRNAs or crRNAs for CRISPR system mediated genetic modification of a brachytic locus are described. Suitable guide sequences include 17-20 nucleotide sequences in any of SEQ ID NOs: 1, 2, 6, 7, 11, 12, 16, 17, 21, and 102 or a complement thereof that are unique compared to the rest of the genome and immediately adjacent (5') to a protospacer-adjacent motif (PAM) site. For the RNA-guided DNA endonuclease enzyme zCas9, a PAM site is NGG. Thus, any unique 17-20 nucleotide sequence immediately 5' of a 5'-NGG-3' in SEQ ID NO: 1, 2, 6, 7, 11, 12, 16, 17, 21, and 102 or a complement thereof can be used in forming a gRNA. zCas9 PAM sites in SEQ ID NOs: 1, 2, 6, 7, 11, 12, 16, 17, 21, and 102, GG and CC, are shown in bold capital letters (Table 1). CC sequences in the listed strand correspond to GG sequences in the complementary strand. Deletions or insertions in the flanking regions may alter expression of the gene leading to plants displaying a brachytic phenotype. In some embodiments, the guide sequence is 100% complementary to the target sequence. In some embodiments, the guide sequence is at least 90% or at least 95% complementary to the target sequence. In some embodiments, the guide sequence contains 0, 1, or 2 mismatches when hybridized to the target sequence. In some embodiments, a mismatch, if present, is located distal to the PAM, in the 5' end of the guide sequence.

CRISPR modification of a brachytic locus is not limited to the CRISPR/zCas9 system. Other CRISPR systems using different nucleases and having different PAM sequence requirements are known in the art. PAM sequences vary by the species of RNA-guided DNA endonuclease. For example, Class 2 CRISPR-Cas type II endonuclease derived from *S. pyogenes* utilizes an NGG PAM sequence located on the immediate 3' end of the guide sequence. Other PAM sequences include, but are not limited to, NNNNGATT (*Neisseria meningitidis*), NNAGAA (*Streptococcus thermophiles*), and NAAAAC (*Treponema denticola*). Guide sequences for CRISPR systems having nucleases with different PAM sequence requirements are identified as described above for zCas9, substituting the different PAM sequences.

In some embodiments, the CRISPR system comprises one or more RNA-guided DNA endonucleases or one or more nucleic acids encoding the one or more RNA-guided DNA endonuclease, and one or more of:

(a) a guide RNA comprising a 17-20 nucleotide guide sequence comprising 17-20 contiguous nucleotides from SEQ ID NO: 1 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(b) a guide RNA comprising a 17-20 nucleotide guide sequence comprising 17-20 contiguous nucleotides from SEQ ID NO: 6 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(c) a guide RNA comprising a 17-20 nucleotide guide sequence comprising 17-20 contiguous nucleotides from SEQ ID NO: 11 differing by no more than 1 or 2 nucleotides, or a complement thereof, wherein the 17-20 nucleotide sequence is unique compared to the rest of the genome and immediately adjacent (5') to a protospacer-adjacent motif (PAM) site; and (d) a guide RNA comprising a 17-20 nucleotide guide sequence comprising 17-20 contiguous nucleotides from SEQ ID NO: 16 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system further comprises a guide RNA comprising a 17-20 nucleotide guide sequence comprising 17-20 contiguous nucleotides from SEQ ID NO: 21 or 102 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system comprises one or more RNA-guided DNA endonucleases or one or more nucleic acids encoding the one or more RNA-guided DNA endonuclease, and one or more of:

(a) a guide RNA comprising a 17-20 nucleotide guide sequence comprising 17-20 contiguous nucleotides from SEQ ID NO: 2 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(b) a guide RNA comprising a 17-20 nucleotide guide sequence comprising 17-20 contiguous nucleotides from SEQ ID NO: 7 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(c) a guide RNA comprising a 17-20 nucleotide guide sequence comprising 17-20 contiguous nucleotides from SEQ ID NO: 12 differing by no more than 1 or 2 nucleotides, or a complement thereof, wherein the 17-20 nucleotide sequence is unique compared to the rest of the genome and immediately adjacent (5') to a protospacer-adjacent motif (PAM) site; and (d) a guide RNA comprising a 17-20 nucleotide guide sequence comprising 17-20 contiguous nucleotides from SEQ ID NO: 17 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system further comprises a guide RNA comprising a 17-20 nucleotide guide sequence comprising 17-20 contiguous nucleotides from SEQ ID NO: 21 or 102 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system comprises one or more RNA-guided DNA endonucleases or one or more nucleic acids encoding the one or more RNA-guided DNA endonuclease, and one or more of:

(a) one or more guide RNAs each comprising a 17-20 nucleotide guide sequence comprising 17-20 contiguous nucleotides from SEQ ID NO: 1 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(b) one or more guide RNAs each comprising a 17-20 nucleotide guide sequence comprising 17-20 contiguous nucleotides from SEQ ID NO: 6 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(c) one or more guide RNAs each comprising a 17-20 nucleotide guide sequence comprising 17-20 contiguous nucleotides from SEQ ID NO: 11 differing by no more than 1 or 2 nucleotides, or a complement thereof, wherein the 17-20 nucleotide sequence is unique compared to the rest of the genome and immediately adjacent (5') to a protospacer-adjacent motif (PAM) site; and (d) one or more guide RNAs each comprising a 17-20 nucleotide guide sequence comprising 17-20 contiguous nucleotides from SEQ ID NO: 16 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system further comprises a guide RNA comprising a 17-20 nucleotide guide sequence comprising 17-20 contiguous nucleotides from SEQ ID NO: 21 or 102 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system comprises one or more RNA-guided DNA endonucleases or one or more nucleic acids encoding the one or more RNA-guided DNA endonuclease, and one or more of:

(a) one or more guide RNAs each comprising a 17-20 nucleotide guide sequence comprising 17-20 contiguous nucleotides from SEQ ID NO: 2 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(b) one or more guide RNAs each comprising a 17-20 nucleotide guide sequence comprising 17-20 contiguous nucleotides from SEQ ID NO: 7 differing by no more than 1 or 2 nucleotides, or a complement thereof, wherein the 17-20 nucleotide sequence is unique compared to the rest of the genome and immediately adjacent (5') to a protospacer-adjacent motif (PAM) site;

(c) one or more guide RNAs each comprising a 17-20 nucleotide guide sequence comprising 17-20 contiguous nucleotides from SEQ ID NO: 12 differing by no more than 1 or 2 nucleotides, or a complement thereof, wherein the 17-20 nucleotide sequence is unique compared to the rest of the genome and immediately adjacent (5') to a protospacer-adjacent motif (PAM) site; and (d) one or more guide RNAs each comprising a 17-20 nucleotide guide sequence comprising 17-20 contiguous nucleotides from SEQ ID NO: 17 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system further comprises a guide RNA comprising a 17-20 nucleotide guide sequence comprising 17-20 contiguous nucleotides from SEQ ID NO: 21 or 102 differing by no more than 1 or 2 nucleotides, or a complement thereof, wherein the 17-20 nucleotide sequence is unique compared to the rest of the genome and immediately adjacent (5') to a protospacer-adjacent motif (PAM) site.

In some embodiments, the CRISPR system comprises one or more guide RNAs selected from the group consisting of: a guide RNA comprising SEQ ID NO: 5, a guide RNA comprising SEQ ID NO: 9, a guide RNA comprising SEQ ID NO: 10, a guide RNA comprising SEQ ID NO: 14, a guide RNA comprising SEQ ID NO: 15, a guide RNA comprising any one of SEQ ID NO: 76-92, a guide RNA comprising SEQ ID NO: 19, a guide RNA comprising SEQ ID NO: 20, and a guide RNA comprising any one of SEQ ID NO: 92-101. The sequences in Table 1 are listed as DNA sequences. It is understood that RNA equivalents of the listed DNA sequences, substituting uracils (U) for thymines (T), may be used. An "RNA equivalent" is an RNA molecule having essentially the same complementary base pair hybridization properties as the listed DNA sequence.

In some embodiments, the CRISPR system further comprises a guide RNA comprising TCTAGTGGAGAACTCCGAT (SEQ ID NO: 103; wherein T's can be U's), a guide RNA comprising AAAAGTTCTTGTACATCTTC (SEQ ID NO: 104; wherein T's can be U's), or a guide RNA comprising SEQ ID NO: 103 and a guide RNA comprising SEQ ID NO: 104.

In some embodiments, the CRISPR system comprises one or more guide sequences selected from the group consisting of: a guide RNA comprising SEQ ID NO: 5, a guide RNA comprising SEQ ID NO: 9, a guide RNA comprising SEQ ID NO: 10, a guide RNA comprising SEQ ID NO: 14, a guide RNA comprising SEQ ID NO: 15, a guide RNA comprising any one of SEQ ID NO: 76-92, a guide RNA comprising SEQ ID NO: 19, a guide RNA comprising SEQ ID NO: 20, and a guide RNA comprising any one of SEQ ID NO: 92-101. It is understood that RNA equivalents of the listed DNA sequences, substituting uracils (U) for thymines (T), may be used. An "RNA equivalent" is an RNA molecule having essentially the same complementary base pair hybridization properties as the listed DNA sequence.

In some embodiments, the CRISPR system further comprises a guide RNA comprising a 17-20 nucleotide guide sequence comprising 17-20 contiguous nucleotides from SEQ ID NO: 21 or 102 differing by no more than 1 or 2 nucleotides, or a complement thereof, wherein the 17-20 nucleotide guide sequence is unique compared to the rest of the genome and immediately adjacent (5') to a protospacer-adjacent motif (PAM) site.

Two or more guide RNAs can used with the same RNA-guided DNA endonuclease (e.g., Cas nuclease) or different RNA-guided DNA endonucleases.

In some embodiments, two or more gRNAs targeting two or more different brachytic loci are used. The two or more gRNAs can be used with the same RNA-guided DNA endonuclease or different RNA-guided DNA endonucleases.

In some embodiments, three or more gRNAs targeting three or more different brachytic loci are used. The three or more gRNAs can used with the same RNA-guided DNA endonuclease or different RNA-guided DNA endonucleases.

In some embodiments, four or more gRNAs targeting four or more different brachytic loci are used. The four or more gRNAs can used with the same RNA-guided DNA endonuclease or different RNA-guided DNA endonucleases.

In some embodiments, five or more gRNAs targeting five or more different brachytic loci are used. The five or more gRNAs can used with the same RNA-guided DNA endonuclease or different RNA-guided DNA endonucleases.

In some embodiments, two or more gRNAs targeting a single brachytic locus can be used. The two or more gRNAs can used with the same RNA-guided DNA endonuclease (Cas nuclease) or different RNA-guided DNA endonucleases.

It is noted that, for RNA sequences, T's of SEQ ID NO: 1, 2, 6, 7, 11, 12, 16, 17, 21, and 102 can be U's. In some embodiments, the PAM site is 5'-NGG-3'.

Guide RNAs for modification of brachytic loci in other Solanaceae plants are generated in a similar manner by identifying the corresponding ortholog sequences of the Solyc01g066950 locus, the Solyc01g066970 locus, the Solyc06g005530 locus, and/or the Solyc12g099610 locus in the other Solanaceae plants and selecting target sequences as described above. Exemplary orthologs of brachytic loci as shown in Tables 2A-F.

Any of the above described guide RNAs can be provided as an RNA or a DNA encoding the RNA.

In some embodiments, a CRISPR system comprises one or more guide RNAs and a nucleic acid encoding an RNA-guided DNA endonuclease.

In some embodiments, a CRISPR system comprises one or more guide RNAs and a one or more nucleic acids encoding two or more different RNA-guided DNA endonucleases.

In some embodiments, a CRISPR system comprises a guide RNA and an RNA-guided DNA endonuclease in a complex. In some embodiments, a CRISPR system comprises a guide two or more RNAs each in a complex with an RNA-guided DNA endonuclease.

IV. CRISPR-Modified Plants

Methods of producing brachytic plants and methods of genetically modifying a plant to produce a brachytic plant using a CRISPR system are described.

Described are methods of generating genetically modified brachytic plants comprising introducing into a plant, a plant tissue, or a plant cell, one or more of the described CRISPR systems. In some embodiments, genetically modified brachytic plants created using a CRISPR system are described. In some embodiments, the CRISPR system is a CRISPR/Cas system.

In some embodiments, methods are described for producing a brachytic tomato plant, the methods comprising the steps of: a) introducing into the plant one or more of the described CRISPR systems. In some embodiments, at least two CRISPR guide RNA's are used.

Nucleic acids may be introduced into a plant cell or cells using a number of methods known in the art, including but not limited to electroporation, DNA bombardment or biolistic approaches, microinjection, via the use of various DNA-based vectors such as *Agrobacterium tumefaciens* and *Agrobacterium rhizogenes* vectors, and CRISPR or CRISPR/Cas9. Once a plant cell has been successfully transformed, it may be cultivated to regenerate a transgenic plant (regenerant).

Various methods for introducing the transgene expression vector constructs of the invention into a plant or plant cell are well known to those skilled in the art, and any method capable of transforming the target plant or plant cell may be utilized.

In some embodiments, *Agrobacterium tumefaciens* is used to deliver CRISP system nucleic acids to a plant. *Agrobacterium*-mediated transformation of a large number of plants are extensively described in the literature (see, for example, *Agrobacterium Protocols*, Wan, ed., Humana Press, $2^{nd}$ edition, 2006). Various methods for introducing DNA into *Agrobacteria* are known, including electroporation, freeze/thaw methods, and triparental mating. In some embodiments, a pMON316-based vector is used in the leaf disc transformation system of Horsch et al. Other commonly used transformation methods include, but are not limited to, microprojectile bombardment, biolistic transformation, and protoplast transformation of naked DNA by calcium, polyethylene glycol (PEG) or electroporation (Paszkowski et al., 1984, EMBO J. 3: 2727-2722; Potrykus et al., 1985, Mol. Gen. Genet. 199: 169-177; Fromm et al., 1985, Proc. Nat. Acad. Sci. USA 82: 5824-5828; Shimamoto et al., 1989, Nature, 338: 274-276.

$T_0$ transgenic plants may be used to generate subsequent generations (e.g., $T_1$, $T_2$, etc.) by selfing of primary or secondary transformants, or by sexual crossing of primary or secondary transformants with other plants (transformed or untransformed).

The described CRISPR systems can be used to genetic modify one or more brachytic loci in a plant. The plant can be a plant having a trait of interest. Delivery of the CRISPR system leads to small nucleotide insertions or deletions in or near the target sequence, resulting in disruption of the targeted brachytic locus. Introducing a brachytic phenotype into a plant having a desired trait may result in a cost savings for plant developers, because such methods eliminate traditional plant breeding. A disruption is a modification, such as a deletion, a missense mutation, a nonsense mutation, an insertion mutation of a combination of these, that results in a loss of function of the locus or protein encoded by the locus or reduced expression of the locus or protein encoded by the locus. In some embodiments, the disruption comprises a deletion. In some embodiments, the deletion comprises a 1-10 nucleotide or base pair deletion. In some embodiments, the deletion comprises a 1-5 nucleotide or base pair deletion. In some embodiments, the deletion comprises a 1, 2, 3, 4, 5, 6, 7, 8, 9, or 10 nucleotide or base pair deletion.

In some embodiments, the described CRISPR systems can be used to genetic modify 1, 2, 3, 4, or 5 brachytic loci in a plant.

In some embodiments, the described CRISPR constructs may be used to introduce one or more determinants of brachytic into a Solanaceae plant by genetic transformation.

In some embodiments, the CRISPR system is modify one or more brachytic loci into a transgenic tomato line. The transgenic tomato line can contain one or more genes for herbicide tolerance, increased yield, insect control, fungal disease resistance, virus resistance, bacterial disease resistance, germination and/or seedling growth control, enhanced animal and/or human nutrition, improved processing traits, or improved flavor, among others.

Plants produced using the described CRISPR systems (having loss of function mutations in one or more brachytic homolog loci) have a brachytic phenotype. The brachytic plants can produce similar sizes and quantities of fruit to an otherwise genetically similar plants lacking the loss of function mutations in the one or more brachytic homolog loci. In some embodiments, the brachytic plants produce fruits at a yield of greater than 50%, greater than 60%, greater than 70%, greater than 80%, or greater than 90% of the yield of an otherwise genetically similar plant lacking the loss of function mutation in one or more brachytic loci when grown under the same conditions. In some embodiments, the brachytic plants produce fruits having an average size that is greater than 50%, greater than 60%, greater than 70%, greater than 80%, or greater than 90% of the average size of fruits produced by an otherwise genetically similar plant lacking the loss of function mutation in one or more brachytic loci when grown under the same conditions. In some embodiments, the brachytic plants produce fruits having an average weight that is greater than 50%, greater than 60%, greater than 70%, greater than 80%, or greater than 90% of the average weight of fruits produced by an otherwise genetically similar plant lacking the loss of function mutation in one or more brachytic loci when grown under the same conditions. In some embodiments, the brachytic plants produce greater than 50%, greater than 60%, greater than 70%, greater than 80%, or greater than 90% of the number of medium size or larger fruits per plant compared to the number of medium size or larger fruits per plant produced by an otherwise genetically similar plant lacking the loss of function mutation in one or more brachytic loci when grown under the same conditions. In some embodiments, the brachytic plants produce greater than 50%, greater than 60%, greater than 70%, greater than 80%, or greater than 90% of the number of large or extra large size fruits per plant compared to the number of large or extra large size fruits per plant produced by an otherwise genetically similar plant lacking the loss of function mutation in one or more brachytic loci when grown under the same conditions.

Tomato Fruit Size

| Size | Diameter in inches (mm) | Weight in ounces (grams) |
|---|---|---|
| Small | $2\frac{1}{8}-2\frac{9}{32}$ (53.98-57.94) | <3 oz (<85) |
| Medium | $2\frac{1}{4}-2\frac{17}{32}$ (57.15-64.29) | 3-6 oz (85-170) |
| Large | $2\frac{1}{2}-2\frac{25}{32}$ (63.5-70.64) | >6 to 10 oz (>170-283) |
| Extra Large | $\geq 2\frac{3}{4}$ (69.85) | >10 oz (>283) |

V. Sequences

The nucleotide and amino acid sequences listed in the accompanying sequence listing are shown using standard letter abbreviations for nucleotide bases, and single-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

VI. Detection of a Modified Gene

Modification of a brachytic locus using any of the described CRISPR constructs can be detected or confirmed by any means known in the art for detecting genetic modifications.

In some embodiments, a modification can be detected in genomic DNA sample. Genomic DNA samples include, but are not limited to, genomic DNA isolated directly from a plant, cloned genomic DNA, or amplified genomic DNA.

Genetic analysis methods include, but are not limited to, polymerase chain reaction (PCR)-based detection methods (for example, TaqMan assays), microarray methods, mass spectrometry-based methods and/or nucleic acid sequencing methods, including whole genome sequencing. In some embodiments, the detection of genetic modification in a sample of DNA, RNA, or cDNA may be facilitated through the use of nucleic acid amplification methods. Such methods specifically increase the concentration of polynucleotides that span a target site, or include that site and sequences located either distal or proximal to it. Such amplified molecules can be readily detected by gel electrophoresis, fluorescence detection methods, or other means.

In some embodiments, a brachytic locus genetic modification is detected by hybridization to allele-specific oligonucleotide (ASO) probes. ASO probes are disclosed in U.S. Pat. Nos. 5,468,613 and 5,217,863. 5,468,613. Single or multiple nucleotide variations in nucleic acid sequence can be detected in nucleic acids by a process in which the sequence containing the nucleotide variation is amplified, spotted on a membrane and treated with a labeled allele-specific oligonucleotide probe.

In some embodiments, a brachytic locus genetic modification is detected by probe ligation methods. Probe ligation methods disclosed in U.S. Pat. No. 5,800,944 where sequence of interest is amplified and hybridized to probes followed by ligation to detect a labeled part of the probe.

In some embodiments, microarrays can be used for detection of brachytic locus genetic modification. For microarray detection, oligonucleotide probe sets are assembled in an overlapping fashion to represent a single sequence such that a difference in the target sequence at one point would result in partial probe hybridization (Borevitz et al., Genome Res. 13:513-523, 2003; Cui et al., Bioinformatics 21:3852-3858, 2005). Typing of target sequences by microarray-based methods is disclosed in U.S. Pat. Nos. 6,799,122; 6,913,879; and 6,996,476.

In some embodiments, a brachytic locus genetic modification can be directly identified or sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

In some embodiments, the presence of a brachytic marker in a plant may be detected through the use of a nucleotide probe. A probe may be, but is not limited to, nucleotide molecule, polynucleotide, oligonucleotide, DNA molecule, RNA molecule, PNA, UNA, locked nucleotide, or modified polynucleotide. Polynucleotides can be synthesized by any means known in the art. A probe may contain all or a portion of the nucleotide sequence of the genetic marker and optionally, one or more additional sequences. The one or more additional sequences can be contiguous nucleotide sequence from the plant genome, non-contiguous nucleotide sequence from the plant genome, or sequence that is not from the plant genome. Additional, contiguous nucleotide sequence can be "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome.

A polynucleotide probe may be labeled or unlabeled. A wide variety of techniques are readily available in the art for labeling a nucleotide probe. Nucleotide labels include, but are not limited to, radiolabeling, fluorophores, haptens, antibodies, antigens, enzymes, enzyme substrates, enzyme cofactors, and enzyme inhibitors. A label may provide a detectable signal by itself (e.g., a radiolabel or fluorophore) or in conjunction with other agents.

A probe may be an exact copy of a marker to be detected. A probe may also be a nucleic acid molecule comprising, or consisting of, a nucleotide sequence which is substantially identical to a cloned segment of the Solanaceae chromosomal DNA. The term "substantially identical" may refer to nucleotide sequences that are more than 85% identical. For example, a substantially identical nucleotide sequence may be 86%, 87%, 88%, 89%, 90%, 91%, 92%, 93%, 94%, 95%, 96%, 97%, 98%, or 99% identical to the reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired. Thus, an oligonucleotide probe is "specifically hybridizable" to a maker allele if stable and specific binding occurs between the oligonucleotide probe and the marker allele (e.g., a SNP marker) under stringent hybridization conditions, but stable and specific binding does not occur between the oligonucleotide probe and the wild-type allele at the marker position.

In some embodiments, a probe comprises a pair primers designed to produce an amplification product, wherein the amplification product is directly or indirectly determinative for the presence or absence of a brachytic marker

TABLE 1

CRISPR modification of tomato plants - sequences (underlined sequence = open reading frame; dotted underline sequence = intron; boxed sequence = CRISPR target sequence; bold capital letters = zCas9 PAM sites). It is understood that RNA equivalents of the listed DNA sequences, substituting uracils (U) for thymines (T), may be used.

*Solyc01g066950* locus SEQ ID NO: 1 (5'→3')

aatatactcaatctaatgaaCCtaattCCcaaatgagtatGGtattgaGGcttgagtCCtcatgtgtgaacttGGcG
Gtacttattaacgatcatagtacttgttgttgctacatgttgagtaatgtagttgatttcatattattacttgatat
atattgctttctattttgagttGGCCgatgatcgtgttttgtactgaCCCCtacttgtatgtttctttCCttgttat
ttgtGGagtgcagcaaacgtgCCgtcgtctttaactcaaCCgcaactctagCCgatcttcattacaCCGGatttcaG
GGtgagctaacgcttctagcttGGactGGatcttcttcttcatgtctcgatgCCttgaagttCCGGcatgaactagc
ttttatttattctagctttctagatactcttagctttagtaatttgaGGatagatgttcttatgatgatgacttCCa
gattttGGGGataataatagttgttgagtttttagaagttatttaattgattttcattaatgaGGttaagtcttCCg
cattatattCCgtcattatattgaaatgttGGGtttagattGGttGGttcgctcacataGGaagataaatgtGGGtg
CCactcgcGGtCCgttttGGGtcgtgacaGGtaaattaGGGtatcttgtGGCCatataaatattctCCCtttctttt
tctttaatcttatgagcgtacgataagttagtataattctaaatCCtaCCtattaatcatcatcaattttattaaat
aagaaagaaaatacttttttgCCaCCtaatgtatttttattacatagaaaCCCgtataaaaaCCCCttcacacttat
cttcaaactcacacacaatactcactcactagtttcatattcatatttttgaaacatgtctGGtgtttGGaaaatc
aagaatGGagtagtgaGGctagttgagaaCCtcGGtgactttcacGGtgcgacGGGtcgtcgtaaagtgcttgtgca
CCtttctagtaatgaagtaataacatcatatgcagtacttgaaaGGaaactgtactctcttGGatGGGagaGGtact
atgatgaCCCtgaCCttcttcagtaCCataaaagatcaactgttcatcttatttctctaCCaaacgacttcaacaaC
CtcaGGtCCatgcacatgtatgatattgttgttaagaatcgtaatgagtttgctgttaGGGatatgtagtattacta
ataatcattagttgatttgagattttctcaaattaattaatgttgtttaatttaaattaGGttgtttcttcttta
acttaaGGtttGGtttgtgtaatttaGGtcaaaGGGGGGtgttttagtttcttttGGGtgaGGaagctaattattac
ttgttgtaatGGtgtgtaagagtgaagtttatGGcaataaaacttGGtttcgcttcgaaacttttatctatatactt
aaataaatttgtactatcaaatacttaaatttttagtcatatatatatttaaaagtcttctttatttacttaaattt
tgtatcaagtcaaaCCagattatatttttatcattaagCCaacgatgataGGtGGatatgtgattgatatattttttt
tttatGGaaatatcttttcttttctcttttttttttttGGtcttatttgaataaagacaaaatGGtattttCCCatt
tatttcatcaagaagtctttgactataaattcaaaGGctttaCCtcaaattcgaattcttcactgttttaaaaaaat
aaagtaagatgtcaagaatatatatatatatatatatatatatatatatatatatatatatatatatatatatatat
atatatatatatatatatctttttGGGaaatttaattaaattattatgaagcaaataaaGGGtaaaagaacaaata
aataaatgcaatcaaataaatgaagaGGtaatatGGacttGGGcttttcaGGctgctaatttGGGttctGGCCCtat
ttaaaCCtttgaaaacttttgtatacaacaagtgtatattgatatatacagatcgtttctaagCCtttttCCtgtat
atcaactgtatacagCCtgttctaatgCCtCCaaCCtgtatcttcattttttgtcaacatatatgttCCtgaacatat
agatcgctgtatacatattgtatacattatgtatacaactcatttcttGGGcttttgaattatttCCaat

*Solyc01g066950* locus (ORF): SEQ ID NO: 2 (5'→3')

atgtctGGtgtttGGaaaatcaagaatGGagtagtgaGGctagttgagaaCCtcGGtgactttcacGGtgcgacGGG
tcgtcgtaaagtgcttgtgcaCCtttctagtaatgaagtaataacatcatatgcagtacttgaaaGGaaactgtact
ctcttGGatGGGagaGGtactatgatgaCCCtgaCCttcttcagtaCCataaaagatcaactgttcatcttatttct
ctaCCaaacgacttcaacaaCCtcaGGtCCatgcacatgtatgatattgttgttaagaatcgtaatgagtttgctgt
taGGGatatgtag

*Solyc01g066950* locus (encoded amino acid sequence): SEQ ID NO: 3

MSGVWKIKNGVVRLVENLGDFHGATGRRKVLVHLSSNEVITSYAVLERKLYSLGWERYYDDPDLLQYHKR
STVHLISLPNDENNLRSMHMYDIVVKNRNEFAVRDM

*Solyc01g066950* locus guide sequence #2: SEQ ID NO: 5 (5'→3')

cggtgacttccacggtgcga

*Solyc01g066970* locus: SEQ ID NO: 6 (5'→3')

tttctctgtcttgtcttgaaaaaagaatgtttttttttttttataattctttactttcaattcttttacatgtgat
ctttagaagacaagattaaataacattttgatactttctatatattttaattataaaatcacaagattcagaagtct
tgtttatttttttaaaacttcatgtcaaactaaaactagataaacaaattGGaacagacactatCCCattgaaatttt
CCtattgaaaaatgtCCagtGGctatactcacactaatgtttaaattacacaacaaaattaaaaaaaaaactcttGG
tattttagtgagaatttgtttctcaCCatacgtttttattgaCCtagttaaataGGaaatGGGtGGGaatatcacgt TABLE 1-continued CRISPR modification of tomato plants - sequences (underlined sequence = open reading frame; dotted underline sequence = intron; boxed sequence = CRISPR target sequence; bold capital letters = zCas9 PAM sites). It is understood that RNA equivalents of the listed DNA sequences, substituting uracils (U) for thymines (T), may be used.

atcataacacaaatttctcattgatttGGagtaattttttttttttaaaaaaaaattgttattagacattaattaaG
GattaaaagaaacatcatcaacatgagatGGGacaaattaatcttCCCCgaaatatcttttaatttatttaattctt
CCtttttgtgaaGGGctgatcaagcaatGGatataagaatagaagattgttcttagcactaaaaaaattaaagaatt
atgcttGGaaCCCattaaCCaaaagaattaGGttcatcttatgagcataagatcattaattagtgattgtttaGGag
aagattctaatttcagtaGGGcaaattaGGGcatcttgtGGCCatttaaatattctCCCtttctttttctttaatct
taataaacgtacgataagttagtatatttctaaatCCtataagcagCCacattCCaaaatCCtaCCtattatcaatt
ttattaaataagaaaaaagattactttttgCCaCCttatgtattttttttattacacactacatagaaaCCCCtataa
aaaCCCactcacacttatgttcaaactcacacacaatactcacttactatttttcatattcatatattttttgaaaca
tgtctGGtgtttGGGtattcaagaatGGagtagtgaGGctagttgagaaCCCCGGtgacttCCacGGtgcgacGGGt
cgtcgtaaagtgcttgtgcaCCtttctagtaatgaagtaataacatcatatgcagtacttgaaaGGaaactgtactc
tcttGGatGGGagaGGtactatgatgaCCCtgaCCttcttcaattCCataaaagatcaactgttcatcttatttctc
taCCaaaGGacttcaacaaCCtcaagtCCatgcacatgtatgatattgttgttaagaatcgtaatgagtttacagtt
aGGGatatgtagtactactaattaataattagttgatttgagatatttttctcaaattaattaatgttgtttgattt
aaattaGGttgttcttgttttaacttaatgtttGGtttgtgtaatttaGGtttaaGGGGGGtgttttagtttcttt
tGGGtgaGGaagctaattattacttgtaattgtgtgtaagagtgaagttttatGGcaataaaaaaacttGGtttGGc
ttgaaaattttatctatatactgaaataaattcttactatcaaatacttcaatttttgagtctctcacacacgcgcat
atatatatatatatatatatatatatatatatatatatatatatatatacttCCCCgtttaaaaaagaataatcttc
tttCCtttttagtttttttttttCCCCgtttaaaaaagaataatcttctttCCtttttagtttttttttttatataaa
agaatgacttttttttGGttacattttaacttttagctttCCacgtaattaatttagcgctacttttcaattacaaat
tctgctttattaaatctGGttaatgatatttgaaaaattttaatttgtgaGGcaaattttaGGttaagatactcgaa
gagtttttcttaagatagttcacataaGGttttgcaaaagttGGGagaaattgttatatttgaactagCCCtatttc
tagcttatgtatgaatttgaaataataatttaactatcaaattaattatgtatacaagataactcgaataattt
gtatatagattatctctaacagatgCCttgtaGGGtattaaatttgCCtgcaaGGctttttCCagtttgttttctgt
ataataatatgtagcatGGcatctattCCctttttttaataaatatctattcataatcagacgtctaaaattcgaata
cttttcttgataatatcgtcttactCCttaattagtaagttgtgttgtcattaaatat

*Solyc01g066970* locus (ORF): SEQ ID NO: 7 (5'→3')

atgtctGGtgtttGGGtattcaagaatGGagtagtgaGGctagttgaggaaCCCCGGtgacttCCacGGtgcgacGGG
tcgtcgtaaagtgcttgtgcaCCtttctagtaatgaagtaataacatcatatgcagtacttgaaaGGaaactgtact
ctcttGGatGGGagaGGtactatgatgaCCCtgaCCttcttcaattCCataaaagatcaactgttcatcttatttct
ctaCCaaaGGacttcaacaaCCtcaagtCCatgcacatgtatgatattgttgttaagaatcgtaatgagtttacagt
taGGGatatgtag

*Solyc01g066970* locus (encoded amino acid sequence): SEQ ID NO: 8
MSGVWVFKNGVVRLVENPGDFHGATGRRKVLVLHLSSNEVITSYAVLERKLYSLGWERYYDDPDLLQFHKRSTVHLIS
LPKDENNLKSMHMYDIVVKNRNEFTVRDM

*Solyc01g066970* locus guide sequence #1: SEQ ID NO: 9 (5'→3')
tatggaattgaagaaggtca

*Solyc01g066970* locus guide sequence #2: SEQ ID NO: 10 (5'→3')
cggtgacttccacggtgcga

*Solyc06g005530* locus: SEQ ID NO: 11 (5'→3')
tttattagagatgtcatttgataatattttattatttcttcttcttattatttttGGttaagttatcttctttc
tttttttctctctttctatattttaCCatttaacgaaaataaataaataaattacttttatattttcaaaatgac
atagttgaaCCttatcaaGGtgtttaaaatataaaaagtctacttgaaatgcttttaaaagtgaaagtttatgttactt
ttaaGGatttgacgatgaattttagtatCCtaCCatatatttgaaacagcttgtctcatcattgtGGtacaaatgat
aagataaatatttttttttgtttttgtttttcatCCGGtgttcgatatcaacaatGGaaCCCaataatattcaga
ttcttacgaaacgtCCtacatctgaGGGtaaaatactCCttaacagagatgactCCatagttagagaGGataaataa
tctcaagatcactaaattaatatCCCtaaCCaaatacaagataaaatgtgtCCCacaattataactCCCtatatCCC
actttatacgacactttcagatttcgacattcaaacaattctatttttttaCCgtaaaaaatatcatatcttgaatt
atcaatacaaatatataatttcatttaatttttaaaaaagattCCattagtaaattttcaattaagcttaaactaaa
cagaaaaaaaatatctcttatCCatcgtaCCaaacgacaCCagaacataaaaattaaaaaaCCtagaaagtaaatga
actagtatCCCaaaaaGGttaatagtagtCCagtcattcaaaagatcagtgatcacatgatgtactagcaaaCCtac
atacacagtGGaatatatctactgctCCataagaaattatttcatcatttctctaagagttatgaattattttatta
ttatttttctttctCCatctCCatatattgttGGagttGGaaactaatataaagtaaattaaaCCattatattataa
tgtctGGcgtatGGatatttgacaagaaaGGtgttgCCCatttgatcaaaaatCCtactcgtgaatCCttcgagcta
aaacaaCCaacacatCCaGGtatgtcactcgataagtttaactcattcgattcagtaattaatactacacatt
ctCCtttgacgatatatGGagactacactatatattatatgtgtttatgtttttatgtatttgttaGGGGttaatt
agtCCgttacatgctgattgcagtaatagagttaGGtttttcattaagaaaaatcaaaattaaaaaaatatgtaaata
tagaaaaaaaaatcaaGGtgattcaaaaaGGagttgtaatctcacgtatatatagtgaaatttatttctaaGGaGGtt
tgaatatcgaaaCCtagttgcaCCCataattacaaCCtttaattttGGatcgtgacagatatgatattagaacatag
tttattGGtttcaacaaGGaattgacaacataagctttaagtcaaGGcaaaatgtatatattatcttCCttcatgac
atttgtactcgtactgactctaaattctgtattcgtCCttgtaGGcacGGGtacagCCacagcaCCGGGGGcacgC TABLE 1-continued CRISPR modification of tomato plants - sequences (underlined sequence = open reading frame; dotted underline sequence = intron; boxed sequence = CRISPR target sequence; bold capital letters = zCas9 PAM sites). It is understood that RNA equivalents of the listed DNA sequences, substituting uracils (U) for thymines (T), may be used.

CCtcgagtgttGGtgtaCCtaCCagagaatgagatgataGGttCCtatgaagaactagagaagagactcattgaaat cGGGtGGaCCCgattcaacaaCCCgatgaagtcGGatcttctgcagtttcataaatcagatgattctgcacatctca tttcacttCCaaagagctttacaaacttcaactcacacaatatgtatgacattgtGGtcaagaatCCatcGGttttt gaagttcgtgatgttaaagtgtgtgatcatcttatatgaaacttaaattattaaagtaaacatacgtaattatgtta tttctCCtctttcgtatctgagcttgattctttttcattagCCaaatacgtGGatttatatgtttttcgctctttG
GttGGtGGagagatttGGaaCCtagctagcatatctcgtgCCtattctgataacatattgaattgtatacatgatcg
tttcatctaaaaattaagcatttaaaaatcacattttaattacttaactaattatatagttatattatgtgttaac
acataCCttgcatatatgagtttgattcttcttcatgaCCagaaaatgtcaaatatattttgctttttgagCCGGa
actcttacatgctCCatttgataacaagttGGaatgtgtGGttatcttatataaaaacaacacaagttgttatgaaa
agcatatttataattattaatctaattatattatgttttaacacagtttttatatgtgaatttgattctttttcat
tGGGcaaacatgtgtgaaacaatttatttttttatagactaGGatgatagagaaatttgaacttaaaatctctcatg
tgttcgaataacatattataaagtatgctatcattcatttaaaatttaacttattagaaaataatacacttttttt
acttaattataatgtgactcttcgttttGGCCataataaaagtctatttgaattgattttgacttttgattttcaa
gtcaatgtttgaattatttttgatgtttttagcttaaagcaaatGGtttgtgcgtCCaaaaaatatttgaaactatt
ttaacttaaaatcacttaaaacaagtcgatCCatgtaacatgcaagttttgaCCtaattagaaGGtttgaaattata
CCtagctagagctatctatttcttttattatcaatttttttaatatatcatagttctatattaatatttttttgctt
tctcgata

*Solyc06g005530* locus (ORF): SEQ ID NO: 12 (5'→3')
atgtctGGcgtatGGatatttgacaagaaaGGtgttgCCCatttgatcaaaaatCCtactcgtgaatCCttcgagct
aaaacaaCCaacacatCCaGGtatatgtcactcgatataagtttaactcattcgattcagtaattaatactacacat
tctCCtttgacgatatatGGagactacactatatattatatgtgttttatgtttttatgtatttgttaGGGGttaat
tagtCCgttacatgctgattgcagtaatagagttaGGtttttcattaagaaaaatcaaaattaaaaaatatgtaaat
atagaaaaaaaatcaaGGtgattcaaaaaGGagttgtaatctcacgtatatatagtgaaatttatttctaaGGaGGt
ttgaatatcgaaaCCtagttgcaCCCataattacaaCCtttaattttGGatcgtgacagatatgatattagaacata
gtttattGGtttcaacaaGGaattgacaacataagctttaagtcaaGGcaaaatgtatatattatcttCCttcatga
cattttgtactcgtactgactctaaattctgtattcgtCCttgtaGGcacGGGtacagCCacagcaCCGGGGGcacg
CCCtcgagtgttGGtgtaCCtaCCagagaatgagatgataGGttCCtatgaagaactagagaagagactcattgaaa
tcGGGtGGaCCCgattcaacaaCCCgatgaagtcGGatcttctgcagtttcataaatcagatgattctgcacatctc
atttcacttCCaaagagctttacaaacttcaactcacacaatatgtatgacattgtGGtcaagaatCCatcGGtttt
tgaagttcgtgatgttaaagtgtgtgatcatcttatatga

*Solyc06g005530* locus (encoded amino acid sequence): SEQ ID NO: 13
MSGVWIFDKKGVAHLIKNPTRESFELKQPTHPGTGTATAPGARPRVLVYLPENEMIGSYEELEKRLIEIGWTRENNP
MKSDLLQFHKSDDSAHLISLPKSFTNENSHNMYDIVVKNPSVFEVRDVKVCDHLI

*Solyc06g005530* locus guide sequence #1: SEQ ID NO: 14 (5'→3')
agagactcattgaaatcggg

*Solyc06g005530* locus guide sequence #2: SEQ ID NO: 15 (5'→3')
Agaagagactcattgaaatc

*Solyc06g005530* locus guide sequence #3: SEQ ID NO: 76 (5'→3')
Gagaagagactcattgaaat

*Solyc06g005530* locus guide sequence #4: SEQ ID NO: 77 (5'→3')
Gggggcacgccctcgagtgt

*Solyc06g005530* locus guide sequence #5: SEQ ID NO: 78 (5'→3')
Ggtaggtacaccaacactcg

*Solyc06g005530* locus guide sequence #6: SEQ ID NO: 79 (5'→3')
Aacactcgagggcgtgcccc

*Solyc06g005530* locus guide sequence #7: SEQ ID NO: 80 (5'→3')
Gggtacagccacagcaccgg

*Solyc06g005530* locus guide sequence #8: SEQ ID NO: 81 (5'→3')
cgggtacagccacagcaccg

*Solyc06g005530* locus guide sequence #9: SEQ ID NO: 82 (5'→3')
Acgggtacagccacagcacc

*Solyc06g005530* locus guide sequence #10: SEQ ID NO: 83 (5'→3')
Cacgggtacagccacagcac

*Solyc06g005530* locus guide sequence #11: SEQ ID NO: 84 (5'→3')
Agggcgtgccccggtgctg TABLE 1-continued CRISPR modification of tomato plants - sequences (underlined sequence = open reading frame; dotted underline sequence = intron; boxed sequence = CRISPR target sequence; bold capital letters = zCas9 PAM sites). It is understood that RNA equivalents of the listed DNA sequences, substituting uracils (U) for thymines (T), may be used.

*Solyc06g005530* locus guide sequence #12: SEQ ID NO: 85 (5'→3')
Tgtattcgtccttgtaggca

*Solyc06g005530* locus guide sequence #13: SEQ ID NO: 86 (5'→3')
Aattctgtattcgtccttgt

*Solyc06g005530* locus guide sequence #14: SEQ ID NO: 87 (5'→3')
Tggctgtacccgtgcctaca

*Solyc06g005530* locus guide sequence #15: SEQ ID NO: 88 (5'→3')
Acgagtacaaaatgtcatga

*Solyc06g005530* locus guide sequence #16: SEQ ID NO: 89 (5'→3')
Acaacataagctttaagtca

*Solyc06g005530* locus guide sequence #17: SEQ ID NO: 90 (5'→3')
ttgtaattatgggtgcaact

*Solyc06g005530* locus guide sequence #18: SEQ ID NO: 91 (5'→3')
Agtaggatttttgatcaaat

*Solyc06g005530* locus guide sequence #19: SEQ ID NO: 92 (5'→3')
aaccattatattataatgtc

*Solyc12g099610* locus: SEQ ID NO: 16 (5'→3')
aagttttgaattctttaGGttgcttttctttaatttttttcttcttctcatatcatgaatcttatCCatttcaata
tttCCaCCaaacatGGGacatGGacatctctatgagttcatcttcttgcttCCaatgcattatctGGtgtttgatat
tcgtattgagcttCCactaattcagattcatgCCgcataaagtctatttaaaagaaaaatatttctatcaaaattgt
tttcatactctaGGGtcgagcaaaGGGattcatgaCCaatgatatctacGGGaatattaaagaatcttgataaagaa
cacttctCCttgtCCgagCCtttgacaaaaatcattttGGtaGGattgcttCCCCaCCtttcagtcttatgtagaa
tttgaattagttgagattcactatgaatatcgaataaataacaaaaaaaaaaaGGagtaatgaatctttCCaaatat
agaatatattatgattaaatgcatgcatGGGaagcaaaaagatgaacttatGGagatgtgtcatgtCCCatatattt
gatGGaaatattGGGttGGataagattcatgatgaaaaaaaaaagcGGtgacataaatctgaattagtcGGaactCC
aaatagtttaatttgtttttgaaaaataaCCttcttttacttgCCCtttCCtttttttatctcttcaaaaaataaaaa
taaaacttcttaCCacaatttatactatatattacttattaaGGGGaatcttgatgcaataacataacacagttatc
tttatcagattcgaaCCgtagaagcagctacaaatatttgtaataaGGaaGGctatttacatcacacatgtatttat
acgtatatGGacttatttatttatttatatatatatatatatatatatgcatatcacaCCatgcattaaCCCtataa
aaCCCacacattatattctttttcaacaacaCCatcttttacatatattcaacttCCCCtCCCtctatCCCtcatca
tgtcaGGtgtttGGattttcaaaaacGGcgtcgtCCGGctagaaaCCCCCGGtgactgCCacgtcagctCCacgaCC
GGtcatcGGaaagttctagtacatgttCCtagtaaagaagtcattacatgttatgcaaatcttgaaaaaaagcttta
tagtcttGGatGGGaaaGGtattatgatgatCCacaacttcttcaataCCacaaaagatCCacaattcatcttattt
CCCtCCCaattgattttaataGGtttaaatCCattcatatgtatgatattgttgttaaaaatcgaaatgaatttgaa
gttagagatatgtaaagttactaactttctttacgtGGatataagaaatgtgaaatttGGagaaacttatgtgtttt
cgagttgatagtgatatgtttGGagattGGagttgtgtttgaacatGGatacgaacGGaattgtttttgaatttttg
aaagtgaaaattgctttttattgtttttgaacttaaaattgttatgtGGctaacaaaataaaatcaatcaacaaaca
agtcgttgtagtatagtGGtaagtattCCCgCCtgtcacgcGGGtgaCCCGGGttcgatCCCCGGcaacGGcgttaa
ttttttttatgtttctacacataCCatatatctagttatatcttacgacaagcacaaatacattatgctctcgcaac
atacaatgtatctagttatatatcttacgagaagcacaaatacattatgctctcgcaacatacaatatatCCagttg
tgtcttacgacaagtactCCaaaaCCCaCCaacgctcgagaaatgCCttgttatGGtgtaagaaacatcagcttcag
tatgttaagactgataacaaaGGagttacttcacaagttctttttcaacaagtaatttacatagagtttGGatgttg
tgttctGGacaacaagaaaaaatgaatgtagttagtctaaGGctatgttgcttGGactctCCaaaagatgctacaCC
CgtgtcGGGtCCtCCaaaaatgcactactttgaaGGatcagacatgcacgtgtcgCCatatttcaagagCCCgagc
aacataGGttcaaGGaactcatatgatataGGctaatgtcacgaactcactttcttctttgtcgtgctCCaaatgtt
tcagctctgaaCCtatacattCCgCCatCCaatatatctCCtcagtCCgcGGGtgagacttgtcatCCgat

*Solyc12g099610* locus (ORF): SEQ ID NO: 17 (5'→3')
atgtcaGGtgtttGGattttcaaaaacGGcgtcgtCCGGctagaaaCCCCCGGtgactgCCacgtcagctCCacgaC
CGGtcatcGGaaagttctagtacatgttCCtagtaaagaagtcattacatgttatgcaaatcttgaaaaaaagcttt
atagtcttGGatGGGaaaGGtattatgatgatCCacaacttcttcaataCCacaaaagatCCacaattcatcttatt
tCCCtCCCaattgattttaataGGtttaaatCCattcatatgtatgatattgttgttaaaaatcgaaatgaatttga
agttagagatatgtaa

*Solyc12g099610* locus (encoded amino acid sequence): SEQ ID NO: 18
MSGVWIFKNGVVRLETPGDCHVSSTTGHRKVLVHVPSKEVITCYANLEKKLYSLGWERYYDDPQLLQYHKRSTIHLI
SLPIDENRFKSIHMYDIVVKNRNEFEVRDM

*Solyc12g099610* locus guide sequence #1: SEQ ID NO: 19 (5'→3')
ccctcatcatgtcaggtgtt

*Solyc12g099610* locus guide sequence #2: SEQ ID NO: 20 (5'→3')
ttttcaaaaacggcgtcgtc TABLE 1-continued CRISPR modification of tomato plants - sequences (underlined sequence = open reading frame; dotted underline sequence = intron; boxed sequence = CRISPR target sequence; bold capital letters = zCas9 PAM sites). It is understood that RNA equivalents of the listed DNA sequences, substituting uracils (U) for thymines (T), may be used.

*Solyc12g099610* locus guide sequence #2: SEQ ID NO: 93 (5'→3')
Agtcaccgggggtttctagc

*Solyc12g099610* locus guide sequence #2: SEQ ID NO: 94 (5'→3')
Gtcgtccggctagaaacccc

*Solyc12g099610* locus guide sequence #2: SEQ ID NO: 95 (5'→3')
Agctgacgtggcagtcaccg

*Solyc12g099610* locus guide sequence #2: SEQ ID NO: 96 (5'→3')
Gagctgacgtggcagtcacc

*Solyc12g099610* locus guide sequence #2: SEQ ID NO: 97 (5'→3')
Gaccggtcgtggagctgacg

*Solyc12g099610* locus guide sequence #2: SEQ ID NO: 98 (5'→3')
Aactttccgatgaccggtcg

*Solyc12g099610* locus guide sequence #2: SEQ ID NO: 99 (5'→3')
Gatgaattgtggatcttttg

*Solyc12g099610* locus guide sequence #2: SEQ ID NO: 100 (5'→3')
Gagggaaataagatgaattg

*Solyc12g099610* locus guide sequence #2: SEQ ID NO: 101 (5'→3')
Ccctoccaattgattttaat

*Solyc01g066980* locus: SEQ ID NO: 21 (5'→3') (*br* locus)
atgtctGGagtttGGGtattcaagaatGGtgttgtCCgtctagtGGagaactCCgattgCCacGGGGcgaacGGact
CCgaaaagttcttgtacatcttCCtagtaatgaagtcatcacatcatatgcagtacttgaaaGGaaactgtactctc
ttGGatGGGagaGGtactatgatgaaCCtgaacttcttcaataCCacaaaagatcaaCCgttcatcttatttctcta
CCaaaGGatttcaacaGGttcaaatCCatgcatatgttcgatatcgtcgtcaagaatcgcaatgaatttgaGGttag
agatatg

*Solyc01g066980* locus (amino acid sequence): SEQ ID NO: 22
MSGVWVFKNGVVRLVENSDCHGANGLRKVLVHLPSNEVITSYAVLERKLYSLGWERYYDEPELLQYHKRSTVHLISL
PKDFNRFKSMHMFDIVVKNRNEFEVRDM

*Solyc01g066980* locus: SEQ ID NO: 102
catctcatcataaactacaaacacatacaaaaaacattctcattcaCCtttCCtctacaaaaaacataacaacatct
tcaacaatcatgtctGGagtttGGGtattcaagaatGGtgttgtCCgtctagtGGagaactCCgattgCCacGGGGc
gaacGGactCCgaaaagttcttgtacatcttCCtagtaatgaagtcatcacatcatatgcagtacttgaaaGGaaac
tgtactctcttGGatGGGagaGGtactatgatgaaCCtgaacttcttcaataCCacaaaagatcaaCCgttcatctt
atttctctaCCaaaGGatttcaacaGGttcaaatCCatgcatatgttcgatatcgtcgtcaagaatcgcaatgaatt
tgaGGttagagatatgtaaacaaaatatGGGGgaaaaaaGGGaaGGagttgatcatttgaatgtgtttttttttctt
ttttttgcttttttttGGtcaagtgtgttgtaattaagtttctatcgtttaatttgtgatttgtttcacaatgttgc
taaGGttgtaatttGGaaagttgtaagaGGGGaaatgttgtatattattacaagtgaatgtgttttattatatgata
tatatatatataagag

TABLE 2

(part A). Brachytic loci homologs, amino acid sequence alignment part 1 (sequences are continued in parts B-F).

| | |
|---|---|
| Niben101Scf00012g00011.1 | MSGVWIFDKKGVARLITNPT |
| Peaxi162Scf00056g00139.1 | MSGVWIFDKKGVAHLIKNPT |
| Peinf101Scf01105g01005.1 | MSGVWIFDKKGVAHLIKNPT |
| Capana06g002723 | MSGVWIFDKKGVAHLIKNPT |
| Capang06g002516 | MSGVWIFDKKGVAHLIKNPT |
| Capang05g001509 | GTG |
| SMEL 006g247790.1.01 | MSGVWIFDKKGVAHLIKNPT |
| PGSC0003DMP400007817 | MSGVWIFDKKGVAHLIKNPT |

TABLE 2-continued

| | |
|---|---|
| Sopen06g001510.1 | MSGVWIFDKKGVAHLIKNPT |
| Solyc06g005530.2.1 | MSGVWIFDKKGVAHLIKNPT |
| Niben101Scf05107g01003.1 | MSGVWLSKNTGVIRLLENQTE |
| Peinf101Scf02016g05027.1 | MSGVWVF-KNGVERLVENPG |
| Peaxi162Scf00078g00059.1 | MSGVWVF-KNGVFRLVENPG |
| SMEL 012g387130.1.01 | MSGVWVF-KNGVFRLVENG |
| Capana10g001758 | MSGVWVF-KNGVERLVENG |
| CA05g11610 | LIFEKEHTHTHTSEVEMSGVWVF-KNGVERLVENG |
| Niben101Scf05041g04001.1 | MSGVWVF-KNGVERLVENP |
| Niben101Scf02182g12004.1 | MSGVWVF-KNGVERLVENP |
| Sopen01g028590.1 | MPGVWEI-KNGVVRLVEKPG |
| Niben101Scf13863g00010.1 | MSGVWVF-KNGVLRLVENPG |
| SMEL 001g140830.1.01 | MSGVWVF-KNGVVRLVENTG |
| Capana01g003223 | MSGVWVF-KNGVVRLVEN-G |
| Solyc01g066980.3.1 | SHHKLQTHTKNILIHLSSTKNITTSSTIMSGVWVF-KNGVVRLVENS |
| Sopen01g028640.1 | MSGVWVF-KNGVVRLVENS |
| Sopim01g066980.0.1 | MSGVWVF-KNGVVRLVENS |
| PGSC0003DMP400020089 | MSGVWVF-KNGVVRLVENS |
| Niben101Scf10524g05008.1 | MSGVWVF-KNGVVRLE |
| Peaxi162Scf00534g00012.1 | MSGVWVF-KNGVVRLVENPG |
| Peinf101Scf01113g00005.1 | MSGVWVF-KNGVVRLVENPG |
| Peaxi162Scf00086g00036.1 | MSGVWVF-KNGVLRLVENPGDNYHG |
| Peinf101Scf00973g06042.1 | MSGVWVF-KNGVLRLVENPGDNYHG |
| Capana01g003222 | MSGVWVF-KNGVVRLVENPG |
| Peaxi162Scf00534g00005.1 | MSGVWVF-KNGVVRLVENPG |
| Peinf101Scf01113g00004.1 | MSGVWVF-KNGVVRLVENPG |
| SMEL 001g140850.1.01 | MSGVWVF-KNGVVRLVENPG |
| Niben101Scf02626g03001.1 | MSGVWVF-KNGVVRLVENPG |
| Niben101Scf10524g05006.1 | MSGVWVF-KNGVVRLVENPG |
| Solyc01g066970.2.1 | MSGVWVF-KNGVVRLVENPG |
| Sopen01g028630.1 | MSGVWVF-KNGVVRLVENPG |
| PGSC0003DMP400020088 | MSGVWVF-KNGVVRLVENAG |
| Sopen01g028610.1 | MSGVWKI-KNGVVRLVENLG |
| Solyc01g066950.1.1 | MSGVWKI-KNGVVRLVENLG |
| Capana12g000135 | MSGVWTF-KNGVVRL-ENRG |
| Capang12g000108 | VS |
| SMEL 005g240480.1.01 | MSGVWVF-KNGVVRL-ENPG |
| Solyc12g099610.1.1 | MSGVWIF-KNGVVRL-ETPG |
| PGSC0003DMP400008206 | MSGVWIF-KNGVVRL-ENPG |

TABLE 2-continued

| (part B). Brachytic loci homologs, amino acid sequence alignment part 2. | |
|---|---|
| Niben101Scf00012g00011.1 | |
| Peaxi162Scf00056g00139.1 | |
| Peinf101Scf01105g01005.1 | |
| Capana06g002723 | |
| Capang06g002516 | |
| Capang05g001509 | |
| SMEL 006g247790.1.01 | |
| PGSC0003DMP400007817 | |
| Sopen06g001510.1 | |
| Solyc06g005530.2.1 | |
| Niben101Scf05107g01003.1 | |
| Peinf101Scf02016g05027.1 | |
| Peaxi162Scf00078g00059.1 | |
| SMEL_012g387130.1.01 | |
| Capana10g001758 | |
| CA05g11610 | |
| Niben101Scf05041g04001.1 | |
| Niben101Scf02182g12004.1 | |
| Sopen01g028590.1 | |
| Niben101Scf13863g00010.1 | |
| SMEL_001g140830.1.01 | |
| Capana01g003223 | |
| Solyc01g066980.3.1 | |
| Sopen01g028640.1 | |
| Sopim01g066980.0.1 | |
| PGSC0003DMP400020089 | |
| Niben101Scf10524g05008.1 | |
| Peaxi162Scf00534g00012.1 | |
| Peinf101Scf01113g00005.1 | |
| Peaxi162Scf00086g00036.1 | SRKVLVHVPSDEVITSYAILERKLYNLGWERYYDDPNLLQYHKRSTVHLISLPR |
| Peinf101Scf00973g06042.1 | SRKVLVHVPSNEVVTSYAILERKLYNLGWERYYDDPNLLQYHKRSTVHLISLPR |
| Capana01g003222 | |
| Peaxi162Scf00534g00005.1 | |
| Peinf101Scf01113g00004.1 | |
| SMEL 001g140850.1.01 | |
| Niben101Scf02626g03001.1 | |
| Niben101Scf10524g05006.1 | |
| Solyc01g066970.2.1 | |
| Sopen01g028630.1 | |

TABLE 2-continued

| | |
|---|---|
| PGSC0003DMP400020088 | |
| Sopen01g028610.1 | |
| Solyc01g066950.1.1 | |
| Capana12g000135 | |
| Capang12g000108 | |
| SMEL 005g240480.1.01 | |
| Solyc12g099610.1.1 | |
| PGSC0003DMP400008206 | |
| (part C). Brachytic loci homologs, amino acid sequence alignment part 3. | |
| Niben101Scf00012g00011.1 | RESFDLMQPTSSGTGT--APGARPKVLVYLPENQ |
| Peaxi162Scf00056g00139.1 | RESFELKEPTYPGTGTATAPGARPKVLVYLPENE |
| Peinf101Scf01105g01005.1 | RESFELNEPTYPGTGTATAPGARPKALVYLPENE |
| Capana06g002723 | RESFELKOPAYPGTGTATAPGARPRVLVYLPENE |
| Capang06g002516 | RESFELKQPAYPGTGTATAPGARPRVLVYLPENE |
| Capang05g001509 | TAT--APGARPRVLVYLPENE |
| SMEL_006g247790.1.01 | RESFELKQSTYPGTGTATAPGARPRVLVYLPENE |
| PGSC0003DMP400007817 | RESFELKQPTYPGTGTVTAPGARPRVLVYLPENE |
| Sopen06g001510.1 | RES FELKQPTHPGTGTATAPGARPRVLVYLPENE |
| Solyc06g005530.2.1 | RESFELKQPTHPGTGTATAPGARPRVLVYLPENE |
| Niben101Scf05107g01003.1 | EEQ--SIGRKRKVLVHLPTQE |
| Peinf101Scf02016g05027.1 | AEQ---AQRRRKVLVHLPTGQ |
| Peaxi162Scf00078g00059.1 | AEQ---AQRRRKVLVHLPTGQ |
| SMEL 012g387130.1.01 | SGD--QAQRRRKVLIHLPSGQ |
| Capana10g001758 | SGD--QAQRRRKVLLHLPSGQ |
| CA05g11610 | SGD--QAQRRRKVLLHLPSGQ |
| Niben101Scf05041g04001.1 | SSE--QGQRRRKVLVHLPTGQ |
| Niben101Scf02182g12004.1 | SSE--QGQRRRKVLLHLPTGQ |
| Sopen01g028590.1 | DSH--GATVRNKVLVHLSSNE |
| Niben101Scf13863g00010.1 | DHF----QGCRKVLVHIPTNE |
| SMEL_001g140830.1.01 | DCQ--GANGGRKVLVHVPSDE |
| Capana01g003223 | DCQ--GVNGCRKVLVHLASGE |
| Solyc01g066980.3.1 | DCH--GANGLRKVLVHLPSNE |
| Sopen01g028640.1 | DCH--GANGLRKVLVHLPSNE |
| Sopim01g066980.0.1 | DCH--GANGLRKVLVHLPSNE |
| PGSC0003DMP400020089 | DCH--GANGLRKVLVHLPSDE |
| Niben101Scf10524g05008.1 | DCQ--GSSGRRKVLVHVPSNE |
| Peaxi162Scf00534g00012.1 | DCQ--GSSGRRKVLVHVPTNE |
| Peinf101Scf01113g00005.1 | DCQ--GSSGRRKVLVHVPTNE |
| Peaxi162Scf00086g00036.1 | DFSKLKTMHMYDIVVKNRNEFESNGVVRLENPSDYH--GSAGRRKVLVHAASNE |
| Peinf101Scf00973g06042.1 | DFSKFKTMHMYDIVVKNRNEFESNGVVRLENPGDYH--GSSGRRKVLVHATSNE |

TABLE 2-continued

| | |
|---|---|
| Capana01g003222 | DCH--GATGRRKVLVHLASNE |
| Peaxi162Scf00534g00005.1 | DFH--GSSGRRKVLVHVPSNE |
| Peinf101Scf01113g00004.1 | DFH--GSTGRRKVLVHVPSNE |
| SMEL_001g140850.1.01 | DFH--GSTGRRKVLVHLPSNE |
| Niben101Scf02626g03001.1 | DCH--GATGRRKVLVHLSSNE |
| Niben101Scf10524g05006.1 | DCH--GATGRRKVLVHLSSNE |
| Solyc01g066970.2.1 | DFH--GATGRRKVLVHLSSNE |
| Sopen01g028630.1 | DFH--GATGRRKVLVHLSSNE |
| PGSC0003DMP400020088 | DFH--GATGRRKVLVHLSSNE |
| Sopen01g028610.1 | DFQ--GATGRRKVLVHLSSNE |
| Solyc01g066950.1.1 | DFH--GATGRRKVLVHLSSNE |
| Capana12g000135 | DCHVSATTGRRKVLVHVASDE |
| Capang12g000108 | ATAGRRKVLVHVASDE |
| SMIEL 005g240480.1.01 | DCHVSSTTSRRKVLVHVPSNE |
| Solyc12g099610.1.1 | DCHVSSTTGHRKVLVHVPSKE |
| PGSC0003DMP400008206 | DCHVSSTTGHRKVLVHVPSNE |

(part D). Brachytic loci homologs, amino acid sequence alignment part 4.

| | |
|---|---|
| Niben101Scf00012g00011.1 | VISSYADLEKILIELGWSRYNNPIRLDFMQFHKSDDSAHL-ISLPKEFTNFKSL |
| Peaxi162Scf00056g00139.1 | VISSYDELEKILVELGWSRYNNPTRSDLLQFHKSDDSAHL-ISLPISFTNFKPL |
| Peinf101Scf01105g01005.1 | VISSYDELEKILIELGWSRYNSPTRSDLLQFHKSNDSGHL-ISLPISFTNFKPL |
| Capana06g002723 | MISSYEELERRLIELGWTRENNPMRSDLLQFHKSDDSAHL-ISLPKSFTDFKSL |
| Capang06g002516 | MISSYEELERRLIELGWTRENNPMRSDLLOFHKSDDSAHL-ISLPKSFTNEKSL |
| Capang05g001509 | MISSYEELERRLIELGWTRENNPMRSDLLQFHKSDDSAHL-ISLPKSFTNFKSL |
| SMEL 006g247790.1.01 | IISSYEELERRLIELGWTRENNPMKSDLLQFHKSDDSAHL-ISLPKSFTNFKSL |
| PGSC0003DMP400007817 | MISSYEELEKRLIELGWTRENNPMKSDLLQFHKSDDSAHL-ISLPKSFTNFKSH |
| Sopen06g001510.1 | MIGSYEELEKRLIEIGWTRENNPMKSDLLQFHKSDDSAHL-ISLPKSFTNFNSH |
| Solyc06g005530.2.1 | MIGSYEELEKRLIEIGWTRENNPMKSDLLQFHKSDDSAHL-ISLPKSFTNENSH |
| Niben101Scf05107g01003.1 | IVSSYNSLDKILTDLGWEKYDCGDDPHFYQFHKRT-PIHLSLSLPNDFAKFNTV |
| Peinf101Scf02016g05027.1 | MVSSYCSLERILNGLGWERV |
| Peaxi162Scf00078g00059.1 | MVSSYCSLERILNGLGWERYYGG-DPELFQFHKHS-SIDL-ISLPKDFSKENSI |
| SMEL_012g387130.1.01 | VVSSYCSLERILNDLGWERYYEG-DAELFQFHKHS-SIDL-ISLPMDFTKENSI |
| Capana10g001758 | VVSSYCSLERILNGLGWERYYGG-DTELFQFHKHS-SIDL-ISLPKDFAKENSI |
| CA05g11610 | VVSSYCSLERILNGLGWERYYGG-DTELFQFHKHS-SIDL-ISLPKDFAKFNSI |
| Niben101Scf05041g04001.1 | VVSSYCSLERILKGLGWERYYGG-DPELFQFHKHS-SIDL-ISLPKEFAKENSI |
| Niben101Scf02182g12004.1 | VVSSYCSLERILNGLGWERYYGG-DPELFQFHKHS-SIDL-ISLPKDFAKFNSI |
| Sopen01g028590.1 | VITSYASLERILISIGWERYYDG-DPDLLQYHKRS-TVHI-ISLPKDFKNFKFP |
| Niben101Scf13863g00010.1 | VITSYAILETKLYNLGWERYYD--DPELLQYHKRC-TTHL-ISLPKDENKFKTM |
| SMEL_001g140830.1.01 | VITSYAVLERKLYSLGWERYYD--DPDLLQYHKRS-TVHL-ISLPKDENRFKSM |
| Capana01g003223 | VITSYAVLERKLYSLGWERYYD--EPELLQYHKRS-TVHL-ISLPKDENRFKSM |
| Solyc01g066980.3.1 | VITSYAVLERKLYSLGWERYYD--EPELLQYHKRS-TVHL-ISLPKDFNRFKSM |

TABLE 2-continued

| | |
|---|---|
| Sopen01g028640.1 | VITSYAVLERKLYSLGWERYYD--EPELLQYHKKS-TVHL-ISLPKDENRFKSM |
| Sopim01g066980.0.1 | VITSYAVLERKLYSLGWERYYD--EPELLQYHKRS-TVHL-ISLPKDENRFKSM |
| PGSC0003DMP400020089 | VITSYAVLERKLYSLGWERYYD--EPELLQYHKRS-TVHL-ISLPKDENRFKSM |
| Niben101Scf10524g05008.1 | VITSYPVLERKLYSLGWERYYD--DLNLLQYHKRS-TVHL-ISLPKDENKFKSM |
| Peaxi162Scf00534g00012.1 | VITSYALLERKLYSLGWERYYD--DPDLLQYHKRS-TVHL-ISLPKDENKEKSI |
| Peinf101Scf01113g00005.1 | VITSYALLERKLYSLGWERYYD--DPDLLQYHKRS-TVHL-ISLPKDENKEKSI |
| Peaxi162Scf00086g00036.1 | VITSYATLERKLYNLGWERYYD--DPELLQYHKRS-TVHL-ISLPKDFSRFKSM |
| Peinf101Scf00973g06042.1 | VITSYATLERKLYNLGWERYYD--DPELLQYHKRS-TVHL-ISLPKDFSRFKSM |
| Capana01g003222 | VISSYASLERKLYSLGWERYYD--DPDLLQYHKRS-TVHL-ISLPKDENRFKSM |
| Peaxi162Scf00534g00005.1 | VISSYATLERKLSSLGWERYYD--DPDLLQYHKRS-TVHL-ISLPKDENRFKSM |
| Peinf101Scf01113g00004.1 | VISSYATLERKLSSLGWERYYD--DPDLLQYHKRS-TVHL-ISLPKDENRFKSM |
| SMEL_001g140850.1.01 | VITSYAALERKLYSLGWERYYD--DPDLLQYHKRS-TVHL-ISLPKDENRFKSM |
| Niben101Scf02626g03001.1 | VITSYSALERKLYSLGWERYYD--DPDLLQYHKRS-TVHL-ISLPKDENKFKSM |
| Niben101Scf10524g05006.1 | VITSYSALERKLYSLGWERYYD--DPDLLQYHKRS-TVHL-ISLPKDENRFKSM |
| Solyc01g066970.2.1 | VITSYAVLERKLYSLGWERYYD--DPDLLQFHKRS-TVHL-ISLPKDENNLKSM |
| Sopen01g028630.1 | VITSYASLERILFSLGWERYYD--DPDLLQFHKRS-TIHL-ISLPKDENNFKSM |
| PGSC0003DMP400020088 | VITSYASLERNLYSLGWERYYD--DPDLLQFHKRS-TVHL-ISLPKDENRFKSM |
| Sopen01g028610.1 | VITSYASLERILYSLGWERYYD--DPNLLQYHKRS-TVHL-ISLPKDENNLKSM |
| Solyc01g066950.1.1 | VITSYAVLERKLYSLGWERYYD--DPDLLQYHKRS-TVHL-ISLPNDENNLRSM |
| Capana12g000135 | VITCYENLERKLCNLGWERFKSM |
| Capang12g000108 | VITCYENLERKLCNLGWERYYD--DPQLLQYHKRS-TIHL-ISLPLDFTRFKSM |
| SMEL 005g240480.1.01 | VITCYENLERKLYSLGWERYYD--DPOLLOYHKRS-TIHL-ISLPMDENRFKSM |
| Solyc12g099610.1.1 | VITCYANLEKKLYSLGWERYYD--DPQLLQYHKRS-TIHL-ISLPIDENRFKSI |
| PGSC0003DMP400008206 | VITCYANLERKLYSLGWERYYD--DPQLLQYHKRS-TIHL-ISLPIDENRFKSI |

(part E). Brachytic loci homologs, amino acid sequence alignment part 5.

| | |
|---|---|
| Niben101Scf00012g00011.1 | HIE |
| Peaxi162Scf00056g00139.1 | HMYDIVVKNRSFFEVRDSPYTSY |
| Peinf101Scf01105g01005.1 | HMYDIVVKNRSFFEVRDSPYTSY |
| Capana06g002723 | HMYDIVVKNPSFFEVRNAEVDNHLI |
| Capang06g002516 | HMYDIVVKNPSFFEVRNAEVDNHLI |
| Capang05g001509 | HMYDIVVKNPSFFEVRNAEVDNHLI |
| SMEL_006g247790.1.01 | QMYDIVVKNPSFFEVRDIKVYDHPI |
| PGSC0003DMP400007817 | QMYDIVVKNPSIFEVRDVKVCDHLI |
| Sopen06g001510.1 | NMYDIVVKNPSVFEVRDVKVCDHLI |
| Solyc06g005530.2.1 | NMYDIVVKNPSVFEVR |
| Niben101Scf05107g01003.1 | QMYDIVFKTRHIFHVRYI |
| Peinf101Scf02016g05027.1 | QEIVLKYCVGIKLSH |
| Peaxi162Scf00078g00059.1 | HMYDIVVKNPNVFHVRDA |
| SMEL_012g387130.1.01 | HMYDIVVKNPNIFHVRDV |
| Capana10g001758 | HMYDIVVKNPNVFHVRDV |

TABLE 2-continued

| | |
|---|---|
| CA05g11610 | HMYDIVVKNPNVFHVRDV |
| Niben101Scf05041g04001.1 | HMYDIVVKNPNVFHVRDA |
| Niben101Scf02182g12004.1 | HMYDIVVKNPNVFHVRDV |
| Sopen01g028590.1 | HMLDIVLKNRNDFTTRDTSITNNN |
| Niben101Scf13863g00010.1 | HMYDIVVKNRNEFEVRDM |
| SMEL_001g140830.1.01 | HMYDIVVKNRNEFEVREM |
| Capana01g003223 | HMFDIVVKNRNEFEVRDM |
| Solyc01g066980.3.1 | HMFDIVVKNRNEFEVRDM |
| Sopen01g028640.1 | HMFDIVVKNRNEFEVRDM |
| Sopim01g066980.0.1 | HMFDIVVKNRNEFEVRDM |
| PGSC0003DMP400020089 | HMFDIVVKNRNEFEVRDM |
| Niben101Scf10524g05008.1 | HMYDIVVKNRNEFEVRDT |
| Peaxi162Scf00534g00012.1 | HMYDIVVKNRNEFEVRDK |
| Peinf101Scf01113g00005.1 | QMYDIVVKNRNEFEVRDK |
| Peaxi162Scf00086g00036.1 | HMYDIVVKNRNEFEVRDM |
| Peinf101Scf00973g06042.1 | HMYDIVVKNRNEFEVRD |
| Capana01g003222 | HMYDIVVKNRNEFEVRDI |
| Peaxi162Scf00534g00005.1 | HMYDIVVKNRNEFEVRDM |
| Peinf101Scf01113g00004.1 | HMYDIVVKNRNEFEVRDM |
| SMEL_001g140850.1.01 | HMYDIVVKNRNEFEVRDM |
| Niben101Scf02626g03001.1 | HMYDIVVKNRNEFEVRDM |
| Niben101Scf10524g05006.1 | HMYDIVVKNRNEFEVRDM |
| Solyc01g066970.2.1 | HMYDIVVKNRNEFTVRDM |
| Sopen01g028630.1 | HMYDIVVKNRNEFTVRDM |
| PGSC0003DMP400020088 | HMYDIVVKNRNEFEVRDM |
| Sopen01g028610.1 | HMYDIVVKNRNEFTVRDM |
| Solyc01g066950.1.1 | HMYDIVVKNRNEFAVRDM |
| Capana12g000135 | HMYDIVVKNRNEFEVRDMWATRSTALRCEVQVMMDQPEVCADALDK |
| Capang12g000108 | HMYDIVVKNRNEFEVRDM |
| SMEL 005g240480.1.01 | HMYDIVVKNRNEFEVRDM |
| Solyc12g099610.1.1 | HMYDIVVKNRNEFEVRDM |
| PGSC0003DMP400008206 | HMYDIVVKNRNEFEVRDM |

(part F). Brachytic loci homologs, amino acid sequence alignment part 6.

| | | | |
|---|---|---|---|
| Niben101Scf00012g00011.1 | *Nicotiana benthamiana* | Tobacco | SEQ ID NO: 29 |
| Peaxi162Scf00056g00139.1 | *Petunia axillaris* | White Petunia | SEQ ID NO: 30 |
| Peinf101Scf01105g01005.1 | *Petunia inflata* | Petunia | SEQ ID NO: 31 |
| Capana06g002723 | *Capsicum annuum Zunla* | Pepper | SEQ ID NO: 32 |
| Capang06g002516 | *Capsicum annuum Zunla* | Pepper | SEQ ID NO: 33 |
| Capang05g001509 | *Capsicum annuum* | Pepper (Chiltepin) | SEQ ID NO: 34 |
| SMEL 006g247790.1.01 | *Solanum melongena* | Eggplant | SEQ ID NO: 35 |

TABLE 2-continued

| | | | |
|---|---|---|---|
| PGSC0003DMP400007817 | *Solanum tuberosum* | Potato | SEQ ID NO: 36 |
| Sopen06g001510.1 | *Solanum pennellii* | Wild tomato | SEQ ID NO: 37 |
| Solyc06g005530.2.1 | *Solanum lycopersicum* | Tomato | SEQ ID NO: 38 |
| Niben101Scf05107g01003.1 | *Nicotiana benthamiana* | Tobacco | SEQ ID NO: 39 |
| Peinf101Scf02016g05027.1 | *Petunia inflata* | Petunia | SEQ ID NO: 40 |
| Peaxi162Scf00078g00059.1 | *Petunia axillaris* | White Petunia | SEQ ID NO: 41 |
| SMEL_012g387130.1.01 | *Solanum melongena* | Eggplant | SEQ ID NO: 42 |
| Capana10g001758 | *Capsicum annuum Zunla* | Pepper | SEQ ID NO: 43 |
| CA05g11610 | *Capsicum annuum* | Pepper (CM334) | SEQ ID NO: 44 |
| Niben101Scf05041g04001.1 | *Nicotiana benthamiana* | Tobacco | SEQ ID NO: 45 |
| Niben101Scf02182g12004.1 | *Nicotiana benthamiana* | Tobacco | SEQ ID NO: 46 |
| Sopen01g028590.1 | *Solanum pennellii* | Wild tomato | SEQ ID NO: 47 |
| Niben101Scf13863g00010.1 | *Nicotiana benthamiana* | Tobacco | SEQ ID NO: 48 |
| SMEL_001g140830.1.01 | *Solanum melongena* | Eggplant | SEQ ID NO: 49 |
| Capana01g003223 | *Capsicum annuum Zunla* | Pepper | SEQ ID NO: 50 |
| Solyc01g066980.3.1 | *Solanum lycopersicum* | Tomato | SEQ ID NO: 51 |
| Sopen01g028640.1 | *Solanum pennellii* | Wild tomato | SEQ ID NO: 52 |
| Sopim01g066980.0.1 | *Solanum pimpinellifolium* | Wild tomato | SEQ ID NO: 53 |
| PGSC0003DMP400020089 | *Solanum tuberosum* | Potato | SEQ ID NO: 54 |
| Niben101Scf10524g05008.1 | *Nicotiana benthamiana* | Tobacco | SEQ ID NO: 55 |
| Peaxi162Scf00534g00012.1 | *Petunia axillaris* | White Petunia | SEQ ID NO: 56 |
| Peinf101Scf01113g00005.1 | *Petunia inflata* | Petunia | SEQ ID NO: 57 |
| Peaxi162Scf00086g00036.1 | *Petunia axillaris* | White Petunia | SEQ ID NO: 58 |
| Peinf101Scf00973g06042.1 | *Petunia inflata* | Petunia | SEQ ID NO: 59 |
| Capana01g003222 | *Capsicum annuum Zunla* | Pepper | SEQ ID NO: 60 |
| Peaxi162Scf00534g00005.1 | *Petunia axillaris* | White Petunia | SEQ ID NO: 61 |
| Peinf101Scf01113g00004.1 | *Petunia inflata* | Petunia | SEQ ID NO: 62 |
| SMEL_001g140850.1.01 | *Solanum melongena* | Eggplant | SEQ ID NO: 63 |
| Niben101Scf02626g03001.1 | *Nicotiana benthamiana* | Tobacco | SEQ ID NO: 64 |
| Niben101Scf10524g05006.1 | *Nicotiana benthamiana* | Tobacco | SEQ ID NO: 65 |
| Solyc01g066970.2.1 | *Solanum lycopersicum* | Tomato | SEQ ID NO: 66 |
| Sopen01g028630.1 | *Solanum pennellii* | Wild tomato | SEQ ID NO: 67 |
| PGSC0003DMP400020088 | *Solanum tuberosum* | Potato | SEQ ID NO: 68 |
| Sopen01g028610.1 | *Solanum pennellii* | Wild tomato | SEQ ID NO: 69 |
| Solyc01g066950.1.1 | *Solanum lycopersicum* | Tomato | SEQ ID NO: 70 |
| Capana12g000135 | *Capsicum annuum Zunla* | Pepper | SEQ ID NO: 71 |
| Capang12g000108 | *Capsicum annuum* | Pepper (Chiltepin) | SEQ ID NO: 72 |
| SMEL 005g240480.1.01 | *Solanum melongena* | Eggplant | SEQ ID NO: 73 |
| Solyc12g099610.1.1 | *Solanum lycopersicum* | Tomato | SEQ ID NO: 74 |
| PGSC0003DMP400008206 | *Solanum tuberosum* | Potato | SEQ ID NO: 75 |

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

The following examples are provided to illustrate certain particular features and/or embodiments. These examples should not be construed to limit the disclosure to the particular features or embodiments described.

EXAMPLES

Example 1

Identification of Brachytic Homologs

Figure 4:
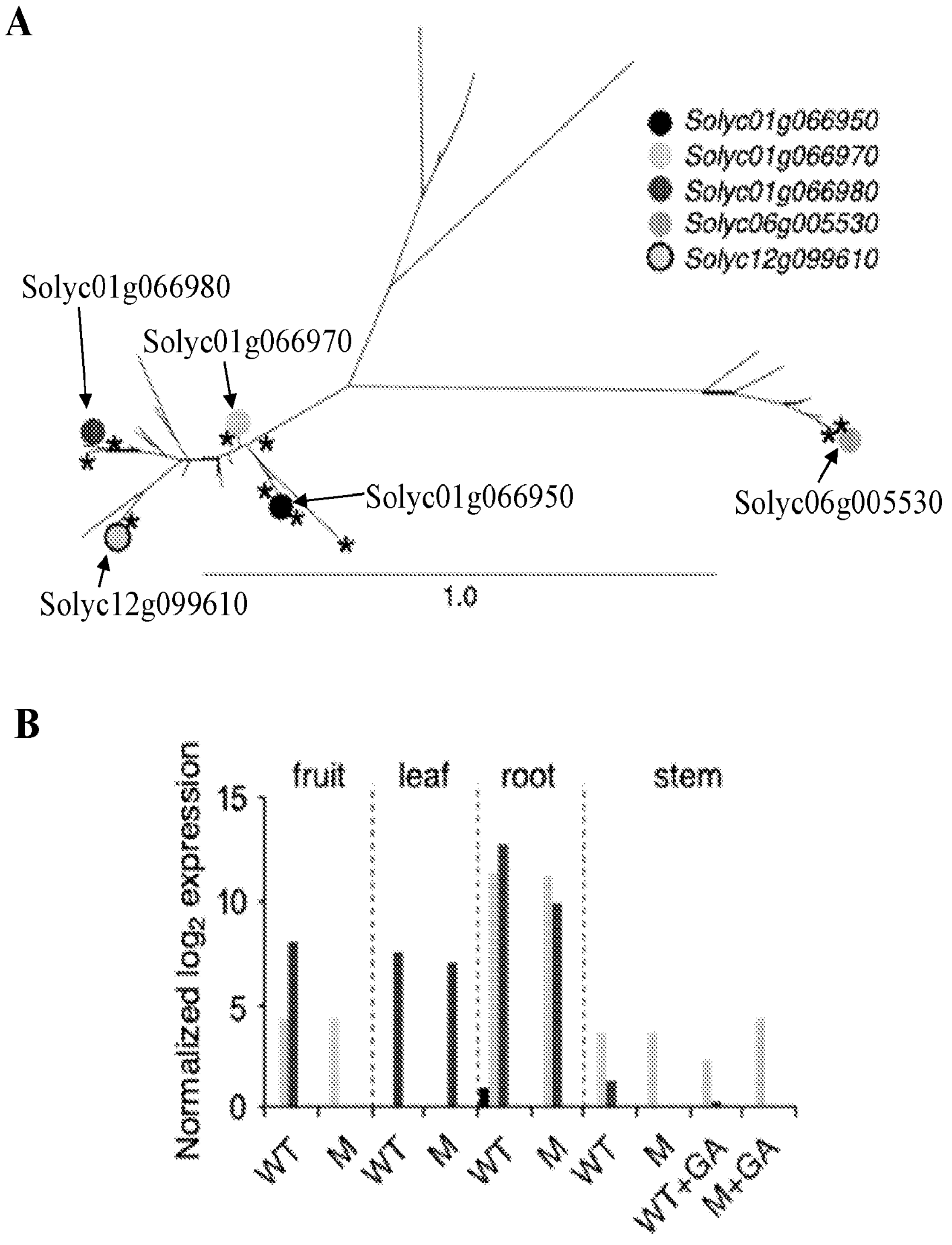
FIG. 4. Network analysis of gene expression patterns across tissues, genotypes, and gibberellic acid (GA) treatments. (A) Diagram illustrating phylogenetic tree of Solanaceae flowering promoting factor 1 (FPF1) families. Dots represent five modern tomato (*Solanum lycopersicum*) FPF1s identified by sequence similarity to the families in Solanaceae species. Wild tomatoes (*S. pimpinellifolium* and *S. pennellii*) are indicated by asterisks. Scale bar represents 1.0 substitutions per site. (B) Graph illustrating expression of tomato FPF1s in different tissues. WT=wild-type plant, M=br plant (Solyc01g066980). For each expression levels are indicated, in order, for Solyc01g066950, Solyc01g066970, Solyc01g066990, Solyc06g005530, and Solyc12g099610.

To identify the FPF (brachytic) gene family in Solanaceae, we performed a hidden Markov model (HMM) search using the PFAM FPF model against the 11 Solanaceae annotated protein datasets, including three tomato species, one modern (cultivated) (*Solanum lycopersicum*) and two wild tomatoes (*S. pimpinellifolium* and *S. pennellii*). We identified 57 protein sequences (including five modern tomato sequences) matching the model. For each of species, multiple sequences were identified in the datasets used in this study (ranging from three FPFs in *Capsicum annuum* cv. CM334 to eight in *N. benthamiana*). A maximum likelihood phylogenetic analysis revealed that five modern tomato sequences can be clustered into two categories (FIG. 4A). One contained all three FPFs on chromosome 1. The other category clustered all three tomato species, including a single modern tomato gene Solyc06g005530, close to a single terminal branch. Both wild tomatoes and modern tomato had five FPF1s. However, the modern tomato and its closest relative *S. pimpinellifolium* carried three FPF1s on chromosome 1, while *S. pennellii* carried four FPF1s on chromosome 1, implying molecular divergence in the FPF1 family in *Solanum*.

To obtain an overview of the expression profiles of the five tomato FPF1s, RNA-seq libraries were constructed from different tissue types, the first internode (stem), leaf, and root at the 6-week-old growth stage (the growth stage used in conventional brachytic phenotyping; Lee et al., 2018). Additionally, first internodes collected 3 h after $GA_3$ treatment at the 6-week-old stage were used for library construction. Comparing the expression profiles among homologs, both Br (Solyc01g066980) and its immediately adjacent gene Solyc01g066970 were expressed (FIG. 4B). Solyc01g066970 expression was not significantly affected by genotype. Notably, both genes were highly expressed in roots and expression levels of those two genes were not significantly affected by $GA_3$ treatment. The other three homologs had low expression levels in most or all tissue types.

RNAseq and expression analysis: Wild-type and mutant ($M_2$ generation of br.8.2$^{CR}$), tissue samples were collected from individual plants grown simultaneously with plants used to the greenhouse trial in the fall. Five different tissue types were collected: stem without $GA_3$ treatment (specifically the 1$^{st}$ internode) at the 6-week-old stage, stem (specifically the 1$^{st}$ internode) collected 3 h after $GA_3$ treatment at the 6-week-old stage, leaf at the 6-week-old stage, root at the 6-week-old stage, and fruit at the time of harvest. The leaf, stem with or without $GA_3$ treatment, and root samples were collected from 6-week-old plants. For each biological replication, the stem, leaf, and root were collected from the same individual plant, and four biological replications (four different plants) were collected for each genotype and tissue type. The samples were flash-frozen in liquid nitrogen immediately after excision.

Example 2

Gene Editing Tomato Plants Using CRISPR System

Figure 1:
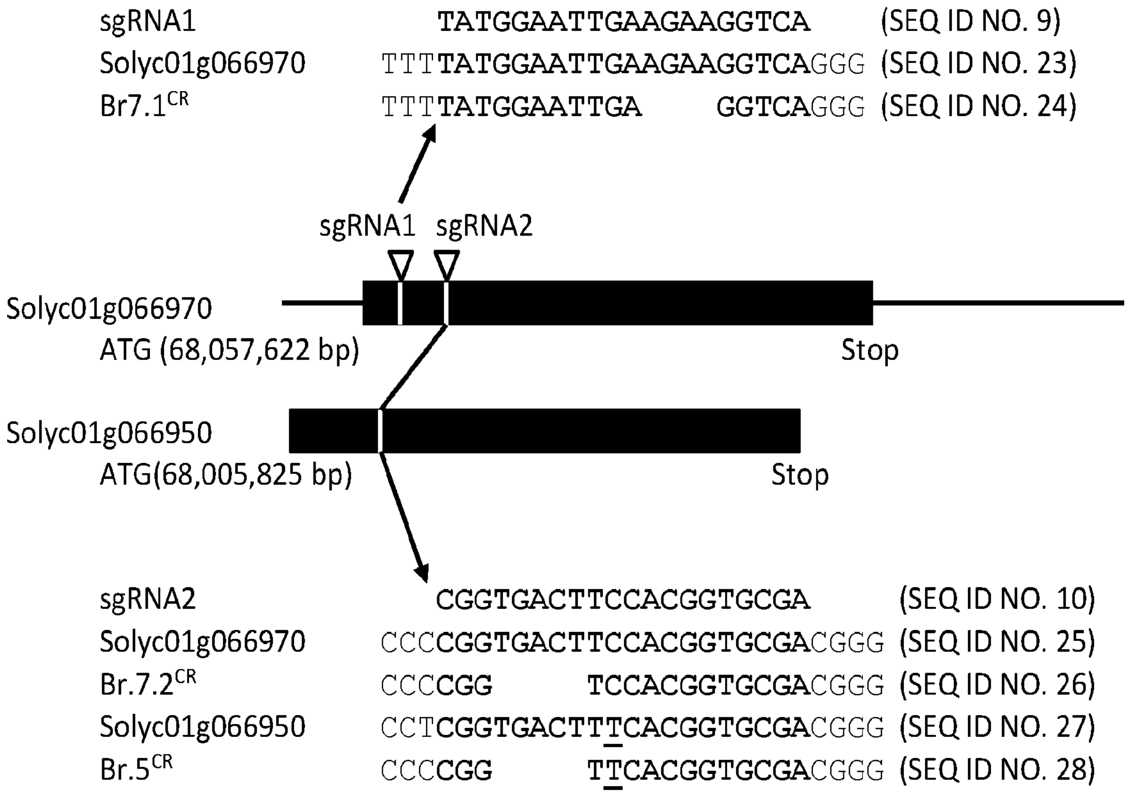
FIG. 1. Illustration showing crRNA guide sequences for modification of the Solyc01g066970 and Solyc01g066950 loci. Mutations in the Solyc01g066970 and Solyc01g066950 loci generated using CRISPR systems with gRNAs having the indicated guide sequences are also shown.

CRISPR constructs were designed to create deletions within the Solyc01g066970 and/or Solyc01g066950 loci the using sgRNA alongside the zCas9 endonuclease gene. zCas9 is a Cas9 gene that has been codon optimized for maize. Two different gRNA sequences containing SEQ ID NOs: 9 and 10 guide sequences were used to form CRISPR/zCas9 constructs to genetically modify the Solyc01g066970 and/or Solyc01g066950 loci in tomato plants to produce brachytic plants. The locations of the guide sequences relative to the Solyc01g066970 and Solyc01g066950 loci are illustrated in FIG. 1. All constructs were assembled as described by Xie et al. 2014 with minor modifications. pHSN401 vector (Addgene) was used to make the CRISPR/zCas9 constructs. *Agrobacterium tumefaciens*-mediated transformations of the standard fresh-market tomato (*Solanum lycopersicum*) variety Fla. 8059 were performed according to Van Eck et al. 2006 with minor modifications. Two different *A. tumefaciens* strains AGL1 (ATCC) and LBA4404 (Takara Bio USA), containing the indicted CRISPR/zCas9 constructs were used for transformations. After selecting regenerants on selecting media with hygromycin, regenerants were moved to the greenhouse. Young leaf tissues were collected from each T0 plant, and genomic DNA was extracted using Qiagen DNeasy kit (Qiagen, USA). Each plant was genotyped for the presence of the CRISPR/zCas9 construct. Plants positive for Cas9 T-DNA were further genotyped for brachytic genome modification using Sanger.

The Solyc01g066970 locus and the Solyc01g066950 locus mutants were generated using the CRISPR/Cas9 system (Plant Physiology 2014 166:1292-1294). The gRNAs sequences used to target the locus are shown in FIG. 1. sgRNA1 targets the Solyc01g066970 locus. sgRNA2 targets both the Solyc01g066970 locus and the Solyc01g066950 locus. For the sgRNA, the tracrRNA component had the sequence: GTTTAGAGCTAGAAATAGCAAGT-TAAAATA-AGGCTAGTCCGTTATCAACTT-GAAAAAGTGGCACCGAGTCGGTGC (SEQ ID NO: 4) or an RNA equivalent thereof. The resulting constructs were introduced into Fla. 8059 (HORTSCIENCE 2008 43:2228-2230) background by *Agrobacterium tumefaciens*-mediated transformation.

Figure 2:
FIG. 2. CRISPR/Cas9-driven single mutant (brachytic) plant (left), which shows a shortened internode length compared to its background Fla 8059 (right). Scale bar=10 cm.

As shown in FIG. 2, tomato plants having CRISPR/zCas9-induced deletions in the Solyc01g066970 and Solyc01g066950 loci exhibited the brachytic phenotype, shortened height and decreased internode length (compare left (genetically modified) plants and right (normal) plants and in FIG. 2. The genetically modified plants contained 4 and 5 base pair deletions in the Solyc01g066970 locus and a 5 base pair deletion in the Solyc01g066950 locus (FIG. 1).

Figure 3:
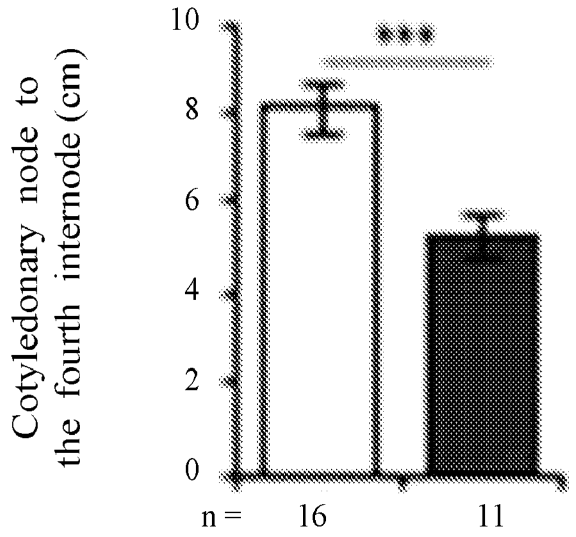
FIG. 3. Graph illustrating reduced stem length in double-mutant plants. White bar=wild type plants. Dark bar=br0.5CRbr.7.2CR (M1) plants. Statistically significant ***P<0.001 based on a two-tailed t-test.

As illustrated in FIG. 3, the double mutant plants (black bar) had statistically reduced internode length. Shortened internode length was also observed in Solyc01g066970-mutant plants generated using a single sgRNA, sgRNA1.

Example 3

Mutated br Homologs Present New Sources of a Reduced Plant Height

Considering the observed sequence variation and expression patterns of FPFs adjacent to the Br (Solyc01g066980) on chromosome 1, we investigated phenotypes associated with mutated versions of those two br homologs, Solyc01g066950 and Solyc01g066970.

Guide RNAs (gRNAs) targeting FPF (Br) genes were designed using CRISPR-P (Lei et al., 2014) and CRISPR-PLANT (Xie et al., 2014) and each of the gRNAs was cloned into a binary vector following the same basic procedures described by Xie and Yang (2013) (Table 3). Duplex oligos carrying BsaI sites in binary vectors were synthesized (IDT). The binary vector pHSN401 (addgene)-gRNA plasmid was introduced into *Agrobacterium tumefaciens* strain LBA4404 (Takara) according to the manufacturer's instructions. *A. tumefaciens*-mediated transformations of Fla. 8059 [A parental line of 'Tasti-Lee $F_1$' (Bejo, Seeds, Oceano, CA), Scott et al., 2008; Tasti-Lee $F_1$ is a fresh-market tomato cultivar currently in the US market (e.g., Publix Super Markets, Inc.)] were performed as described by Van Eck et al., 2019, with modifications in the preculture medium and selective regeneration medium steps: Cotyledon explants from 7 to 9-day-old seedlings were precultured and 3 mg/L or 6 mg/L hygromycin was used.

Potential Cas9-gRNA-introduced mutations were examined by Sanger sequencing of PCR products and the T7 Endonuclease I assay (NEB) using the PCR primers in Table 4. Total genomic DNA of each transformed plant in the $M_0$ generation was extracted from young leaves using the DNeasy Plant Mini Kit (Qiagen). PCRs were performed to examine mutations in the targeted region. PCR cycling and running parameters were as follows: initial denaturation step at 95° C. for 7 min, 30 cycles at 95° C. for 30 s, 60° C. for 30 s, and 72° C. for 1 min, followed by a final extension at 72° C. for 7 min. For the T7 Endonuclease I assay, genomic DNA extracted from individual plants was used as the template. A pair of targeted region-specific primers and Q5 Hot Start High-Fidelity 2× Master Mix (NEB) were used for PCR. The cycling and running parameters were as follows: initial denaturation step at 98° C. for 30 s, 35 cycles at 98° C. for 5 s, 60° C. for 10 s, and 72° C. for 20 s, followed by a final extension at 72° C. for 2 min. PCR products were purified using a QIAquick PCR Purification Kit (Qiagen), and 200 ng of the PCR products was digested with T7E1 according to the manufacturer's instructions. To identify homozygous transgene-free mutants, four primer pairs targeting the Cas9 gene in the binary vector or the Hyg gene were used. Potential transgene-free mutants were further validated by whole genome sequencing. Potential off-target sites (i.e., up to four mismatches compared to each target region) were predicted using the Cas-OFFinder (Bae et al., 2014). A lack of off-target activity was verified (Table 5).

TABLE 3 guide RNAs

| Oligo | Sequence | SEQ ID NO. | Target |
|---|---|---|---|
| sgRNA1 | ATCGGAGTTC TCCACTAGA | 115 | Solyc01g066980 |
| sgRNA2 | GAAGATGTAC AAGAACTTTT | 116 | Solyc01g066980 |
| sgRNA3 | TCGCACCGTGA AAGTCACCG | 117 | Solyc01g066950 & Solyc01g066970 |

TABLE 4

PCR primers for mutation detection

| Oligo | Sequence | SEQ ID NO. | Target |
|---|---|---|---|
| Br_80_F | TTCCCCTCTT ACAACTTTCC AA | 118 | Solyc01g066980 |
| Br_80_R | CCAGAAACGG GGGAGACTAC | 119 | |
| Br_70_F | CATGTGCATG GACTTGAGGT TG | 120 | Solyc01g066970 |
| Br_70_R | AGGGCTGATC AAGCAATGGA T | 121 | |
| Br_50_F | GACCTGAGGT TGTTGAAGTC GT | 122 | Solyc01g066950 |
| Br_50_R | TTTTGGGTCG TGACAGGTAA A | 123 | |
| Cas9_F11 | CCAGATTCAT CTCGGGGAGC | 124 | Cas9 |
| Cas9_R11 | GAGCTGCTTA ACCGTGACCT | 125 | |
| Cas9_F12 | GGACTTCCTG GACAACGAGG | 126 | Cas9 |
| Cas9_R12 | CGTGAGTTCT TCTGGCCCTT | 127 | |
| Hyg_F2 | GAGGGCGTGG ATATGTCCTG | 128 | HygR |
| Hyg_R2 | GGCGACCTCG TATTGGGAAT | 129 | |
| Hyg_F11 | GCTCTCGATG AGCTGATGCT | 130 | HygR |
| Hyg_R11 | ATTTGTGTAC GCCCGACAGT | 131 | |

TABLE 5

| Potential off-targets | | | | | | |
|---|---|---|---|---|---|---|
| guide RNA[a] | Potential off-target [b] | SEQ ID NO. | Chrom.[c] | Position (bp) [d] | Strand [e] | Mismatches |
| sgRNA1 | GAaCGtAGTTgaCCACTAGATGG | 132 | 7 | 13,262,523 | minus | 4 |
| | GATtGaAGTTCTCCgtTAGATGG | 133 | 8 | 14,774,353 | minus | 4 |
| | cAatGGAGTTCTtCACTAGAGGG | 134 | 10 | 26,886,339 | minus | 4 |
| | GATgaGAGTTCTgCACTtGATGG | 135 | 11 | 46,729,949 | minus | 4 |
| sgRNA2 | ttAtGATGTACAAaAACTTTTAGG | 136 | 1 | 2,916,807 | plus | 4 |
| | GGAAGATGTACcAatACgTTTCGG | 137 | 1 | 27,276,750 | plus | 4 |
| | ttAAGATtTACAACAACTTTTTGG | 138 | 1 | 78,063,314 | minus | 4 |
| | GGAAGATGTcCtAGttCTTTTTGG | 139 | 1 | 81,784,871 | minus | 4 |
| | GGAAcATGTACAAGAAgcTTgAGG | 140 | 1 | 85,341,524 | minus | 4 |
| | GGAAGAcGTtCAAGAAtTTTTCGG | 141 | 2 | 22,562,061 | plus | 3 |
| | GGAAGATGaAtAAtAACTaTTTGG | 142 | 3 | 27,226,946 | plus | 4 |
| | aacAGAaGTACAAGAACTTTTGGG | 143 | 5 | 16,839,941 | plus | 4 |
| | aGcAGATGTACAAGAtCTTTaAGG | 144 | 5 | 46,179,653 | minus | 4 |
| | aGAAGcTGTAtAtGAACTTTTGGG | 145 | 6 | 46,988,801 | plus | 4 |
| | GGAAGAaGaAgAAGAAgTTTAGG | 146 | 7 | 7,766,201 | plus | 4 |
| | tGAtGATGTAaAAGAACTTTTTGG | 147 | 7 | 44,564,055 | minus | 3 |
| | GGAAGATGgACAAcAAgaTTTAGG | 148 | 8 | 21,797,045 | plus | 4 |
| | tGAAGAaGcACAAGAgCTTTTTGG | 149 | 8 | 36,797,374 | minus | 4 |
| | GGAtGATaTACAAGcAtTTTTAGG | 150 | 8 | 56,549,095 | minus | 4 |
| | GGAAGATGTACcAtAACTTTaGGG | 151 | 9 | 41,907,371 | minus | 3 |
| | GcAAGATGcACAAGAcCcTTTGGG | 152 | 9 | 48,273,212 | plus | 4 |
| | GcAAGATcTACAAGAACTTcaCGG | 153 | 10 | 1,415,058 | plus | 4 |
| | GGAAGATaTtCAAtAAaTTTTAGG | 154 | 11 | 53,105,006 | minus | 4 |
| | GGAAGATaTgaAAGAACTTTaTGG | 155 | 12 | 29,596,866 | minus | 4 |

[a] No potential off-targets were found for the sgRNA3 in this study.

[b] Potential off-targets with a maximum mismatch of four were identified. Small letters indicate mismatches compared to each target region.

[c]Chromosome, tomato reference genome assembly SL4.0.

[d] position relative to the first nucleotide of each target region.

e DNA strand orientation

Using a single-guide RNA targeting a sequence region only differentiated by a single nucleotide, three different mutants were obtained simultaneously (FIG. 5): br.7$^{CR}$, having a 1 bp insertion in Solyc01g066970; br.57.1$^{Cr}$, having a 5 bp deletion in both Solyc01g066950 and Solyc01g066970; and br.57.2$^{CR}$, having a 1 bp insertion in Solyc01g066950 and a 5 bp deletion in Solyc01g066970. None of these mutants had DNA sequence variation in Br (Solyc01g066980). All three mutants showed significantly reduced height (FIG. 6). As the number of genes knocked out increased, the stem length reduced accordingly. The findings indicate that multiple br homologs confer a br plant-like shortened stem length.

The data demonstrate that CRISPR-mediated knock-out(s) of Br homologs can confer a br plant-like shortened architecture (reduced plant height), while retaining the production of heavy fruits.

High levels of genetic variation [e.g., copy number variation of DNA segments (CNV)], have been observed in plant genomes, and emerging evidence indicates that CNVs mediate a number of valuable crop traits [for example, CNV (1 to 11 copies)-mediated soybean cyst nematode resistance]. Together with these results, this suggests creation of tomato lines that carry mutations in multiple FPF1 genes (e.g., knock-outs of 2, 3, 4, or all 5 of the br homologs) will be useful in generating tomato plants having a brachytic phenotype and large (medium or larger) fruit. CRISPR mediated knockout of two or more Br homolog genes may result in considerably reduced plant architectures than those obtained by single mutants.

Example 4

Generation of Loss of Function Mutations at Other Brachytic Loci Using CRISPR Systems Identification of protospacer-adjacent motif (PAM) sites in the, Solyc01g066950, Solyc01g066970, Solyc06g005530, Solyc12g099610, and Solyc01g066980 genes for CRISPR/zCas9 generation of brachytic plants. In addition to the guide sequences described above, additional guide sequences are suitable for forming gRNAs (as used herein gRNA can include crRNA, gRNA, and sgRNA) for CRISPR/zCas9 mediated genetic modification of a br locus. Suitable guide sequences include 17-20 nucleotide sequences in SEQ ID NOs: 1, 2, 6, 7, 11, 12, 16, 17, 21, or 102 or a complement thereof that are unique compared to the rest of the genome and immediately adjacent (5') to a protospacer-adjacent motif (PAM) site. For zCas9, a PAM site is NGG. Thus, any unique 17-20 nucleotide sequence immediately 5' of a 5'-NGG-3' in in SEQ ID NOs: 1, 2, 6, 7, 11, 12, 16, 17, 21, or 102 or a complement thereof can be used in forming a gRNA. PAM sites in the SEQ ID NOs: 1, 2, 6, 7, 11, 12, 16, 17, 21, and 102 are shown in Table 1, where GG and CC PAM sites are shown in capital letters. CC sequences in the listed strand correspond to GG sequences in the complement strand. Deletions or insertions in the flanking regions may alter expression of the brachytic gene leading to plants displaying a brachytic phenotype.

CRISPR modification of the brachytic locus is not limited to the CRISPR/zCas9 system. Other CRISPR systems using different nucleases and having different PAM sequence requirements are known in the art. PAM sequences vary by the species of RNA-guided DNA endonuclease. For example, Class 2 CRISPR-Cas type II endonuclease derived from *S. pyogenes* utilizes an NGG PAM sequence located on the immediate 3' end of the guide sequence. Other PAM sequences include, but are not limited to, NNNNGATT (*Neisseria meningitidis*), NNAGAA (*Streptococcus thermophilus*), and NAAAAC (*Treponema denticola*). Guide sequences for CRISPR systems having nucleases with different PAM sequence requirements are identified as described above for zCas9, substituting the different PAM sequences.

In some embodiments, two or more gRNAs can be used. The two or more gRNAs can used with the same RNA-guided DNA endonuclease (Cas nuclease) or different RNA-guided DNA endonucleases. CRISPR mediated modification of other brachytic loci, such as the Solyc06g005530 locus or the Solyc12g099610 locus, in tomato plants is accomplished in a similar manner by selecting target sequences as described in example 3 for Solyc01g066950 and Solyc01g066970.

CRISPR mediated modification of homologous or orthologous brachytic loci in other Solanaceae plants is accomplished in a similar manner by selecting target sequences as described in example 3 for Solyc01g066950 and Solyc01g066970. Exemplary homologous brachytic amino acid sequences are provided in Table 2.

The invention claimed is:

1. A genetically modified *Solanum lycopersicum* plant wherein Solyc01g066950 locus and a Solyc01g066970 locus have been genetically modified through the use of a CRISPR/Cas system, wherein the Solyc012g066950 locus consists of SEQ ID NO:1 and the Solyc01g066970 locus consists of SEQ ID NO:6; and wherein the genetic modification results in loss of function or decreased expression of coding sequences comprising SEQ ID NO:2 and SEQ ID NO:7.

2. The genetically modified *Solanum lycopersicum* plant of claim 1, wherein the *Solanum lycopersicum* plant has been further genetically modified through the use of a CRISPR/Cas system at: a Solyc06g005530 locus, a Solyc12g099610 locus, and/or a Solyc01g066980 locus; wherein:

(i) the Solyc06g005530 locus consists of SEQ ID NO:11 and the genetic modification results in loss of function or decreased expression of a coding sequence comprising SEQ ID NO:12;

(ii) the Solyc12g099610 locus consists of SEQ ID NO:16, and the genetic modification results in loss of function or decreased expression of a coding sequence comprising SEQ ID NO: 17; or (iii) the Solyc01g066980 locus consists of SEQ ID NO:102, and the genetic modification results in loss of function or decreased expression of a coding sequence comprising SEQ ID NO:21.

3. The genetically modified *Solanum lycopersicum* plant of claim 2, wherein the *Solanum lycopersicum* plant has been genetically modified through the use of a CRISPR/Cas system at:

(a) the Solyc01g066950 locus, the Solyc01g066970 locus, and the Solyc06g005530 locus;

(b) the Solyc01g066950 locus, the Solyc01g066970 locus, and the Solyc01g066980 locus; or (c) the Solyc01g066950 locus, the Solyc01g066970 locus, and the Solyc12g099610 locus.

4. The genetically modified *Solanum lycopersicum* plant of claim 1, wherein the *Solanum lycopersicum* plant has been genetically modified through the use of a CRISPR/Cas system at:

(a) the Solyc01g066950 locus, the Solyc01g066970 locus, the Solyc06g005530 locus, and the Solyc12g099610 locus;

(b) the Solyc01g066950 locus, the Solyc01g066970 locus, the Solyc06g005530 locus, and the Solyc01g066980 locus; or (c) the Solyc01g066950 locus, the Solyc01g066970 locus, the Solyc12g099610 locus, and the Solyc01g066980 locus.

5. The genetically modified *Solanum lycopersicum* plant of claim 2, wherein the *Solanum lycopersicum* plant has been genetically modified through the use of a CRISPR/Cas system at: the Solyc01g066950 locus, the Solyc01g066970 locus, the Solyc06g005530 locus, the Solyc12g099610 locus, and the Solyc01g066980 locus.

6. The genetically modified *Solanum lycopersicum* plant of claim 1, wherein the *Solanum lycopersicum* plant contains a deletion or disruption at the Solyc01g066950 locus and the Solyc01g066970 locus.

7. A method of genetically modifying a *Solanum lycopersicum* plant to produce a plant having a brachytic phenotype, the method comprising:

(a) introducing a CRISPR system into a *Solanum lycopersicum* plant cell, wherein the CRISPR system comprises:

(i) one or more RNA-guided DNA endonucleases or one or more nucleic acids encoding the one or more RNA-guided DNA endonucleases; and (ii) one or more guide RN As or one or more nucleic acids encoding the one or more guide RNAs into a plant cell;

wherein the one or more RNA-guided DNA endonucleases and the one or more guide RNAs form one or more complexes that target a Solyc01g066950 locus and a Solyc01g066970 locus, and wherein the Solyc01g066950 locus consists of SEQ ID NO: 1 and the Solyc01g066970 locus consists of SEQ ID NO:6, and thereby decreasing expression of or generating loss of function mutations in coding sequences comprising SEQ ID NO:2 and SEQ ID NO:7; and (b) generating one or more regenerant plants following introducing the CRISPR system into the *Solanum lycopersicum* plant cell, and wherein the plants and/or progeny of the plants comprise the genetic modification resulting in loss of function or decreased expression of coding sequences comprising SEQ ID NO:2 and SEQ ID NO:7.

8. The method of claim 7, wherein the RNA-guided DNA endonuclease comprises a zCas9 nuclease, a Cas9 nuclease, type II Cas nuclease, an nCas9 nuclease, a type V Cas nuclease, a Cas12a nuclease, a Cas12b nuclease, a Cas12c nuclease, a CasY nuclease, a CasX nuclease, a Cas12i nuclease, or an engineered RNA-guided DNA endonuclease.

9. The method of claim 7, wherein the one or more guide RNAs comprise:

(a) a 17-20 nucleotide guide sequence comprising 17-20 contiguous nucleotides differing by no more than 1 or 2 nucleotides present in SEQ ID NO: 1 or a complement thereof; and/or (b) a 17-20 nucleotide guide sequence comprising 17-20 contiguous nucleotides differing by no more than 1 or 2 nucleotides present in SEQ ID NO: 6 or a complement thereof;

wherein the 17-20 nucleotide sequence is unique compared to the rest of the genome of the *Solanum lycopersicum* plant and is immediately adjacent (5') to a protospacer-adjacent motif (PAM) site.

10. The method of claim 9, wherein the one or more guide RNAs comprise:

(a) a 17-20 nucleotide guide sequence comprising 17-20 contiguous nucleotides differing by no more than 1 or 2 nucleotides present in SEQ ID NO: 2 or a complement thereof or an ortholog thereof; or (b) a 17-20 nucleotide guide sequence comprising 17-20 contiguous nucleotides differing by no more than 1 or 2 nucleotides present in SEQ ID NO: 7 or a complement thereof or an ortholog thereof.

11. The method of claim 9, wherein the one or more guide RNAs comprise one or more nucleic acid sequences selected from the group consisting of: SEQ ID NO: 5, SEQ ID NO: 9, SEQ ID NO: 10, and SEQ ID NO: 117, or an RNA equivalent thereof.

12. The method of claim 7, wherein the CRISPR system comprises at least two guide RNAs that target the Solyc01g066950 locus and the Solyc01g066970 locus.

13. The method of claim 11, wherein the one or more guide RNAs comprises SEQ ID NO: 9 or an RNA equivalent thereof and SEQ ID NO: 10 or an RNA equivalent thereof.

14. The method of claim 7, wherein the CRISPR system creates a deletion of one or more nucleotides in the Solyc01g066950 locus and the Solyc01g066970 locus.

15. The method of claim 7, wherein the method generates loss of function mutations in:

(a) the Solyc01g066950 locus and the Solyc01g066970 locus;

(b) the Solyc01g066950 locus, the Solyc01g066970 locus, and the Solyc06g005530 locus;

(c) the Solyc01g066950 locus, the Solyc01g066970 locus, and the Solyc12g099610 locus; or (d) the Solyc01g066950 locus, the Solyc01g066970 locus, the Solyc06g005530 locus, and the Solyc12g099610 locus; wherein:

(i) the Solyc06g005530 locus consists of SEQ ID NO:11 and the genetic modification results in loss of function or decreased expression of a coding sequence comprising SEQ ID NO:12; and (ii) the Solyc12g099610 locus consists of SEQ ID NO:16, and the genetic modification results in loss of function or decreased expression of a coding sequence comprising SEQ ID NO: 17.

16. The method of claim 7, wherein the method further comprises selecting one or more $T_0$ plants containing the genomic modification at the Solyc01g066950 locus and the Solyc01g066970 locus.

17. The method of claim 7, wherein genetically modifying the *Solanum lycopersicum* plant results in the *Solanum lycopersicum* plant having shortened height and/or decreased internode length.

18. The method of claim 7, further comprising introducing an additional guide RNA or a nucleic acid encoding the additional guide RNA into the *Solanum lycopersicum* plant, wherein the additional guide RNA comprises a 17-20 nucleotide guide sequence comprising 17-20 contiguous nucleotides differing by no more than 1 or 2 nucleotides present in SEQ ID NO: 21 or 102.

* * * * *

SEQUENCE LISTING

```
<160> NUMBER OF SEQ ID NOS: 155

<210> SEQ ID NO 1
<211> LENGTH: 2226
<212> TYPE: DNA
<213> ORGANISM: Solanum lycopersicum

<400> SEQUENCE: 1

aatatactca atctaatgaa cctaattccc aaatgagtat ggtattgagg cttgagtcct     60

catgtgtgaa cttggcggta cttattaacg atcatagtac ttgttgttgc tacatgttga    120

gtaatgtagt tgatttcata ttattacttg atatatattg ctttctattt tgagttggcc    180

gatgatcgtg ttttgtactg acccctactt gtatgtttct ttccttgtta tttgtggagt    240

gcagcaaacg tgccgtcgtc tttaactcaa ccgcaactct agccgatctt cattacaccg    300

gatttcaggg tgagctaacg cttctagctt ggactggatc ttcttcttca tgtctcgatg    360

ccttgaagtt ccggcatgaa ctagctttta tttattctag ctttctagat actcttagct    420

ttagtaattt gaggatagat gttcttatga tgatgacttc cagattttgg ggataataat    480

agttgttgag tttttagaag ttatttaatt gattttcatt aatgaggtta agtcttccgc    540

attatattcc gtcattatat tgaaatgttg ggtttagatt ggttggttcg ctcacatagg    600

aagataaatg tgggtgccac tcgcggtccg ttttgggtcg tgacaggtaa attagggtat    660

cttgtggcca tataaatatt ctccctttct ttttctttaa tcttatgagc gtacgataag    720

ttagtataat tctaaatcct acctattaat catcatcaat tttattaaat aagaaagaaa    780

atacttttttg ccacctaatg tattttttat tacatagaaa cccgtataaa aaccccttca    840
```

-continued

```
cacttatctt caaactcaca cacaatactc actcactagt ttcatattca tattttttga    900

aacatgtctg gtgtttggaa aatcaagaat ggagtagtga ggctagttga gaacctcggt    960

gactttcacg gtgcgacggg tcgtcgtaaa gtgcttgtgc acctttctag taatgaagta   1020

ataacatcat atgcagtact tgaaaggaaa ctgtactctc ttggatggga gaggtactat   1080

gatgaccctg accttcttca gtaccataaa agatcaactg ttcatcttat ttctctacca   1140

aacgacttca acaacctcag gtccatgcac atgtatgata ttgttgttaa gaatcgtaat   1200

gagtttgctg ttagggatat gtagtattac taataatcat tagttgattt gagatttttc   1260

tcaaattaat taatgttgtt taatttaaat taggttgttt cttcttttaa cttaaggttt   1320

ggtttgtgta atttaggtca aaggggggtg ttttagtttc ttttgggtga ggaagctaat   1380

tattacttgt tgtaatggtg tgtaagagtg aagtttatgg caataaaact tggtttcgct   1440

tcgaaacttt tatctatata cttaaataaa tttgtactat caaatactta aatttttagt   1500

catatatata tttaaaagtc ttctttattt acttaaattt tgtatcaagt caaaccagat   1560

tatattttta tcattaagcc aacgatgata ggtggatatg tgattgatat attttttttt   1620

atggaaatat cttttctttt ctcttttttt ttttggtctt attttgaata aagacaaaat   1680

ggtattttcc catttatttc atcaagaagt ctttgactat aaattcaaag gctttacctc   1740

aaattcgaat tcttcactgt tttaaaaaaa taaagtaaga tgtcaagaat atatatatat   1800

atatatatat atatatatat atatatatat atatatatat atatatatat atatatatat   1860

atatatatct tttgggaaat ttaattaaat tattatgaag caaataaagg gtaaaagaac   1920

aaataaataa atgcaatcaa ataaatgaag aggtaatatg gacttgggct tttcaggctg   1980

ctaatttggg ttctggccct atttaaacct ttgaaaactt ttgtatacaa caagtgtata   2040

ttgatatata cagatcgttt ctaagccttt ttcctgtata tcaactgtat acagcctgtt   2100

ctaatgcctc caacctgtat cttcattttt gtcaacatat atgttcctga acatatagat   2160

cgctgtatac atattgtata cattatgtat acaactcatt tcttgggctt ttgaattatt   2220

tccaat                                                               2226
```

<210> SEQ ID NO 2
<211> LENGTH: 321
<212> TYPE: DNA
<213> ORGANISM: Solanum lycopersicum

<400> SEQUENCE: 2

```
atgtctggtg tttggaaaat caagaatgga gtagtgaggc tagttgagaa cctcggtgac     60

tttcacggtg cgacgggtcg tcgtaaagtg cttgtgcacc tttctagtaa tgaagtaata    120

acatcatatg cagtacttga aaggaaactg tactctcttg gatgggagag gtactatgat    180

gaccctgacc ttcttcagta ccataaaaga tcaactgttc atcttatttc tctaccaaac    240

gacttcaaca acctcaggtc catgcacatg tatgatattg ttgttaagaa tcgtaatgag    300

tttgctgtta gggatatgta g                                              321
```

<210> SEQ ID NO 3
<211> LENGTH: 106
<212> TYPE: PRT
<213> ORGANISM: Solanum lycopersicum

<400> SEQUENCE: 3

```
Met Ser Gly Val Trp Lys Ile Lys Asn Gly Val Val Arg Leu Val Glu
1               5                   10                  15
```

-continued

```
Asn Leu Gly Asp Phe His Gly Ala Thr Gly Arg Arg Lys Val Leu Val
            20                  25                  30

His Leu Ser Ser Asn Glu Val Ile Thr Ser Tyr Ala Val Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Asn
65                  70                  75                  80

Asp Phe Asn Asn Leu Arg Ser Met His Met Tyr Asp Ile Val Val Lys
                85                  90                  95

Asn Arg Asn Glu Phe Ala Val Arg Asp Met
            100                 105
```

<210> SEQ ID NO 4
<211> LENGTH: 75
<212> TYPE: DNA
<213> ORGANISM: Artificial Sequence
<220> FEATURE:
<223> OTHER INFORMATION: tracrRNA sequence

<400> SEQUENCE: 4

```
gtttagagct agaaatagca agttaaaata aggctagtcc gttatcaact tgaaaaagtg     60

gcaccgagtc ggtgc                                                      75
```

<210> SEQ ID NO 5
<211> LENGTH: 20
<212> TYPE: DNA
<213> ORGANISM: Artificial Sequence
<220> FEATURE:
<223> OTHER INFORMATION: gRNA sequence

<400> SEQUENCE: 5

```
cggtgacttc cacggtgcga                                                 20
```

<210> SEQ ID NO 6
<211> LENGTH: 2291
<212> TYPE: DNA
<213> ORGANISM: Solanum lycopersicum

<400> SEQUENCE: 6

```
tttctctgtc ttgtcttgaa aaaagaatgt ttttttttt tttataattc tttactttca     60

attcttttac atgtgatctt tagaagacaa gattaaataa cattttgata ctttctatat    120

attttaatta taaaatcaca agattcagaa gtcttgttta ttttttaaaa cttcatgtca    180

aactaaaact agataaacaa attggaacag acactatccc attgaaattt tcctattgaa    240

aaatgtccag tggctatact cacactaatg tttaaattac acaacaaaat taaaaaaaaa    300

actcttggta ttttagtgag aatttgtttc tcaccatacg tttttattga cctagttaaa    360

taggaaatgg gtgggaatat cacgtatcat aacacaaatt tctcattgat ttggagtaat    420

ttttttttt taaaaaaaaa ttgttattag acattaatta aggattaaaa gaaacatcat    480

caacatgaga tgggacaaat taatcttccc cgaaatatct tttaatttat ttaattcttc    540

ctttttgtga agggctgatc aagcaatgga tataagaata gaagattgtt cttagcacta    600

aaaaaattaa agaattatgc ttggaaccca ttaaccaaaa gaattaggtt catcttatga    660

gcataagatc attaattagt gattgtttag gagaagattc taatttcagt agggcaaatt    720

agggcatctt gtggccattt aaatattctc cctttctttt tctttaatct taataaacgt    780

acgataagtt agtatatttc taaatcctat aagcagccac attccaaaat cctacctatt    840
```

-continued atcaatttta ttaaataaga aaaaagatta ctttttgcca ccttatgtat ttttttatta 900
cacactacat agaaacccct ataaaaaccc actcacactt atgttcaaac tcacacacaa 960
tactcactta ctattttcat attcatatat tttttgaaac atgtctggtg tttgggtatt 1020
caagaatgga gtagtgaggc tagttgagaa ccccggtgac ttccacggtg cgacgggtcg 1080
tcgtaaagtg cttgtgcacc tttctagtaa tgaagtaata acatcatatg cagtacttga 1140
aaggaaactg tactctcttg gatgggagag gtactatgat gaccctgacc ttcttcaatt 1200
ccataaaaga tcaactgttc atcttatttc tctaccaaag gacttcaaca acctcaagtc 1260
catgcacatg tatgatattg ttgttaagaa tcgtaatgag tttacagtta gggatatgta 1320
gtactactaa ttaataatta gttgatttga gatatttttc tcaaattaat taatgttgtt 1380
tgatttaaat taggttgttt cttgttttaa cttaatgttt ggtttgtgta atttaggttt 1440 aagggggggtg ttttagtttc ttttgggtga ggaagctaat tattacttgt aattgtgtgt 1500
aagagtgaag ttttatggca ataaaaaaac ttggtttggc ttgaaaattt tatctatata 1560
ctgaaataaa ttcttactat caaatacttc aattttgagt ctctcacaca cgcgcatata 1620
tatatatata tatatatata tatatatata tatatatata tatatacttc cccgtttaaa 1680
aaagaataat cttctttcct ttttagtttt ttttttcccc gtttaaaaaa gaataatctt 1740
ctttcctttt tagttttttt ttttatataa aagaatgact tttttttggt tacattttaa 1800
ctttagcttt ccacgtaatt aatttagcgc tacttttcaa ttacaaattc tgctttatta 1860
aatctggtta atgatatttg aaaaatttta atttgtgagg caaattttag gttaagatac 1920
tcgaagagtt tttcttaaga tagttcacat aaggttttgc aaaagttggg agaaattgtt 1980
atatttgaac tagccctatt tctagcttat gtatgaattt gaaataataa taatttaact 2040
atcaaattaa ttatgtatac aagataactc gaataatttg tatatagatt atctctaaca 2100
gatgccttgt agggtattaa atttgcctgc aaggcttttt ccagtttgtt ttctgtataa 2160
taatatgtag catggcatct attccctttt ttaataaata tctattcata atcagacgtc 2220
taaaattcga atacttttct tgataatatc gtcttactcc ttaattagta agttgtgttg 2280
tcattaaata t 2291

<210> SEQ ID NO 7
<211> LENGTH: 321
<212> TYPE: DNA
<213> ORGANISM: Solanum lycopersicum

<400> SEQUENCE: 7
atgtctggtg tttgggtatt caagaatgga gtagtgaggc tagttgagaa ccccggtgac 60
ttccacggtg cgacgggtcg tcgtaaagtg cttgtgcacc tttctagtaa tgaagtaata 120
acatcatatg cagtacttga aaggaaactg tactctcttg gatgggagag gtactatgat 180
gaccctgacc ttcttcaatt ccataaaaga tcaactgttc atcttatttc tctaccaaag 240
gacttcaaca acctcaagtc catgcacatg tatgatattg ttgttaagaa tcgtaatgag 300
tttacagtta gggatatgta g 321

<210> SEQ ID NO 8
<211> LENGTH: 106
<212> TYPE: PRT
<213> ORGANISM: Solanum lycopersicum

<400> SEQUENCE: 8

-continued

```
Met Ser Gly Val Trp Val Phe Lys Asn Gly Val Val Arg Leu Val Glu
1               5                   10                  15

Asn Pro Gly Asp Phe His Gly Ala Thr Gly Arg Arg Lys Val Leu Val
            20                  25                  30

His Leu Ser Ser Asn Glu Val Ile Thr Ser Tyr Ala Val Leu Glu Arg
        35                  40                  45

Lys Leu Tyr Ser Leu Gly Trp Glu Arg Tyr Tyr Asp Asp Pro Asp Leu
    50                  55                  60

Leu Gln Phe His Lys Arg Ser Thr Val His Leu Ile Ser Leu Pro Lys
65                  70                  75                  80

Asp Phe Asn Asn Leu Lys Ser Met His Met Tyr Asp Ile Val Val Lys
                85                  90                  95

Asn Arg Asn Glu Phe Thr Val Arg Asp Met
            100                 105
```

<210> SEQ ID NO 9
<211> LENGTH: 20
<212> TYPE: DNA
<213> ORGANISM: Artificial Sequence
<220> FEATURE:
<223> OTHER INFORMATION: gRNA sequence

<400> SEQUENCE: 9
tatggaattg aagaaggtca 20

<210> SEQ ID NO 10
<211> LENGTH: 20
<212> TYPE: DNA
<213> ORGANISM: Artificial Sequence
<220> FEATURE:
<223> OTHER INFORMATION: gRNA sequence

<400> SEQUENCE: 10
cggtgacttc cacggtgcga 20

<210> SEQ ID NO 11
<211> LENGTH: 2857
<212> TYPE: DNA
<213> ORGANISM: Solanum lycopersicum

<400> SEQUENCE: 11

```
tttattagag atgtcatttg ataatatttt tattatttct tcttcttatt atttttggt      60

taagttatct tcttttcttt tttttctctc tttctatatt tttaccattt aacgaaaata    120

aataaataaa ttacttttat attttcaaaa tgacatagtt gaaccttatc aaggtgttta    180

aaatataaaa agtctacttg aaatgtttaa aagtgaaagt ttatgttact tttaaggatt    240

tgacgatgaa ttttagtatc ctaccatata tttgaaacag cttgtctcat cattgtggta    300

caaatgataa gataaatatt tttttttgt tttttgtttt tcatccggtg ttcgatatca     360

acaatggaac ccaataatat tcagattctt acgaaacgtc ctacatctga gggtaaaata    420

ctccttaaca gagatgactc catagttaga gaggataaat aatctcaaga tcactaaatt    480

aatatcccta accaaataca agataaaatg tgtcccacaa ttataactcc ctatatccca    540

ctttatacga cacttttcag atttcgacat tcaaacaatt ctattttttta ccgtaaaaaa   600

tatcatatct tgaattatca atacaaatat ataatttcat ttaattttta aaaaagattc    660

cattagtaaa ttttcaatta agcttaaact aaacagaaaa aaaatatctc ttatccatcg    720

taccaaacga caccagaaca taaaaattaa aaaacctaga aagtaaatga actagtatcc    780
```

```
caaaaaggtt aatagtagtc cagtcattca aaagatcagt gatcacatga tgtactagca    840
aacctacata cacagtggaa tatatctact gctccataag aaattatttc atcatttctc    900
taagagttat gaattatttt attattattt ttctttctcc atctccatat attgttggag    960
ttggaaacta atataaagta aattaaacca ttatattata atgtctggcg tatggatatt   1020
tgacaagaaa ggtgttgccc atttgatcaa aaatcctact cgtgaatcct tcgagctaaa   1080
acaaccaaca catccaggta tatgtcactc gatataagtt taactcattc gattcagtaa   1140
ttaatactac acattctcct ttgacgatat atggagacta cactatatat tatatgtgtt   1200
ttatgttttt atgtatttgt taggggttaa ttagtccgtt acatgctgat tgcagtaata   1260
gagttaggtt tttcattaag aaaaatcaaa attaaaaaat atgtaaatat agaaaaaaaa   1320
tcaaggtgat tcaaaaagga gttgtaatct cacgtatata tagtgaaatt tatttctaag   1380
gaggtttgaa tatcgaaacc tagttgcacc cataattaca acctttaatt ttggatcgtg   1440
acagatatga tattagaaca tagtttattg gtttcaacaa ggaattgaca acataagctt   1500
taagtcaagg caaaatgtat atattatctt ccttcatgac attttgtact cgtactgact   1560
ctaaattctg tattcgtcct tgtaggcacg ggtacagcca cagcaccggg ggcacgccct   1620
cgagtgttgg tgtacctacc agagaatgag atgataggtt cctatgaaga actagagaag   1680
agactcattg aaatcgggtg gacccgattc aacaacccga tgaagtcgga tcttctgcag   1740
tttcataaat cagatgattc tgcacatctc atttcacttc caaagagctt tacaaacttc   1800
aactcacaca atatgtatga cattgtggtc aagaatccat cggtttttga agttcgtgat   1860
gttaaagtgt gtgatcatct tatatgaaac ttaaattatt aaagtaaaca tacgtaatta   1920
tgttatttct cctctttcgt atctgagctt gattcttttt cattagccaa atacgtggat   1980
ttatatgttt tttcgctctt tggttggtgg agagatttgg aacctagcta gcatatctcg   2040
tgcctattct gataacatat tgaattgtat acatgatcgt ttcatctaaa aattaagcat   2100
ttaaaaatca catttttaat tacttaacta attatatagt tatattatgt gttaacacat   2160
accttgcata tatgagtttg attcttcttc atgaccagaa aatgtcaaat atatttttgc   2220
tttttgagcc ggaactctta catgctccat ttgataacaa gttggaatgt gtggttatct   2280
tatataaaaa caacacaagt tgttatgaaa agcatattta taattattaa tctaattata   2340
ttatgtttta acacagtttt ttatatgtga atttgattct ttttcattgg gcaaacatgt   2400
gtgaaacaat ttattttttt atagactagg atgatagaga aatttgaact taaaatctct   2460
catgtgttcg aataacatat tataaagtat gctatcattc atttaaaatt taacttatta   2520
gaaaataata cacttttttt tacttaatta taatgtgact cttcgttttg gccataataa   2580
aagtctattt gaattgattt ttgacttttg attttcaagt caatgtttga attatttttg   2640
atgtttttag cttaaagcaa atggtttgtg cgtccaaaaa atatttgaaa ctattttaac   2700
ttaaaatcac ttaaaacaag tcgatccatg taacatgcaa gttttgacct aattagaagg   2760
tttgaaatta tacctagcta gagctatcta tttcttttat tatcaatttt tttaatatat   2820
catagttcta tattaatatt tttttgcttt ctcgata                            2857
```

<210> SEQ ID NO 12
<211> LENGTH: 887
<212> TYPE: DNA
<213> ORGANISM: Solanum lycopersicum

<400> SEQUENCE: 12

```
atgtctggcg tatggatatt tgacaagaaa ggtgttgccc atttgatcaa aaatcctact     60
```

-continued

```
cgtgaatcct tcgagctaaa acaaccaaca catccaggta tatgtcactc gatataagtt    120

taactcattc gattcagtaa ttaatactac acattctcct ttgacgatat atggagacta    180

cactatatat tatatgtgtt ttatgttttt atgtatttgt taggggttaa ttagtccgtt    240

acatgctgat tgcagtaata gagttaggtt tttcattaag aaaaatcaaa attaaaaaat    300

atgtaaatat agaaaaaaaa tcaaggtgat tcaaaaagga gttgtaatct cacgtatata    360

tagtgaaatt tatttctaag gaggtttgaa tatcgaaacc tagttgcacc cataattaca    420

acctttaatt ttggatcgtg acagatatga tattagaaca tagtttattg gtttcaacaa    480

ggaattgaca acataagctt taagtcaagg caaaatgtat atattatctt ccttcatgac    540

attttgtact cgtactgact ctaaattctg tattcgtcct tgtaggcacg ggtacagcca    600

cagcaccggg ggcacgccct cgagtgttgg tgtacctacc agagaatgag atgataggtt    660

cctatgaaga actagagaag agactcattg aaatcgggtg gacccgattc aacaacccga    720

tgaagtcgga tcttctgcag tttcataaat cagatgattc tgcacatctc atttcacttc    780

caaagagctt tacaaacttc aactcacaca atatgtatga cattgtggtc aagaatccat    840

cggtttttga agttcgtgat gttaaagtgt gtgatcatct tatatga                887
```

<210> SEQ ID NO 13
<211> LENGTH: 132
<212> TYPE: PRT
<213> ORGANISM: Solanum lycopersicum

<400> SEQUENCE: 13

```
Met Ser Gly Val Trp Ile Phe Asp Lys Lys Gly Val Ala His Leu Ile
1               5                   10                  15

Lys Asn Pro Thr Arg Glu Ser Phe Glu Leu Lys Gln Pro Thr His Pro
            20                  25                  30

Gly Thr Gly Thr Ala Thr Ala Pro Gly Ala Arg Pro Arg Val Leu Val
        35                  40                  45

Tyr Leu Pro Glu Asn Glu Met Ile Gly Ser Tyr Glu Glu Leu Glu Lys
    50                  55                  60

Arg Leu Ile Glu Ile Gly Trp Thr Arg Phe Asn Asn Pro Met Lys Ser
65                  70                  75                  80

Asp Leu Leu Gln Phe His Lys Ser Asp Asp Ser Ala His Leu Ile Ser
                85                  90                  95

Leu Pro Lys Ser Phe Thr Asn Phe Asn Ser His Asn Met Tyr Asp Ile
            100                 105                 110

Val Val Lys Asn Pro Ser Val Phe Glu Val Arg Asp Val Lys Val Cys
        115                 120                 125

Asp His Leu Ile
    130
```

<210> SEQ ID NO 14
<211> LENGTH: 20
<212> TYPE: DNA
<213> ORGANISM: Artificial Sequence
<220> FEATURE:
<223> OTHER INFORMATION: gRNA sequence

<400> SEQUENCE: 14

```
agagactcat tgaaatcggg                                                 20
```

<210> SEQ ID NO 15
<211> LENGTH: 20

<212> TYPE: DNA
<213> ORGANISM: Artificial Sequence
<220> FEATURE:
<223> OTHER INFORMATION: gRNA sequence

<400> SEQUENCE: 15
agaagagact cattgaaatc 20

<210> SEQ ID NO 16
<211> LENGTH: 2227
<212> TYPE: DNA
<213> ORGANISM: Solanum lycopersicum

<400> SEQUENCE: 16
aagttttgaa ttctttaggt tgctttttct ttaatttttt tcttcttctc atatcatgaa 60
tcttatccat ttcaatattt ccaccaaaca tgggacatgg acatctctat gagttcatct 120
tcttgcttcc aatgcattat ctggtgtttg atattcgtat tgagcttcca ctaattcaga 180
ttcatgccgc ataaagtcta tttaaaagaa aaatatttct atcaaaattg ttttcatact 240
ctagggtcga gcaaagggat tcatgaccaa tgatatctac gggaatatta aagaatcttg 300
ataaagaaca cttctccttg tccgagcctt tgacaaaaat catttttggt aggattgctt 360
ccccaccttt cagtcttatg tagaatttga attagttgag attcactatg aatatcgaat 420
aaataacaaa aaaaaaaagg agtaatgaat ctttccaaat atagaatata ttatgattaa 480
atgcatgcat gggaagcaaa aagatgaact tatggagatg tgtcatgtcc catatatttg 540
atggaaatat tgggttggat aagattcatg atgaaaaaaa aaagcggtga cataaatctg 600
aattagtcgg aactccaaat agtttaattt gtttttgaaa aataaccttc ttttacttgc 660
cctttccttt tttatctctt caaaaaataa aaataaaact tcttaccaca atttatacta 720
tatattactt attaagggga atcttgatgc aataacataa cacagttatc tttatcagat 780
tcgaaccgta gaagcagcta caaatatttg taataaggaa ggctatttac atcacacatg 840
tatttatacg tatatggact tatttattta tttatatata tatatatata tatatgcata 900
tcacaccatg cattaaccct ataaaaccca cacattatat tctttttcaa caacaccatc 960
ttttacatat attcaacttc ccctccctct atccctcatc atgtcaggtg tttggatttt 1020
caaaaacggc gtcgtccggc tagaaacccc cggtgactgc cacgtcagct ccacgaccgg 1080
tcatcggaaa gttctagtac atgttcctag taaagaagtc attacatgtt atgcaaatct 1140
tgaaaaaaag ctttatagtc ttggatggga aaggtattat gatgatccac aacttcttca 1200
ataccacaaa agatccacaa ttcatcttat ttccctccca attgatttta ataggtttaa 1260
atccattcat atgtatgata ttgttgttaa aaatcgaaat gaatttgaag ttagagatat 1320
gtaaagttac taactttctt tacgtggata taagaaatgt gaaatttgga gaaacttatg 1380
tgttttcgag ttgatagtga tatgtttgga gattggagtt gtgtttgaac atggatacga 1440
acggaattgt ttttgaattt ttgaaagtga aaattgcttt ttattgtttt tgaacttaaa 1500
attgttatgt ggctaacaaa ataaaatcaa tcaacaaaca agtcgttgta gtatagtggt 1560
aagtattccc gcctgtcacg cgggtgaccc gggttcgatc cccggcaacg gcgttaattt 1620
tttttatgtt tctacacata ccatatatct agttatatct tacgacaagc acaaatacat 1680
tatgctctcg caacatacaa tgtatctagt tatatatctt acgagaagca caaatacatt 1740
atgctctcgc aacatacaat atatccagtt gtgtcttacg acaagtactc caaaacccac 1800
caacgctcga gaaatgcctt gttatggtgt aagaaacatc agcttcagta tgttaagact 1860

-continued gataacaaag gagttacttc acaagttctt tttcaacaag taatttacat agagtttgga 1920
tgttgtgttc tggacaacaa gaaaaaatga atgtagttag tctaaggcta tgttgcttgg 1980
actctccaaa agatgctaca cccgtgtcgg gtcctccaaa aatgcactac ttttgaagga 2040
tcagacatgc acgtgtcgcc atatttcaag agcccgagca acataggttc aaggaactca 2100
tatgatatag gctaatgtca cgaactcact ttcttctttg tcgtgctcca aatgtttcag 2160
ctctgaacct atacattccg ccatccaata tatctcctca gtccgcgggt gagacttgtc 2220
atccgat 2227

<210> SEQ ID NO 17
<211> LENGTH: 324
<212> TYPE: DNA
<213> ORGANISM: Solanum lycopersicum

<400> SEQUENCE: 17
atgtcaggtg tttggatttt caaaaacggc gtcgtccggc tagaaacccc cggtgactgc 60
cacgtcagct ccacgaccgg tcatcggaaa gttctagtac atgttcctag taaagaagtc 120
attacatgtt atgcaaatct tgaaaaaaag ctttatagtc ttggatggga aaggtattat 180
gatgatccac aacttcttca ataccacaaa agatccacaa ttcatcttat ttccctccca 240
attgatttta ataggtttaa atccattcat atgtatgata ttgttgttaa aaatcgaaat 300
gaatttgaag ttagagatat gtaa 324

<210> SEQ ID NO 18
<211> LENGTH: 107
<212> TYPE: PRT
<213> ORGANISM: Solanum lycopersicum

<400> SEQUENCE: 18

Met Ser Gly Val Trp Ile Phe Lys Asn Gly Val Val Arg Leu Glu Thr
1               5                   10                  15

Pro Gly Asp Cys His Val Ser Ser Thr Thr Gly His Arg Lys Val Leu
            20                  25                  30

Val His Val Pro Ser Lys Glu Val Ile Thr Cys Tyr Ala Asn Leu Glu
        35                  40                  45

Lys Lys Leu Tyr Ser Leu Gly Trp Glu Arg Tyr Tyr Asp Asp Pro Gln
    50                  55                  60

Leu Leu Gln Tyr His Lys Arg Ser Thr Ile His Leu Ile Ser Leu Pro
65                  70                  75                  80

Ile Asp Phe Asn Arg Phe Lys Ser Ile His Met Tyr Asp Ile Val Val
                85                  90                  95

Lys Asn Arg Asn Glu Phe Glu Val Arg Asp Met
            100                 105

<210> SEQ ID NO 19
<211> LENGTH: 20
<212> TYPE: DNA
<213> ORGANISM: Artificial Sequence
<220> FEATURE:
<223> OTHER INFORMATION: gRNA sequence

<400> SEQUENCE: 19
ccctcatcat gtcaggtgtt 20

<210> SEQ ID NO 20
<211> LENGTH: 20
<212> TYPE: DNA

<213> ORGANISM: Artificial Sequence
<220> FEATURE:
<223> OTHER INFORMATION: gRNA sequence

<400> SEQUENCE: 20
ttttcaaaaa cggcgtcgtc 20

<210> SEQ ID NO 21
<211> LENGTH: 315
<212> TYPE: DNA
<213> ORGANISM: Solanum lycopersicum

<400> SEQUENCE: 21
atgtctggag tttgggtatt caagaatggt gttgtccgtc tagtggagaa ctccgattgc 60
cacggggcga acggactccg aaaagttctt gtacatcttc ctagtaatga agtcatcaca 120
tcatatgcag tacttgaaag gaaactgtac tctcttggat gggagaggta ctatgatgaa 180
cctgaacttc ttcaatacca caaaagatca accgttcatc ttatttctct accaaaggat 240
ttcaacaggt tcaaatccat gcatatgttc gatatcgtcg tcaagaatcg caatgaattt 300
gaggttagag atatg 315

<210> SEQ ID NO 22
<211> LENGTH: 105
<212> TYPE: PRT
<213> ORGANISM: Solanum lycopersicum

<400> SEQUENCE: 22

Met Ser Gly Val Trp Val Phe Lys Asn Gly Val Val Arg Leu Val Glu
1 5 10 15

Asn Ser Asp Cys His Gly Ala Asn Gly Leu Arg Lys Val Leu Val His
20 25 30

Leu Pro Ser Asn Glu Val Ile Thr Ser Tyr Ala Val Leu Glu Arg Lys
35 40 45

Leu Tyr Ser Leu Gly Trp Glu Arg Tyr Tyr Asp Glu Pro Glu Leu Leu
50 55 60

Gln Tyr His Lys Arg Ser Thr Val His Leu Ile Ser Leu Pro Lys Asp
65 70 75 80

Phe Asn Arg Phe Lys Ser Met His Met Phe Asp Ile Val Val Lys Asn
85 90 95

Arg Asn Glu Phe Glu Val Arg Asp Met
100 105

<210> SEQ ID NO 23
<211> LENGTH: 26
<212> TYPE: DNA
<213> ORGANISM: Solanum lycopersicum

<400> SEQUENCE: 23
ttttatggaa ttgaagaagg tcaggg 26

<210> SEQ ID NO 24
<211> LENGTH: 22
<212> TYPE: DNA
<213> ORGANISM: Artificial Sequence
<220> FEATURE:
<223> OTHER INFORMATION: disrupted locus sequence

<400> SEQUENCE: 24
ttttatggaa ttgaggtcag gg 22

<210> SEQ ID NO 25
<211> LENGTH: 27
<212> TYPE: DNA
<213> ORGANISM: Solanum lycopersicum

<400> SEQUENCE: 25
ccccggtgac ttccacggtg cgacggg 27

<210> SEQ ID NO 26
<211> LENGTH: 22
<212> TYPE: DNA
<213> ORGANISM: Artificial Sequence
<220> FEATURE:
<223> OTHER INFORMATION: disrupted locus sequence

<400> SEQUENCE: 26
ccccggtcca cggtgcgacg gg 22

<210> SEQ ID NO 27
<211> LENGTH: 27
<212> TYPE: DNA
<213> ORGANISM: Solanum lycopersicum

<400> SEQUENCE: 27
cctcggtgac tttcacggtg cgacggg 27

<210> SEQ ID NO 28
<211> LENGTH: 22
<212> TYPE: DNA
<213> ORGANISM: Artificial Sequence
<220> FEATURE:
<223> OTHER INFORMATION: disrupted locus sequence

<400> SEQUENCE: 28
ccccggttca cggtgcgacg gg 22

<210> SEQ ID NO 29
<211> LENGTH: 108
<212> TYPE: PRT
<213> ORGANISM: Nicotiana benthamiana

<400> SEQUENCE: 29

```
Met Ser Gly Val Trp Ile Phe Asp Lys Lys Gly Val Ala Arg Leu Ile
1               5                   10                  15

Thr Asn Pro Thr Arg Glu Ser Phe Asp Leu Met Gln Pro Thr Ser Ser
            20                  25                  30

Gly Thr Gly Thr Ala Pro Gly Ala Arg Pro Lys Val Leu Val Tyr Leu
        35                  40                  45

Pro Glu Asn Gln Val Ile Ser Ser Tyr Ala Asp Leu Glu Lys Ile Leu
    50                  55                  60

Ile Glu Leu Gly Trp Ser Arg Tyr Asn Asn Pro Ile Arg Leu Asp Phe
65                  70                  75                  80

Met Gln Phe His Lys Ser Asp Asp Ser Ala His Leu Ile Ser Leu Pro
                85                  90                  95

Lys Glu Phe Thr Asn Phe Lys Ser Leu His Ile Glu
            100                 105
```

<210> SEQ ID NO 30
<211> LENGTH: 130
<212> TYPE: PRT
<213> ORGANISM: Petunia axillaris

<400> SEQUENCE: 30

Met Ser Gly Val Trp Ile Phe Asp Lys Lys Gly Val Ala His Leu Ile
1 5 10 15

Lys Asn Pro Thr Arg Glu Ser Phe Glu Leu Lys Glu Pro Thr Tyr Pro
20 25 30

Gly Thr Gly Thr Ala Thr Ala Pro Gly Ala Arg Pro Lys Val Leu Val
35 40 45

Tyr Leu Pro Glu Asn Glu Val Ile Ser Ser Tyr Asp Glu Leu Glu Lys
50 55 60

Ile Leu Val Glu Leu Gly Trp Ser Arg Tyr Asn Asn Pro Thr Arg Ser
65 70 75 80

Asp Leu Leu Gln Phe His Lys Ser Asp Asp Ser Ala His Leu Ile Ser
85 90 95

Leu Pro Ile Ser Phe Thr Asn Phe Lys Pro Leu His Met Tyr Asp Ile
100 105 110

Val Val Lys Asn Arg Ser Phe Phe Glu Val Arg Asp Ser Pro Tyr Thr
115 120 125

Ser Tyr
130

<210> SEQ ID NO 31
<211> LENGTH: 130
<212> TYPE: PRT
<213> ORGANISM: Petunia inflata

<400> SEQUENCE: 31

Met Ser Gly Val Trp Ile Phe Asp Lys Lys Gly Val Ala His Leu Ile
1 5 10 15

Lys Asn Pro Thr Arg Glu Ser Phe Glu Leu Asn Glu Pro Thr Tyr Pro
20 25 30

Gly Thr Gly Thr Ala Thr Ala Pro Gly Ala Arg Pro Lys Ala Leu Val
35 40 45

Tyr Leu Pro Glu Asn Glu Val Ile Ser Ser Tyr Asp Glu Leu Glu Lys
50 55 60

Ile Leu Ile Glu Leu Gly Trp Ser Arg Tyr Asn Ser Pro Thr Arg Ser
65 70 75 80

Asp Leu Leu Gln Phe His Lys Ser Asn Asp Ser Gly His Leu Ile Ser
85 90 95

Leu Pro Ile Ser Phe Thr Asn Phe Lys Pro Leu His Met Tyr Asp Ile
100 105 110

Val Val Lys Asn Arg Ser Phe Phe Glu Val Arg Asp Ser Pro Tyr Thr
115 120 125

Ser Tyr
130

<210> SEQ ID NO 32
<211> LENGTH: 132
<212> TYPE: PRT
<213> ORGANISM: Capsicum annuum Zunla

<400> SEQUENCE: 32

Met Ser Gly Val Trp Ile Phe Asp Lys Lys Gly Val Ala His Leu Ile
1 5 10 15

Lys Asn Pro Thr Arg Glu Ser Phe Glu Leu Lys Gln Pro Ala Tyr Pro
20 25 30

Gly Thr Gly Thr Ala Thr Ala Pro Gly Ala Arg Pro Arg Val Leu Val

```
        35                  40                  45

Tyr Leu Pro Glu Asn Glu Met Ile Ser Ser Tyr Glu Glu Leu Glu Arg
    50                  55                  60

Arg Leu Ile Glu Leu Gly Trp Thr Arg Phe Asn Asn Pro Met Arg Ser
65                  70                  75                  80

Asp Leu Leu Gln Phe His Lys Ser Asp Asp Ser Ala His Leu Ile Ser
                85                  90                  95

Leu Pro Lys Ser Phe Thr Asp Phe Lys Ser Leu His Met Tyr Asp Ile
            100                 105                 110

Val Val Lys Asn Pro Ser Phe Phe Glu Val Arg Asn Ala Glu Val Asp
        115                 120                 125

Asn His Leu Ile
    130


<210> SEQ ID NO 33
<211> LENGTH: 132
<212> TYPE: PRT
<213> ORGANISM: Capsicum annuum Zunla

<400> SEQUENCE: 33

Met Ser Gly Val Trp Ile Phe Asp Lys Lys Gly Val Ala His Leu Ile
1               5                   10                  15

Lys Asn Pro Thr Arg Glu Ser Phe Glu Leu Lys Gln Pro Ala Tyr Pro
            20                  25                  30

Gly Thr Gly Thr Ala Thr Ala Pro Gly Ala Arg Pro Arg Val Leu Val
        35                  40                  45

Tyr Leu Pro Glu Asn Glu Met Ile Ser Ser Tyr Glu Glu Leu Glu Arg
    50                  55                  60

Arg Leu Ile Glu Leu Gly Trp Thr Arg Phe Asn Asn Pro Met Arg Ser
65                  70                  75                  80

Asp Leu Leu Gln Phe His Lys Ser Asp Asp Ser Ala His Leu Ile Ser
                85                  90                  95

Leu Pro Lys Ser Phe Thr Asn Phe Lys Ser Leu His Met Tyr Asp Ile
            100                 105                 110

Val Val Lys Asn Pro Ser Phe Phe Glu Val Arg Asn Ala Glu Val Asp
        115                 120                 125

Asn His Leu Ile
    130


<210> SEQ ID NO 34
<211> LENGTH: 100
<212> TYPE: PRT
<213> ORGANISM: Capsicum annuum

<400> SEQUENCE: 34

Gly Thr Gly Thr Ala Thr Ala Pro Gly Ala Arg Pro Arg Val Leu Val
1               5                   10                  15

Tyr Leu Pro Glu Asn Glu Met Ile Ser Ser Tyr Glu Glu Leu Glu Arg
            20                  25                  30

Arg Leu Ile Glu Leu Gly Trp Thr Arg Phe Asn Asn Pro Met Arg Ser
        35                  40                  45

Asp Leu Leu Gln Phe His Lys Ser Asp Asp Ser Ala His Leu Ile Ser
    50                  55                  60

Leu Pro Lys Ser Phe Thr Asn Phe Lys Ser Leu His Met Tyr Asp Ile
65                  70                  75                  80

Val Val Lys Asn Pro Ser Phe Phe Glu Val Arg Asn Ala Glu Val Asp
```

```
                85                  90                  95

Asn His Leu Ile
            100


<210> SEQ ID NO 35
<211> LENGTH: 132
<212> TYPE: PRT
<213> ORGANISM: Solanum melongena

<400> SEQUENCE: 35

Met Ser Gly Val Trp Ile Phe Asp Lys Lys Gly Val Ala His Leu Ile
1               5                   10                  15

Lys Asn Pro Thr Arg Glu Ser Phe Glu Leu Lys Gln Ser Thr Tyr Pro
            20                  25                  30

Gly Thr Gly Thr Ala Thr Ala Pro Gly Ala Arg Pro Arg Val Leu Val
        35                  40                  45

Tyr Leu Pro Glu Asn Glu Ile Ile Ser Ser Tyr Glu Glu Leu Glu Arg
    50                  55                  60

Arg Leu Ile Glu Leu Gly Trp Thr Arg Phe Asn Asn Pro Met Lys Ser
65                  70                  75                  80

Asp Leu Leu Gln Phe His Lys Ser Asp Asp Ser Ala His Leu Ile Ser
                85                  90                  95

Leu Pro Lys Ser Phe Thr Asn Phe Lys Ser Leu Gln Met Tyr Asp Ile
            100                 105                 110

Val Val Lys Asn Pro Ser Phe Phe Glu Val Arg Asp Ile Lys Val Tyr
        115                 120                 125

Asp His Pro Ile
    130


<210> SEQ ID NO 36
<211> LENGTH: 132
<212> TYPE: PRT
<213> ORGANISM: Solanum tuberosum

<400> SEQUENCE: 36

Met Ser Gly Val Trp Ile Phe Asp Lys Lys Gly Val Ala His Leu Ile
1               5                   10                  15

Lys Asn Pro Thr Arg Glu Ser Phe Glu Leu Lys Gln Pro Thr Tyr Pro
            20                  25                  30

Gly Thr Gly Thr Val Thr Ala Pro Gly Ala Arg Pro Arg Val Leu Val
        35                  40                  45

Tyr Leu Pro Glu Asn Glu Met Ile Ser Ser Tyr Glu Glu Leu Glu Lys
    50                  55                  60

Arg Leu Ile Glu Leu Gly Trp Thr Arg Phe Asn Asn Pro Met Lys Ser
65                  70                  75                  80

Asp Leu Leu Gln Phe His Lys Ser Asp Asp Ser Ala His Leu Ile Ser
                85                  90                  95

Leu Pro Lys Ser Phe Thr Asn Phe Lys Ser His Gln Met Tyr Asp Ile
            100                 105                 110

Val Val Lys Asn Pro Ser Ile Phe Glu Val Arg Asp Val Lys Val Cys
        115                 120                 125

Asp His Leu Ile
    130


<210> SEQ ID NO 37
<211> LENGTH: 132
<212> TYPE: PRT
```

-continued

<213> ORGANISM: Solanum pennellii

<400> SEQUENCE: 37

```
Met Ser Gly Val Trp Ile Phe Asp Lys Lys Gly Val Ala His Leu Ile
1               5                   10                  15

Lys Asn Pro Thr Arg Glu Ser Phe Glu Leu Lys Gln Pro Thr His Pro
            20                  25                  30

Gly Thr Gly Thr Ala Thr Ala Pro Gly Ala Arg Pro Arg Val Leu Val
        35                  40                  45

Tyr Leu Pro Glu Asn Glu Met Ile Gly Ser Tyr Glu Glu Leu Glu Lys
    50                  55                  60

Arg Leu Ile Glu Ile Gly Trp Thr Arg Phe Asn Asn Pro Met Lys Ser
65                  70                  75                  80

Asp Leu Leu Gln Phe His Lys Ser Asp Asp Ser Ala His Leu Ile Ser
                85                  90                  95

Leu Pro Lys Ser Phe Thr Asn Phe Asn Ser His Asn Met Tyr Asp Ile
            100                 105                 110

Val Val Lys Asn Pro Ser Val Phe Glu Val Arg Asp Val Lys Val Cys
        115                 120                 125

Asp His Leu Ile
    130
```

<210> SEQ ID NO 38
<211> LENGTH: 123
<212> TYPE: PRT
<213> ORGANISM: Solanum lycopersicum

<400> SEQUENCE: 38

```
Met Ser Gly Val Trp Ile Phe Asp Lys Lys Gly Val Ala His Leu Ile
1               5                   10                  15

Lys Asn Pro Thr Arg Glu Ser Phe Glu Leu Lys Gln Pro Thr His Pro
            20                  25                  30

Gly Thr Gly Thr Ala Thr Ala Pro Gly Ala Arg Pro Arg Val Leu Val
        35                  40                  45

Tyr Leu Pro Glu Asn Glu Met Ile Gly Ser Tyr Glu Glu Leu Glu Lys
    50                  55                  60

Arg Leu Ile Glu Ile Gly Trp Thr Arg Phe Asn Asn Pro Met Lys Ser
65                  70                  75                  80

Asp Leu Leu Gln Phe His Lys Ser Asp Asp Ser Ala His Leu Ile Ser
                85                  90                  95

Leu Pro Lys Ser Phe Thr Asn Phe Asn Ser His Asn Met Tyr Asp Ile
            100                 105                 110

Val Val Lys Asn Pro Ser Val Phe Glu Val Arg
        115                 120
```

<210> SEQ ID NO 39
<211> LENGTH: 111
<212> TYPE: PRT
<213> ORGANISM: Nicotiana benthamiana

<400> SEQUENCE: 39

```
Met Ser Gly Val Trp Leu Ser Lys Asn Thr Gly Val Ile Arg Leu Leu
1               5                   10                  15

Glu Asn Gln Thr Glu Glu Glu Gln Ser Ile Gly Arg Lys Arg Lys Val
            20                  25                  30

Leu Val His Leu Pro Thr Gln Glu Ile Val Ser Ser Tyr Asn Ser Leu
        35                  40                  45
```

-continued

Asp Lys Ile Leu Thr Asp Leu Gly Trp Glu Lys Tyr Asp Cys Gly Asp
50 55 60

Asp Pro His Phe Tyr Gln Phe His Lys Arg Thr Pro Ile His Leu Ser
65 70 75 80

Leu Ser Leu Pro Asn Asp Phe Ala Lys Phe Asn Thr Val Gln Met Tyr
85 90 95

Asp Ile Val Phe Lys Thr Arg His Ile Phe His Val Arg Tyr Ile
100 105 110

<210> SEQ ID NO 40
<211> LENGTH: 72
<212> TYPE: PRT
<213> ORGANISM: Petunia inflata

<400> SEQUENCE: 40

Met Ser Gly Val Trp Val Phe Lys Asn Gly Val Phe Arg Leu Val Glu
1 5 10 15

Asn Pro Gly Ala Glu Gln Ala Gln Arg Arg Arg Lys Val Leu Val His
20 25 30

Leu Pro Thr Gly Gln Met Val Ser Ser Tyr Cys Ser Leu Glu Arg Ile
35 40 45

Leu Asn Gly Leu Gly Trp Glu Arg Val Gln Glu Ile Val Leu Lys Tyr
50 55 60

Cys Val Gly Ile Lys Leu Ser His
65 70

<210> SEQ ID NO 41
<211> LENGTH: 106
<212> TYPE: PRT
<213> ORGANISM: Petunia axillaris

<400> SEQUENCE: 41

Met Ser Gly Val Trp Val Phe Lys Asn Gly Val Phe Arg Leu Val Glu
1 5 10 15

Asn Pro Gly Ala Glu Gln Ala Gln Arg Arg Arg Lys Val Leu Val His
20 25 30

Leu Pro Thr Gly Gln Met Val Ser Ser Tyr Cys Ser Leu Glu Arg Ile
35 40 45

Leu Asn Gly Leu Gly Trp Glu Arg Tyr Tyr Gly Gly Asp Pro Glu Leu
50 55 60

Phe Gln Phe His Lys His Ser Ser Ile Asp Leu Ile Ser Leu Pro Lys
65 70 75 80

Asp Phe Ser Lys Phe Asn Ser Ile His Met Tyr Asp Ile Val Val Lys
85 90 95

Asn Pro Asn Val Phe His Val Arg Asp Ala
100 105

<210> SEQ ID NO 42
<211> LENGTH: 106
<212> TYPE: PRT
<213> ORGANISM: Solanum melongena

<400> SEQUENCE: 42

Met Ser Gly Val Trp Val Phe Lys Asn Gly Val Phe Arg Leu Val Glu
1 5 10 15

Asn Gly Ser Gly Asp Gln Ala Gln Arg Arg Arg Lys Val Leu Ile His
20 25 30

```
Leu Pro Ser Gly Gln Val Val Ser Ser Tyr Cys Ser Leu Glu Arg Ile
        35                  40                  45

Leu Asn Asp Leu Gly Trp Glu Arg Tyr Tyr Glu Gly Asp Ala Glu Leu
    50                  55                  60

Phe Gln Phe His Lys His Ser Ser Ile Asp Leu Ile Ser Leu Pro Met
65                  70                  75                  80

Asp Phe Thr Lys Phe Asn Ser Ile His Met Tyr Asp Ile Val Val Lys
                85                  90                  95

Asn Pro Asn Ile Phe His Val Arg Asp Val
            100                 105


<210> SEQ ID NO 43
<211> LENGTH: 106
<212> TYPE: PRT
<213> ORGANISM: Capsicum annuum Zunla

<400> SEQUENCE: 43

Met Ser Gly Val Trp Val Phe Lys Asn Gly Val Phe Arg Leu Val Glu
1               5                   10                  15

Asn Gly Ser Gly Asp Gln Ala Gln Arg Arg Arg Lys Val Leu Leu His
            20                  25                  30

Leu Pro Ser Gly Gln Val Val Ser Ser Tyr Cys Ser Leu Glu Arg Ile
        35                  40                  45

Leu Asn Gly Leu Gly Trp Glu Arg Tyr Tyr Gly Gly Asp Thr Glu Leu
    50                  55                  60

Phe Gln Phe His Lys His Ser Ser Ile Asp Leu Ile Ser Leu Pro Lys
65                  70                  75                  80

Asp Phe Ala Lys Phe Asn Ser Ile His Met Tyr Asp Ile Val Val Lys
                85                  90                  95

Asn Pro Asn Val Phe His Val Arg Asp Val
            100                 105


<210> SEQ ID NO 44
<211> LENGTH: 122
<212> TYPE: PRT
<213> ORGANISM: Capsicum annuum

<400> SEQUENCE: 44

Leu Ile Phe Glu Lys Glu His Thr His Thr His Thr Ser Glu Val Glu
1               5                   10                  15

Met Ser Gly Val Trp Val Phe Lys Asn Gly Val Phe Arg Leu Val Glu
            20                  25                  30

Asn Gly Ser Gly Asp Gln Ala Gln Arg Arg Arg Lys Val Leu Leu His
        35                  40                  45

Leu Pro Ser Gly Gln Val Val Ser Ser Tyr Cys Ser Leu Glu Arg Ile
    50                  55                  60

Leu Asn Gly Leu Gly Trp Glu Arg Tyr Tyr Gly Gly Asp Thr Glu Leu
65                  70                  75                  80

Phe Gln Phe His Lys His Ser Ser Ile Asp Leu Ile Ser Leu Pro Lys
                85                  90                  95

Asp Phe Ala Lys Phe Asn Ser Ile His Met Tyr Asp Ile Val Val Lys
            100                 105                 110

Asn Pro Asn Val Phe His Val Arg Asp Val
        115                 120


<210> SEQ ID NO 45
<211> LENGTH: 106
```

<212> TYPE: PRT
<213> ORGANISM: Nicotiana benthamiana

<400> SEQUENCE: 45

Met Ser Gly Val Trp Val Phe Lys Asn Gly Val Phe Arg Leu Val Glu
1 5 10 15

Asn Pro Ser Ser Glu Gln Gly Gln Arg Arg Arg Lys Val Leu Val His
20 25 30

Leu Pro Thr Gly Gln Val Val Ser Ser Tyr Cys Ser Leu Glu Arg Ile
35 40 45

Leu Lys Gly Leu Gly Trp Glu Arg Tyr Tyr Gly Gly Asp Pro Glu Leu
50 55 60

Phe Gln Phe His Lys His Ser Ser Ile Asp Leu Ile Ser Leu Pro Lys
65 70 75 80

Glu Phe Ala Lys Phe Asn Ser Ile His Met Tyr Asp Ile Val Val Lys
85 90 95

Asn Pro Asn Val Phe His Val Arg Asp Ala
100 105

<210> SEQ ID NO 46
<211> LENGTH: 106
<212> TYPE: PRT
<213> ORGANISM: Nicotiana benthamiana

<400> SEQUENCE: 46

Met Ser Gly Val Trp Val Phe Lys Asn Gly Val Phe Arg Leu Val Glu
1 5 10 15

Asn Pro Ser Ser Glu Gln Gly Gln Arg Arg Arg Lys Val Leu Leu His
20 25 30

Leu Pro Thr Gly Gln Val Val Ser Ser Tyr Cys Ser Leu Glu Arg Ile
35 40 45

Leu Asn Gly Leu Gly Trp Glu Arg Tyr Tyr Gly Gly Asp Pro Glu Leu
50 55 60

Phe Gln Phe His Lys His Ser Ser Ile Asp Leu Ile Ser Leu Pro Lys
65 70 75 80

Asp Phe Ala Lys Phe Asn Ser Ile His Met Tyr Asp Ile Val Val Lys
85 90 95

Asn Pro Asn Val Phe His Val Arg Asp Val
100 105

<210> SEQ ID NO 47
<211> LENGTH: 113
<212> TYPE: PRT
<213> ORGANISM: Solanum pennellii

<400> SEQUENCE: 47

Met Pro Gly Val Trp Glu Ile Lys Asn Gly Val Val Arg Leu Val Glu
1 5 10 15

Lys Pro Gly Asp Ser His Gly Ala Thr Val Arg Asn Lys Val Leu Val
20 25 30

His Leu Ser Ser Asn Glu Val Ile Thr Ser Tyr Ala Ser Leu Glu Arg
35 40 45

Ile Leu Ile Ser Ile Gly Trp Glu Arg Tyr Tyr Asp Gly Asp Pro Asp
50 55 60

Leu Leu Gln Tyr His Lys Arg Ser Thr Val His Ile Ile Ser Leu Pro
65 70 75 80

Lys Asp Phe Lys Asn Phe Lys Phe Pro His Met Leu Asp Ile Val Leu

-continued

```
                85                  90                  95

Lys Asn Arg Asn Asp Phe Thr Thr Arg Asp Thr Ser Ile Thr Asn Asn
            100                 105                 110

Asn


<210> SEQ ID NO 48
<211> LENGTH: 104
<212> TYPE: PRT
<213> ORGANISM: Nicotiana benthamiana

<400> SEQUENCE: 48

Met Ser Gly Val Trp Val Phe Lys Asn Gly Val Leu Arg Leu Val Glu
1               5                   10                  15

Asn Pro Gly Asp His Phe Gln Gly Cys Arg Lys Val Leu Val His Ile
            20                  25                  30

Pro Thr Asn Glu Val Ile Thr Ser Tyr Ala Ile Leu Glu Thr Lys Leu
        35                  40                  45

Tyr Asn Leu Gly Trp Glu Arg Tyr Tyr Asp Asp Pro Glu Leu Leu Gln
    50                  55                  60

Tyr His Lys Arg Cys Thr Thr His Leu Ile Ser Leu Pro Lys Asp Phe
65                  70                  75                  80

Asn Lys Phe Lys Thr Met His Met Tyr Asp Ile Val Val Lys Asn Arg
                85                  90                  95

Asn Glu Phe Glu Val Arg Asp Met
            100


<210> SEQ ID NO 49
<211> LENGTH: 106
<212> TYPE: PRT
<213> ORGANISM: Solanum melongena

<400> SEQUENCE: 49

Met Ser Gly Val Trp Val Phe Lys Asn Gly Val Val Arg Leu Val Glu
1               5                   10                  15

Asn Thr Gly Asp Cys Gln Gly Ala Asn Gly Gly Arg Lys Val Leu Val
            20                  25                  30

His Val Pro Ser Asp Glu Val Ile Thr Ser Tyr Ala Val Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Arg Phe Lys Ser Met His Met Tyr Asp Ile Val Val Lys
                85                  90                  95

Asn Arg Asn Glu Phe Glu Val Arg Glu Met
            100                 105


<210> SEQ ID NO 50
<211> LENGTH: 105
<212> TYPE: PRT
<213> ORGANISM: Capsicum annuum Zunla

<400> SEQUENCE: 50

Met Ser Gly Val Trp Val Phe Lys Asn Gly Val Val Arg Leu Val Glu
1               5                   10                  15

Asn Gly Asp Cys Gln Gly Val Asn Gly Cys Arg Lys Val Leu Val His
            20                  25                  30
```

```
Leu Ala Ser Gly Glu Val Ile Thr Ser Tyr Ala Val Leu Glu Arg Lys
        35                  40                  45

Leu Tyr Ser Leu Gly Trp Glu Arg Tyr Tyr Asp Glu Pro Glu Leu Leu
    50                  55                  60

Gln Tyr His Lys Arg Ser Thr Val His Leu Ile Ser Leu Pro Lys Asp
65                  70                  75                  80

Phe Asn Arg Phe Lys Ser Met His Met Phe Asp Ile Val Val Lys Asn
                85                  90                  95

Arg Asn Glu Phe Glu Val Arg Asp Met
            100                 105


<210> SEQ ID NO 51
<211> LENGTH: 133
<212> TYPE: PRT
<213> ORGANISM: Solanum lycopersicum

<400> SEQUENCE: 51

Ser His His Lys Leu Gln Thr His Thr Lys Asn Ile Leu Ile His Leu
1               5                   10                  15

Ser Ser Thr Lys Asn Ile Thr Thr Ser Ser Thr Ile Met Ser Gly Val
            20                  25                  30

Trp Val Phe Lys Asn Gly Val Val Arg Leu Val Glu Asn Ser Asp Cys
        35                  40                  45

His Gly Ala Asn Gly Leu Arg Lys Val Leu Val His Leu Pro Ser Asn
    50                  55                  60

Glu Val Ile Thr Ser Tyr Ala Val Leu Glu Arg Lys Leu Tyr Ser Leu
65                  70                  75                  80

Gly Trp Glu Arg Tyr Tyr Asp Glu Pro Glu Leu Leu Gln Tyr His Lys
                85                  90                  95

Arg Ser Thr Val His Leu Ile Ser Leu Pro Lys Asp Phe Asn Arg Phe
            100                 105                 110

Lys Ser Met His Met Phe Asp Ile Val Val Lys Asn Arg Asn Glu Phe
        115                 120                 125

Glu Val Arg Asp Met
    130


<210> SEQ ID NO 52
<211> LENGTH: 105
<212> TYPE: PRT
<213> ORGANISM: Solanum pennellii

<400> SEQUENCE: 52

Met Ser Gly Val Trp Val Phe Lys Asn Gly Val Val Arg Leu Val Glu
1               5                   10                  15

Asn Ser Asp Cys His Gly Ala Asn Gly Leu Arg Lys Val Leu Val His
            20                  25                  30

Leu Pro Ser Asn Glu Val Ile Thr Ser Tyr Ala Val Leu Glu Arg Lys
        35                  40                  45

Leu Tyr Ser Leu Gly Trp Glu Arg Tyr Tyr Asp Glu Pro Glu Leu Leu
    50                  55                  60

Gln Tyr His Lys Lys Ser Thr Val His Leu Ile Ser Leu Pro Lys Asp
65                  70                  75                  80

Phe Asn Arg Phe Lys Ser Met His Met Phe Asp Ile Val Val Lys Asn
                85                  90                  95

Arg Asn Glu Phe Glu Val Arg Asp Met
            100                 105
```

<210> SEQ ID NO 53
<211> LENGTH: 105
<212> TYPE: PRT
<213> ORGANISM: Solanum pimpinellifolium

<400> SEQUENCE: 53

Met Ser Gly Val Trp Val Phe Lys Asn Gly Val Val Arg Leu Val Glu
1 5 10 15

Asn Ser Asp Cys His Gly Ala Asn Gly Leu Arg Lys Val Leu Val His
20 25 30

Leu Pro Ser Asn Glu Val Ile Thr Ser Tyr Ala Val Leu Glu Arg Lys
35 40 45

Leu Tyr Ser Leu Gly Trp Glu Arg Tyr Tyr Asp Glu Pro Glu Leu Leu
50 55 60

Gln Tyr His Lys Arg Ser Thr Val His Leu Ile Ser Leu Pro Lys Asp
65 70 75 80

Phe Asn Arg Phe Lys Ser Met His Met Phe Asp Ile Val Val Lys Asn
85 90 95

Arg Asn Glu Phe Glu Val Arg Asp Met
100 105

<210> SEQ ID NO 54
<211> LENGTH: 105
<212> TYPE: PRT
<213> ORGANISM: Solanum tuberosum

<400> SEQUENCE: 54

Met Ser Gly Val Trp Val Phe Lys Asn Gly Val Val Arg Leu Val Glu
1 5 10 15

Asn Ser Asp Cys His Gly Ala Asn Gly Leu Arg Lys Val Leu Val His
20 25 30

Leu Pro Ser Asp Glu Val Ile Thr Ser Tyr Ala Val Leu Glu Arg Lys
35 40 45

Leu Tyr Ser Leu Gly Trp Glu Arg Tyr Tyr Asp Glu Pro Glu Leu Leu
50 55 60

Gln Tyr His Lys Arg Ser Thr Val His Leu Ile Ser Leu Pro Lys Asp
65 70 75 80

Phe Asn Arg Phe Lys Ser Met His Met Phe Asp Ile Val Val Lys Asn
85 90 95

Arg Asn Glu Phe Glu Val Arg Asp Met
100 105

<210> SEQ ID NO 55
<211> LENGTH: 102
<212> TYPE: PRT
<213> ORGANISM: Nicotiana benthamiana

<400> SEQUENCE: 55

Met Ser Gly Val Trp Val Phe Lys Asn Gly Val Val Arg Leu Glu Asp
1 5 10 15

Cys Gln Gly Ser Ser Gly Arg Arg Lys Val Leu Val His Val Pro Ser
20 25 30

Asn Glu Val Ile Thr Ser Tyr Pro Val Leu Glu Arg Lys Leu Tyr Ser
35 40 45

Leu Gly Trp Glu Arg Tyr Tyr Asp Asp Leu Asn Leu Leu Gln Tyr His
50 55 60

Lys Arg Ser Thr Val His Leu Ile Ser Leu Pro Lys Asp Phe Asn Lys

-continued

```
65                  70                  75                  80

Phe Lys Ser Met His Met Tyr Asp Ile Val Val Lys Asn Arg Asn Glu
                85                  90                  95

Phe Glu Val Arg Asp Thr
            100


<210> SEQ ID NO 56
<211> LENGTH: 106
<212> TYPE: PRT
<213> ORGANISM: Petunia axillaris

<400> SEQUENCE: 56

Met Ser Gly Val Trp Val Phe Lys Asn Gly Val Val Arg Leu Val Glu
1               5                   10                  15

Asn Pro Gly Asp Cys Gln Gly Ser Ser Gly Arg Arg Lys Val Leu Val
            20                  25                  30

His Val Pro Thr Asn Glu Val Ile Thr Ser Tyr Ala Leu Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Lys Phe Lys Ser Ile His Met Tyr Asp Ile Val Val Lys
                85                  90                  95

Asn Arg Asn Glu Phe Glu Val Arg Asp Lys
            100                 105


<210> SEQ ID NO 57
<211> LENGTH: 106
<212> TYPE: PRT
<213> ORGANISM: Petunia inflata

<400> SEQUENCE: 57

Met Ser Gly Val Trp Val Phe Lys Asn Gly Val Val Arg Leu Val Glu
1               5                   10                  15

Asn Pro Gly Asp Cys Gln Gly Ser Ser Gly Arg Arg Lys Val Leu Val
            20                  25                  30

His Val Pro Thr Asn Glu Val Ile Thr Ser Tyr Ala Leu Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Lys Phe Lys Ser Ile Gln Met Tyr Asp Ile Val Val Lys
                85                  90                  95

Asn Arg Asn Glu Phe Glu Val Arg Asp Lys
            100                 105


<210> SEQ ID NO 58
<211> LENGTH: 198
<212> TYPE: PRT
<213> ORGANISM: Petunia axillaris

<400> SEQUENCE: 58

Met Ser Gly Val Trp Val Phe Lys Asn Gly Val Leu Arg Leu Val Glu
1               5                   10                  15

Asn Pro Gly Asp Asn Tyr His Gly Ser Arg Lys Val Leu Val His Val
            20                  25                  30
```

```
Pro Ser Asp Glu Val Ile Thr Ser Tyr Ala Ile Leu Glu Arg Lys Leu
        35                  40                  45

Tyr Asn Leu Gly Trp Glu Arg Tyr Tyr Asp Asp Pro Asn Leu Leu Gln
    50                  55                  60

Tyr His Lys Arg Ser Thr Val His Leu Ile Ser Leu Pro Arg Asp Phe
65                  70                  75                  80

Ser Lys Leu Lys Thr Met His Met Tyr Asp Ile Val Val Lys Asn Arg
                85                  90                  95

Asn Glu Phe Glu Ser Asn Gly Val Val Arg Leu Glu Asn Pro Ser Asp
            100                 105                 110

Tyr His Gly Ser Ala Gly Arg Arg Lys Val Leu Val His Ala Ala Ser
        115                 120                 125

Asn Glu Val Ile Thr Ser Tyr Ala Thr Leu Glu Arg Lys Leu Tyr Asn
    130                 135                 140

Leu Gly Trp Glu Arg Tyr Tyr Asp Asp Pro Glu Leu Leu Gln Tyr His
145                 150                 155                 160

Lys Arg Ser Thr Val His Leu Ile Ser Leu Pro Lys Asp Phe Ser Arg
                165                 170                 175

Phe Lys Ser Met His Met Tyr Asp Ile Val Val Lys Asn Arg Asn Glu
            180                 185                 190

Phe Glu Val Arg Asp Met
        195


<210> SEQ ID NO 59
<211> LENGTH: 197
<212> TYPE: PRT
<213> ORGANISM: Petunia inflata

<400> SEQUENCE: 59

Met Ser Gly Val Trp Val Phe Lys Asn Gly Val Leu Arg Leu Val Glu
1               5                   10                  15

Asn Pro Gly Asp Asn Tyr His Gly Ser Arg Lys Val Leu Val His Val
            20                  25                  30

Pro Ser Asn Glu Val Val Thr Ser Tyr Ala Ile Leu Glu Arg Lys Leu
        35                  40                  45

Tyr Asn Leu Gly Trp Glu Arg Tyr Tyr Asp Asp Pro Asn Leu Leu Gln
    50                  55                  60

Tyr His Lys Arg Ser Thr Val His Leu Ile Ser Leu Pro Arg Asp Phe
65                  70                  75                  80

Ser Lys Phe Lys Thr Met His Met Tyr Asp Ile Val Val Lys Asn Arg
                85                  90                  95

Asn Glu Phe Glu Ser Asn Gly Val Val Arg Leu Glu Asn Pro Gly Asp
            100                 105                 110

Tyr His Gly Ser Ser Gly Arg Arg Lys Val Leu Val His Ala Thr Ser
        115                 120                 125

Asn Glu Val Ile Thr Ser Tyr Ala Thr Leu Glu Arg Lys Leu Tyr Asn
    130                 135                 140

Leu Gly Trp Glu Arg Tyr Tyr Asp Asp Pro Glu Leu Leu Gln Tyr His
145                 150                 155                 160

Lys Arg Ser Thr Val His Leu Ile Ser Leu Pro Lys Asp Phe Ser Arg
                165                 170                 175

Phe Lys Ser Met His Met Tyr Asp Ile Val Val Lys Asn Arg Asn Glu
            180                 185                 190

Phe Glu Val Arg Asp
```

195

<210> SEQ ID NO 60
<211> LENGTH: 106
<212> TYPE: PRT
<213> ORGANISM: Capsicum annuum Zunla

<400> SEQUENCE: 60

Met Ser Gly Val Trp Val Phe Lys Asn Gly Val Val Arg Leu Val Glu
1               5                   10                  15

Asn Pro Gly Asp Cys His Gly Ala Thr Gly Arg Arg Lys Val Leu Val
            20                  25                  30

His Leu Ala Ser Asn Glu Val Ile Ser Ser Tyr Ala Ser Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Arg Phe Lys Ser Met His Met Tyr Asp Ile Val Val Lys
                85                  90                  95

Asn Arg Asn Glu Phe Glu Val Arg Asp Ile
            100                 105

<210> SEQ ID NO 61
<211> LENGTH: 106
<212> TYPE: PRT
<213> ORGANISM: Petunia axillaris

<400> SEQUENCE: 61

Met Ser Gly Val Trp Val Phe Lys Asn Gly Val Val Arg Leu Val Glu
1               5                   10                  15

Asn Pro Gly Asp Phe His Gly Ser Ser Gly Arg Arg Lys Val Leu Val
            20                  25                  30

His Val Pro Ser Asn Glu Val Ile Ser Ser Tyr Ala Thr Leu Glu Arg
        35                  40                  45

Lys Leu Ser Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Arg Phe Lys Ser Met His Met Tyr Asp Ile Val Val Lys
                85                  90                  95

Asn Arg Asn Glu Phe Glu Val Arg Asp Met
            100                 105

<210> SEQ ID NO 62
<211> LENGTH: 106
<212> TYPE: PRT
<213> ORGANISM: Petunia inflata

<400> SEQUENCE: 62

Met Ser Gly Val Trp Val Phe Lys Asn Gly Val Val Arg Leu Val Glu
1               5                   10                  15

Asn Pro Gly Asp Phe His Gly Ser Thr Gly Arg Arg Lys Val Leu Val
            20                  25                  30

His Val Pro Ser Asn Glu Val Ile Ser Ser Tyr Ala Thr Leu Glu Arg
        35                  40                  45

Lys Leu Ser Ser Leu Gly Trp Glu Arg Tyr Tyr Asp Asp Pro Asp Leu
    50                  55                  60

```
Leu Gln Tyr His Lys Arg Ser Thr Val His Leu Ile Ser Leu Pro Lys
65                  70                  75                  80

Asp Phe Asn Arg Phe Lys Ser Met His Met Tyr Asp Ile Val Val Lys
                85                  90                  95

Asn Arg Asn Glu Phe Glu Val Arg Asp Met
            100                 105


<210> SEQ ID NO 63
<211> LENGTH: 106
<212> TYPE: PRT
<213> ORGANISM: Solanum melongena

<400> SEQUENCE: 63

Met Ser Gly Val Trp Val Phe Lys Asn Gly Val Val Arg Leu Val Glu
1               5                   10                  15

Asn Pro Gly Asp Phe His Gly Ser Thr Gly Arg Arg Lys Val Leu Val
            20                  25                  30

His Leu Pro Ser Asn Glu Val Ile Thr Ser Tyr Ala Ala Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Arg Phe Lys Ser Met His Met Tyr Asp Ile Val Val Lys
                85                  90                  95

Asn Arg Asn Glu Phe Glu Val Arg Asp Met
            100                 105


<210> SEQ ID NO 64
<211> LENGTH: 106
<212> TYPE: PRT
<213> ORGANISM: Nicotiana benthamiana

<400> SEQUENCE: 64

Met Ser Gly Val Trp Val Phe Lys Asn Gly Val Val Arg Leu Val Glu
1               5                   10                  15

Asn Pro Gly Asp Cys His Gly Ala Thr Gly Arg Arg Lys Val Leu Val
            20                  25                  30

His Leu Ser Ser Asn Glu Val Ile Thr Ser Tyr Ser Ala Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Lys Phe Lys Ser Met His Met Tyr Asp Ile Val Val Lys
                85                  90                  95

Asn Arg Asn Glu Phe Glu Val Arg Asp Met
            100                 105


<210> SEQ ID NO 65
<211> LENGTH: 106
<212> TYPE: PRT
<213> ORGANISM: Nicotiana benthamiana

<400> SEQUENCE: 65

Met Ser Gly Val Trp Val Phe Lys Asn Gly Val Val Arg Leu Val Glu
1               5                   10                  15
```

```
Asn Pro Gly Asp Cys His Gly Ala Thr Gly Arg Arg Lys Val Leu Val
            20                  25                  30

His Leu Ser Ser Asn Glu Val Ile Thr Ser Tyr Ser Ala Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Lys
65                  70                  75                  80

Asp Phe Asn Arg Phe Lys Ser Met His Met Tyr Asp Ile Val Val Lys
                85                  90                  95

Asn Arg Asn Glu Phe Glu Val Arg Asp Met
            100                 105


<210> SEQ ID NO 66
<211> LENGTH: 106
<212> TYPE: PRT
<213> ORGANISM: Solanum lycopersicum

<400> SEQUENCE: 66

Met Ser Gly Val Trp Val Phe Lys Asn Gly Val Val Arg Leu Val Glu
1               5                   10                  15

Asn Pro Gly Asp Phe His Gly Ala Thr Gly Arg Arg Lys Val Leu Val
            20                  25                  30

His Leu Ser Ser Asn Glu Val Ile Thr Ser Tyr Ala Val Leu Glu Arg
        35                  40                  45

Lys Leu Tyr Ser Leu Gly Trp Glu Arg Tyr Tyr Asp Asp Pro Asp Leu
    50                  55                  60

Leu Gln Phe His Lys Arg Ser Thr Val His Leu Ile Ser Leu Pro Lys
65                  70                  75                  80

Asp Phe Asn Asn Leu Lys Ser Met His Met Tyr Asp Ile Val Val Lys
                85                  90                  95

Asn Arg Asn Glu Phe Thr Val Arg Asp Met
            100                 105


<210> SEQ ID NO 67
<211> LENGTH: 106
<212> TYPE: PRT
<213> ORGANISM: Solanum pennellii

<400> SEQUENCE: 67

Met Ser Gly Val Trp Val Phe Lys Asn Gly Val Val Arg Leu Val Glu
1               5                   10                  15

Asn Pro Gly Asp Phe His Gly Ala Thr Gly Arg Arg Lys Val Leu Val
            20                  25                  30

His Leu Ser Ser Asn Glu Val Ile Thr Ser Tyr Ala Ser Leu Glu Arg
        35                  40                  45

Ile Leu Phe Ser Leu Gly Trp Glu Arg Tyr Tyr Asp Asp Pro Asp Leu
    50                  55                  60

Leu Gln Phe His Lys Arg Ser Thr Ile His Leu Ile Ser Leu Pro Lys
65                  70                  75                  80

Asp Phe Asn Asn Phe Lys Ser Met His Met Tyr Asp Ile Val Val Lys
                85                  90                  95

Asn Arg Asn Glu Phe Thr Val Arg Asp Met
            100                 105


<210> SEQ ID NO 68
<211> LENGTH: 106
```

<212> TYPE: PRT
<213> ORGANISM: Solanum tuberosum

<400> SEQUENCE: 68

```
Met Ser Gly Val Trp Val Phe Lys Asn Gly Val Val Arg Leu Val Glu
1               5                   10                  15

Asn Ala Gly Asp Phe His Gly Ala Thr Gly Arg Arg Lys Val Leu Val
            20                  25                  30

His Leu Ser Ser Asn Glu Val Ile Thr Ser Tyr Ala Ser Leu Glu Arg
        35                  40                  45

Asn Leu Tyr Ser Leu Gly Trp Glu Arg Tyr Tyr Asp Asp Pro Asp Leu
    50                  55                  60

Leu Gln Phe His Lys Arg Ser Thr Val His Leu Ile Ser Leu Pro Lys
65                  70                  75                  80

Asp Phe Asn Arg Phe Lys Ser Met His Met Tyr Asp Ile Val Val Lys
                85                  90                  95

Asn Arg Asn Glu Phe Glu Val Arg Asp Met
            100                 105
```

<210> SEQ ID NO 69
<211> LENGTH: 106
<212> TYPE: PRT
<213> ORGANISM: Solanum pennellii

<400> SEQUENCE: 69

```
Met Ser Gly Val Trp Lys Ile Lys Asn Gly Val Val Arg Leu Val Glu
1               5                   10                  15

Asn Leu Gly Asp Phe Gln Gly Ala Thr Gly Arg Arg Lys Val Leu Val
            20                  25                  30

His Leu Ser Ser Asn Glu Val Ile Thr Ser Tyr Ala Ser Leu Glu Arg
        35                  40                  45

Ile Leu Tyr Ser Leu Gly Trp Glu Arg Tyr Tyr Asp Asp Pro Asn Leu
    50                  55                  60

Leu Gln Tyr His Lys Arg Ser Thr Val His Leu Ile Ser Leu Pro Lys
65                  70                  75                  80

Asp Phe Asn Asn Leu Lys Ser Met His Met Tyr Asp Ile Val Val Lys
                85                  90                  95

Asn Arg Asn Glu Phe Thr Val Arg Asp Met
            100                 105
```

<210> SEQ ID NO 70
<211> LENGTH: 106
<212> TYPE: PRT
<213> ORGANISM: Solanum lycopersicum

<400> SEQUENCE: 70

```
Met Ser Gly Val Trp Lys Ile Lys Asn Gly Val Val Arg Leu Val Glu
1               5                   10                  15

Asn Leu Gly Asp Phe His Gly Ala Thr Gly Arg Arg Lys Val Leu Val
            20                  25                  30

His Leu Ser Ser Asn Glu Val Ile Thr Ser Tyr Ala Val Leu Glu Arg
        35                  40                  45

Lys Leu Tyr Ser Leu Gly Trp Glu Arg Tyr Tyr Asp Asp Pro Asp Leu
    50                  55                  60

Leu Gln Tyr His Lys Arg Ser Thr Val His Leu Ile Ser Leu Pro Asn
65                  70                  75                  80

Asp Phe Asn Asn Leu Arg Ser Met His Met Tyr Asp Ile Val Val Lys
```

```
                85                  90                  95

Asn Arg Asn Glu Phe Ala Val Arg Asp Met
            100                 105


<210> SEQ ID NO 71
<211> LENGTH: 108
<212> TYPE: PRT
<213> ORGANISM: Capsicum annuum Zunla

<400> SEQUENCE: 71

Met Ser Gly Val Trp Thr Phe Lys Asn Gly Val Val Arg Leu Glu Asn
1               5                   10                  15

Arg Gly Asp Cys His Val Ser Ala Thr Thr Gly Arg Arg Lys Val Leu
            20                  25                  30

Val His Val Ala Ser Asp Glu Val Ile Thr Cys Tyr Glu Asn Leu Glu
        35                  40                  45

Arg Lys Leu Cys Asn Leu Gly Trp Glu Arg Phe Lys Ser Met His Met
    50                  55                  60

Tyr Asp Ile Val Val Lys Asn Arg Asn Glu Phe Glu Val Arg Asp Met
65                  70                  75                  80

Trp Ala Thr Arg Ser Thr Ala Leu Arg Cys Glu Val Gln Val Met Met
                85                  90                  95

Asp Gln Pro Glu Val Cys Ala Asp Ala Leu Asp Lys
            100                 105


<210> SEQ ID NO 72
<211> LENGTH: 86
<212> TYPE: PRT
<213> ORGANISM: Capsicum annuum

<400> SEQUENCE: 72

Val Ser Ala Thr Ala Gly Arg Arg Lys Val Leu Val His Val Ala Ser
1               5                   10                  15

Asp Glu Val Ile Thr Cys Tyr Glu Asn Leu Glu Arg Lys Leu Cys Asn
            20                  25                  30

Leu Gly Trp Glu Arg Tyr Tyr Asp Asp Pro Gln Leu Leu Gln Tyr His
        35                  40                  45

Lys Arg Ser Thr Ile His Leu Ile Ser Leu Pro Leu Asp Phe Thr Arg
    50                  55                  60

Phe Lys Ser Met His Met Tyr Asp Ile Val Val Lys Asn Arg Asn Glu
65                  70                  75                  80

Phe Glu Val Arg Asp Met
                85


<210> SEQ ID NO 73
<211> LENGTH: 107
<212> TYPE: PRT
<213> ORGANISM: Solanum melongena

<400> SEQUENCE: 73

Met Ser Gly Val Trp Val Phe Lys Asn Gly Val Val Arg Leu Glu Asn
1               5                   10                  15

Pro Gly Asp Cys His Val Ser Ser Thr Thr Ser Arg Arg Lys Val Leu
            20                  25                  30

Val His Val Pro Ser Asn Glu Val Ile Thr Cys Tyr Glu Asn Leu Glu
        35                  40                  45

Arg Lys Leu Tyr Ser Leu Gly Trp Glu Arg Tyr Tyr Asp Asp Pro Gln
    50                  55                  60
```

```
Leu Leu Gln Tyr His Lys Arg Ser Thr Ile His Leu Ile Ser Leu Pro
65                  70                  75                  80

Met Asp Phe Asn Arg Phe Lys Ser Met His Met Tyr Asp Ile Val Val
                85                  90                  95

Lys Asn Arg Asn Glu Phe Glu Val Arg Asp Met
            100                 105


<210> SEQ ID NO 74
<211> LENGTH: 107
<212> TYPE: PRT
<213> ORGANISM: Solanum lycopersicum

<400> SEQUENCE: 74

Met Ser Gly Val Trp Ile Phe Lys Asn Gly Val Val Arg Leu Glu Thr
1               5                   10                  15

Pro Gly Asp Cys His Val Ser Ser Thr Thr Gly His Arg Lys Val Leu
            20                  25                  30

Val His Val Pro Ser Lys Glu Val Ile Thr Cys Tyr Ala Asn Leu Glu
        35                  40                  45

Lys Lys Leu Tyr Ser Leu Gly Trp Glu Arg Tyr Tyr Asp Asp Pro Gln
    50                  55                  60

Leu Leu Gln Tyr His Lys Arg Ser Thr Ile His Leu Ile Ser Leu Pro
65                  70                  75                  80

Ile Asp Phe Asn Arg Phe Lys Ser Ile His Met Tyr Asp Ile Val Val
                85                  90                  95

Lys Asn Arg Asn Glu Phe Glu Val Arg Asp Met
            100                 105


<210> SEQ ID NO 75
<211> LENGTH: 107
<212> TYPE: PRT
<213> ORGANISM: Solanum tuberosum

<400> SEQUENCE: 75

Met Ser Gly Val Trp Ile Phe Lys Asn Gly Val Val Arg Leu Glu Asn
1               5                   10                  15

Pro Gly Asp Cys His Val Ser Ser Thr Thr Gly His Arg Lys Val Leu
            20                  25                  30

Val His Val Pro Ser Asn Glu Val Ile Thr Cys Tyr Ala Asn Leu Glu
        35                  40                  45

Arg Lys Leu Tyr Ser Leu Gly Trp Glu Arg Tyr Tyr Asp Asp Pro Gln
    50                  55                  60

Leu Leu Gln Tyr His Lys Arg Ser Thr Ile His Leu Ile Ser Leu Pro
65                  70                  75                  80

Ile Asp Phe Asn Arg Phe Lys Ser Ile His Met Tyr Asp Ile Val Val
                85                  90                  95

Lys Asn Arg Asn Glu Phe Glu Val Arg Asp Met
            100                 105


<210> SEQ ID NO 76
<211> LENGTH: 20
<212> TYPE: DNA
<213> ORGANISM: Artificial Sequence
<220> FEATURE:
<223> OTHER INFORMATION: gRNA sequence

<400> SEQUENCE: 76

gagaagagac tcattgaaat                                                 20
```

<210> SEQ ID NO 77
<211> LENGTH: 20
<212> TYPE: DNA
<213> ORGANISM: Artificial Sequence
<220> FEATURE:
<223> OTHER INFORMATION: gRNA sequence

<400> SEQUENCE: 77
gggggcacgc cctcgagtgt 20

<210> SEQ ID NO 78
<211> LENGTH: 20
<212> TYPE: DNA
<213> ORGANISM: Artificial Sequence
<220> FEATURE:
<223> OTHER INFORMATION: gRNA sequence

<400> SEQUENCE: 78
ggtaggtaca ccaacactcg 20

<210> SEQ ID NO 79
<211> LENGTH: 20
<212> TYPE: DNA
<213> ORGANISM: Artificial Sequence
<220> FEATURE:
<223> OTHER INFORMATION: gRNA sequence

<400> SEQUENCE: 79
aacactcgag ggcgtgcccc 20

<210> SEQ ID NO 80
<211> LENGTH: 20
<212> TYPE: DNA
<213> ORGANISM: Artificial Sequence
<220> FEATURE:
<223> OTHER INFORMATION: gRNA sequence

<400> SEQUENCE: 80
gggtacagcc acagcaccgg 20

<210> SEQ ID NO 81
<211> LENGTH: 20
<212> TYPE: DNA
<213> ORGANISM: Artificial Sequence
<220> FEATURE:
<223> OTHER INFORMATION: gRNA sequence

<400> SEQUENCE: 81
cgggtacagc cacagcaccg 20

<210> SEQ ID NO 82
<211> LENGTH: 20
<212> TYPE: DNA
<213> ORGANISM: Artificial Sequence
<220> FEATURE:
<223> OTHER INFORMATION: gRNA sequence

<400> SEQUENCE: 82
acgggtacag ccacagcacc 20

<210> SEQ ID NO 83
<211> LENGTH: 20
<212> TYPE: DNA
<213> ORGANISM: Artificial Sequence
<220> FEATURE:

<223> OTHER INFORMATION: gRNA sequence

<400> SEQUENCE: 83
cacgggtaca gccacagcac 20

<210> SEQ ID NO 84
<211> LENGTH: 20
<212> TYPE: DNA
<213> ORGANISM: Artificial Sequence
<220> FEATURE:
<223> OTHER INFORMATION: gRNA sequence

<400> SEQUENCE: 84
agggcgtgcc cccggtgctg 20

<210> SEQ ID NO 85
<211> LENGTH: 20
<212> TYPE: DNA
<213> ORGANISM: Artificial Sequence
<220> FEATURE:
<223> OTHER INFORMATION: gRNA sequence

<400> SEQUENCE: 85
tgtattcgtc cttgtaggca 20

<210> SEQ ID NO 86
<211> LENGTH: 20
<212> TYPE: DNA
<213> ORGANISM: Artificial Sequence
<220> FEATURE:
<223> OTHER INFORMATION: gRNA sequence

<400> SEQUENCE: 86
aattctgtat tcgtccttgt 20

<210> SEQ ID NO 87
<211> LENGTH: 20
<212> TYPE: DNA
<213> ORGANISM: Artificial Sequence
<220> FEATURE:
<223> OTHER INFORMATION: gRNA sequence

<400> SEQUENCE: 87
tggctgtacc cgtgcctaca 20

<210> SEQ ID NO 88
<211> LENGTH: 20
<212> TYPE: DNA
<213> ORGANISM: Artificial Sequence
<220> FEATURE:
<223> OTHER INFORMATION: gRNA sequence

<400> SEQUENCE: 88
acgagtacaa aatgtcatga 20

<210> SEQ ID NO 89
<211> LENGTH: 20
<212> TYPE: DNA
<213> ORGANISM: Artificial Sequence
<220> FEATURE:
<223> OTHER INFORMATION: gRNA sequence

<400> SEQUENCE: 89
acaacataag ctttaagtca 20

<210> SEQ ID NO 90
<211> LENGTH: 20
<212> TYPE: DNA
<213> ORGANISM: Artificial Sequence
<220> FEATURE:
<223> OTHER INFORMATION: gRNA sequence

<400> SEQUENCE: 90
ttgtaattat gggtgcaact 20

<210> SEQ ID NO 91
<211> LENGTH: 20
<212> TYPE: DNA
<213> ORGANISM: Artificial Sequence
<220> FEATURE:
<223> OTHER INFORMATION: gRNA sequence

<400> SEQUENCE: 91
agtaggattt ttgatcaaat 20

<210> SEQ ID NO 92
<211> LENGTH: 20
<212> TYPE: DNA
<213> ORGANISM: Artificial Sequence
<220> FEATURE:
<223> OTHER INFORMATION: gRNA sequence

<400> SEQUENCE: 92
aaccattata ttataatgtc 20

<210> SEQ ID NO 93
<211> LENGTH: 20
<212> TYPE: DNA
<213> ORGANISM: Artificial Sequence
<220> FEATURE:
<223> OTHER INFORMATION: gRNA sequence

<400> SEQUENCE: 93
agtcaccggg ggtttctagc 20

<210> SEQ ID NO 94
<211> LENGTH: 20
<212> TYPE: DNA
<213> ORGANISM: Artificial Sequence
<220> FEATURE:
<223> OTHER INFORMATION: gRNA sequence

<400> SEQUENCE: 94
gtcgtccggc tagaaacccc 20

<210> SEQ ID NO 95
<211> LENGTH: 20
<212> TYPE: DNA
<213> ORGANISM: Artificial Sequence
<220> FEATURE:
<223> OTHER INFORMATION: gRNA sequence

<400> SEQUENCE: 95
agctgacgtg gcagtcaccg 20

<210> SEQ ID NO 96
<211> LENGTH: 20
<212> TYPE: DNA
<213> ORGANISM: Artificial Sequence
<220> FEATURE:
<223> OTHER INFORMATION: gRNA sequence

<400> SEQUENCE: 96
gagctgacgt ggcagtcacc 20

<210> SEQ ID NO 97
<211> LENGTH: 20
<212> TYPE: DNA
<213> ORGANISM: Artificial Sequence
<220> FEATURE:
<223> OTHER INFORMATION: gRNA sequence

<400> SEQUENCE: 97
gaccggtcgt ggagctgacg 20

<210> SEQ ID NO 98
<211> LENGTH: 20
<212> TYPE: DNA
<213> ORGANISM: Artificial Sequence
<220> FEATURE:
<223> OTHER INFORMATION: gRNA sequence

<400> SEQUENCE: 98
aactttccga tgaccggtcg 20

<210> SEQ ID NO 99
<211> LENGTH: 20
<212> TYPE: DNA
<213> ORGANISM: Artificial Sequence
<220> FEATURE:
<223> OTHER INFORMATION: gRNA sequence

<400> SEQUENCE: 99
gatgaattgt ggatcttttg 20

<210> SEQ ID NO 100
<211> LENGTH: 20
<212> TYPE: DNA
<213> ORGANISM: Artificial Sequence
<220> FEATURE:
<223> OTHER INFORMATION: gRNA sequence

<400> SEQUENCE: 100
gagggaaata agatgaattg 20

<210> SEQ ID NO 101
<211> LENGTH: 20
<212> TYPE: DNA
<213> ORGANISM: Artificial Sequence
<220> FEATURE:
<223> OTHER INFORMATION: gRNA sequence

<400> SEQUENCE: 101
ccctcccaat tgattttaat 20

<210> SEQ ID NO 102
<211> LENGTH: 632
<212> TYPE: DNA
<213> ORGANISM: Solanum lycopersicum

<400> SEQUENCE: 102
catctcatca taaactacaa acacatacaa aaaacattct cattcacctt tcctctacaa 60
aaaacataac aacatcttca acaatcatgt ctggagtttg ggtattcaag aatggtgttg 120
tccgtctagt ggagaactcc gattgccacg gggcgaacgg actccgaaaa gttcttgtac 180
atcttcctag taatgaagtc atcacatcat atgcagtact tgaaaggaaa ctgtactctc 240
ttggatggga gaggtactat gatgaacctg aacttcttca ataccacaaa agatcaaccg 300
ttcatcttat ttctctacca aaggatttca acaggttcaa atccatgcat atgttcgata 360
tcgtcgtcaa gaatcgcaat gaatttgagg ttagagatat gtaaacaaaa tatgggggaa 420
aaaagggaag gagttgatca tttgaatgtg ttttttttc tttttttgc ttttttttgg 480 tcaagtgtgt tgtaattaag tttctatcgt ttaatttgtg atttgtttca caatgttgct 540
aaggttgtaa tttggaaagt tgtaagaggg gaaatgttgt atattattac aagtgaatgt 600
gttttattat atgatatata tatatataag ag 632

<210> SEQ ID NO 103
<211> LENGTH: 19
<212> TYPE: DNA
<213> ORGANISM: Artificial Sequence
<220> FEATURE:
<223> OTHER INFORMATION: gRNA sequence

<400> SEQUENCE: 103
tctagtggag aactccgat 19

<210> SEQ ID NO 104
<211> LENGTH: 20
<212> TYPE: DNA
<213> ORGANISM: Artificial Sequence
<220> FEATURE:
<223> OTHER INFORMATION: gRNA sequence

<400> SEQUENCE: 104
aaaagttctt gtacatcttc 20

<210> SEQ ID NO 105
<211> LENGTH: 20
<212> TYPE: DNA
<213> ORGANISM: Solanum lycopersicum

<400> SEQUENCE: 105
tcgcaccgtg aaagtcaccg 20

<210> SEQ ID NO 106
<211> LENGTH: 20
<212> TYPE: DNA
<213> ORGANISM: Solanum lycopersicum

<400> SEQUENCE: 106
tcgcaccgtg gaagtcaccg 20

<210> SEQ ID NO 107
<211> LENGTH: 26
<212> TYPE: DNA
<213> ORGANISM: Solanum lycopersicum

<400> SEQUENCE: 107
ccgtcgcacc gtgaaagtca ccgagg 26

<210> SEQ ID NO 108
<211> LENGTH: 26
<212> TYPE: DNA
<213> ORGANISM: Solanum lycopersicum

<400> SEQUENCE: 108
ccgtcgcacc gtggaagtca ccgggg 26

```
<210> SEQ ID NO 109
<211> LENGTH: 26
<212> TYPE: DNA
<213> ORGANISM: Artificial Sequence
<220> FEATURE:
<223> OTHER INFORMATION: mutant brachytic locus sequence

<400> SEQUENCE: 109

ccgtcgcacc gtgaaagtca ccgagg                                          26


<210> SEQ ID NO 110
<211> LENGTH: 27
<212> TYPE: DNA
<213> ORGANISM: Artificial Sequence
<220> FEATURE:
<223> OTHER INFORMATION: mutant brachytic locus sequence

<400> SEQUENCE: 110

ccgtcgcaac cgtggaagtc accgggg                                         27


<210> SEQ ID NO 111
<211> LENGTH: 21
<212> TYPE: DNA
<213> ORGANISM: Artificial Sequence
<220> FEATURE:
<223> OTHER INFORMATION: mutant brachytic locus sequence

<400> SEQUENCE: 111

ccgtcgcacc gtgaaccgag g                                               21


<210> SEQ ID NO 112
<211> LENGTH: 21
<212> TYPE: DNA
<213> ORGANISM: Artificial Sequence
<220> FEATURE:
<223> OTHER INFORMATION: mutant brachytic locus sequence

<400> SEQUENCE: 112

ccgtcgcacc gtggaccggg g                                               21


<210> SEQ ID NO 113
<211> LENGTH: 27
<212> TYPE: DNA
<213> ORGANISM: Artificial Sequence
<220> FEATURE:
<223> OTHER INFORMATION: mutant brachytic locus sequence

<400> SEQUENCE: 113

ccgtcgcacc gtgaaagtca accgagg                                         27


<210> SEQ ID NO 114
<211> LENGTH: 21
<212> TYPE: DNA
<213> ORGANISM: Artificial Sequence
<220> FEATURE:
<223> OTHER INFORMATION: mutant brachytic locus sequence

<400> SEQUENCE: 114

ccgtcgcacc gtggaccggg g                                               21


<210> SEQ ID NO 115
<211> LENGTH: 19
<212> TYPE: DNA
<213> ORGANISM: Artificial Sequence
<220> FEATURE:
<223> OTHER INFORMATION: gRNA sequence
```

<400> SEQUENCE: 115
atcggagttc tccactaga 19

<210> SEQ ID NO 116
<211> LENGTH: 20
<212> TYPE: DNA
<213> ORGANISM: Artificial Sequence
<220> FEATURE:
<223> OTHER INFORMATION: gRNA sequence

<400> SEQUENCE: 116
gaagatgtac aagaactttt 20

<210> SEQ ID NO 117
<211> LENGTH: 20
<212> TYPE: DNA
<213> ORGANISM: Artificial Sequence
<220> FEATURE:
<223> OTHER INFORMATION: gRNA sequence

<400> SEQUENCE: 117
tcgcaccgtg aaagtcaccg 20

<210> SEQ ID NO 118
<211> LENGTH: 22
<212> TYPE: DNA
<213> ORGANISM: Artificial Sequence
<220> FEATURE:
<223> OTHER INFORMATION: primer

<400> SEQUENCE: 118
ttcccctctt acaactttcc aa 22

<210> SEQ ID NO 119
<211> LENGTH: 20
<212> TYPE: DNA
<213> ORGANISM: Artificial Sequence
<220> FEATURE:
<223> OTHER INFORMATION: primer

<400> SEQUENCE: 119
ccagaaacgg gggagactac 20

<210> SEQ ID NO 120
<211> LENGTH: 22
<212> TYPE: DNA
<213> ORGANISM: Artificial Sequence
<220> FEATURE:
<223> OTHER INFORMATION: primer

<400> SEQUENCE: 120
catgtgcatg gacttgaggt tg 22

<210> SEQ ID NO 121
<211> LENGTH: 21
<212> TYPE: DNA
<213> ORGANISM: Artificial Sequence
<220> FEATURE:
<223> OTHER INFORMATION: primer

<400> SEQUENCE: 121
agggctgatc aagcaatgga t 21

<210> SEQ ID NO 122

<211> LENGTH: 22
<212> TYPE: DNA
<213> ORGANISM: Artificial Sequence
<220> FEATURE:
<223> OTHER INFORMATION: primer

<400> SEQUENCE: 122
gacctgaggt tgttgaagtc gt 22

<210> SEQ ID NO 123
<211> LENGTH: 21
<212> TYPE: DNA
<213> ORGANISM: Artificial Sequence
<220> FEATURE:
<223> OTHER INFORMATION: primer

<400> SEQUENCE: 123
ttttgggtcg tgacaggtaa a 21

<210> SEQ ID NO 124
<211> LENGTH: 20
<212> TYPE: DNA
<213> ORGANISM: Artificial Sequence
<220> FEATURE:
<223> OTHER INFORMATION: primer

<400> SEQUENCE: 124
ccagattcat ctcggggagc 20

<210> SEQ ID NO 125
<211> LENGTH: 20
<212> TYPE: DNA
<213> ORGANISM: Artificial Sequence
<220> FEATURE:
<223> OTHER INFORMATION: primer

<400> SEQUENCE: 125
gagctgctta accgtgacct 20

<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
ggacttcctg gacaacgagg 20

<210> SEQ ID NO 127
<211> LENGTH: 20
<212> TYPE: DNA
<213> ORGANISM: Artificial Sequence
<220> FEATURE:
<223> OTHER INFORMATION: primer

<400> SEQUENCE: 127
cgtgagttct tctggccctt 20

<210> SEQ ID NO 128
<211> LENGTH: 20
<212> TYPE: DNA
<213> ORGANISM: Artificial Sequence
<220> FEATURE:
<223> OTHER INFORMATION: primer

<400> SEQUENCE: 128

-continued gagggcgtgg atatgtcctg 20

<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
ggcgacctcg tattgggaat 20

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
gctctcgatg agctgatgct 20

<210> SEQ ID NO 131
<211> LENGTH: 20
<212> TYPE: DNA
<213> ORGANISM: Artificial Sequence
<220> FEATURE:
<223> OTHER INFORMATION: primer

<400> SEQUENCE: 131
atttgtgtac gcccgacagt 20

<210> SEQ ID NO 132
<211> LENGTH: 23
<212> TYPE: DNA
<213> ORGANISM: Artificial Sequence
<220> FEATURE:
<223> OTHER INFORMATION: off-target site

<400> SEQUENCE: 132
gaacgtagtt gaccactaga tgg 23

<210> SEQ ID NO 133
<211> LENGTH: 23
<212> TYPE: DNA
<213> ORGANISM: Artificial Sequence
<220> FEATURE:
<223> OTHER INFORMATION: off-target site

<400> SEQUENCE: 133
gattgaagtt ctccgttaga tgg 23

<210> SEQ ID NO 134
<211> LENGTH: 23
<212> TYPE: DNA
<213> ORGANISM: Artificial Sequence
<220> FEATURE:
<223> OTHER INFORMATION: off-target site

<400> SEQUENCE: 134
caatggagtt cttcactaga ggg 23

<210> SEQ ID NO 135
<211> LENGTH: 23
<212> TYPE: DNA

<213> ORGANISM: Artificial Sequence
<220> FEATURE:
<223> OTHER INFORMATION: off-target site

<400> SEQUENCE: 135
gatgagagtt ctgcacttga tgg 23

<210> SEQ ID NO 136
<211> LENGTH: 24
<212> TYPE: DNA
<213> ORGANISM: Artificial Sequence
<220> FEATURE:
<223> OTHER INFORMATION: off-target site

<400> SEQUENCE: 136
ttatgatgta caaaaacttt tagg 24

<210> SEQ ID NO 137
<211> LENGTH: 24
<212> TYPE: DNA
<213> ORGANISM: Artificial Sequence
<220> FEATURE:
<223> OTHER INFORMATION: off-target site

<400> SEQUENCE: 137
ggaagatgta ccaatacgtt tcgg 24

<210> SEQ ID NO 138
<211> LENGTH: 24
<212> TYPE: DNA
<213> ORGANISM: Artificial Sequence
<220> FEATURE:
<223> OTHER INFORMATION: off-target site

<400> SEQUENCE: 138
ttaagattta caacaacttt ttgg 24

<210> SEQ ID NO 139
<211> LENGTH: 24
<212> TYPE: DNA
<213> ORGANISM: Artificial Sequence
<220> FEATURE:
<223> OTHER INFORMATION: off-target site

<400> SEQUENCE: 139
ggaagatgtc ctagttcttt ttgg 24

<210> SEQ ID NO 140
<211> LENGTH: 24
<212> TYPE: DNA
<213> ORGANISM: Artificial Sequence
<220> FEATURE:
<223> OTHER INFORMATION: off-target site

<400> SEQUENCE: 140
ggaacatgta caagaagctt gagg 24

<210> SEQ ID NO 141
<211> LENGTH: 24
<212> TYPE: DNA
<213> ORGANISM: Artificial Sequence
<220> FEATURE:
<223> OTHER INFORMATION: off-target site

<400> SEQUENCE: 141
ggaagacgtt caagaatttt tcgg 24

-continued

<210> SEQ ID NO 142
<211> LENGTH: 24
<212> TYPE: DNA
<213> ORGANISM: Artificial Sequence
<220> FEATURE:
<223> OTHER INFORMATION: off-target site

<400> SEQUENCE: 142
ggaagatgaa taataactat ttgg 24

<210> SEQ ID NO 143
<211> LENGTH: 24
<212> TYPE: DNA
<213> ORGANISM: Artificial Sequence
<220> FEATURE:
<223> OTHER INFORMATION: off-target site

<400> SEQUENCE: 143
aacagaagta caagaacttt tggg 24

<210> SEQ ID NO 144
<211> LENGTH: 24
<212> TYPE: DNA
<213> ORGANISM: Artificial Sequence
<220> FEATURE:
<223> OTHER INFORMATION: off-target site

<400> SEQUENCE: 144
agcagatgta caagatcttt aagg 24

<210> SEQ ID NO 145
<211> LENGTH: 24
<212> TYPE: DNA
<213> ORGANISM: Artificial Sequence
<220> FEATURE:
<223> OTHER INFORMATION: off-target site

<400> SEQUENCE: 145
agaagctgta tatgaacttt tggg 24

<210> SEQ ID NO 146
<211> LENGTH: 24
<212> TYPE: DNA
<213> ORGANISM: Artificial Sequence
<220> FEATURE:
<223> OTHER INFORMATION: off-target site

<400> SEQUENCE: 146
ggaagaagaa gaagaagttt tagg 24

<210> SEQ ID NO 147
<211> LENGTH: 24
<212> TYPE: DNA
<213> ORGANISM: Artificial Sequence
<220> FEATURE:
<223> OTHER INFORMATION: off-target site

<400> SEQUENCE: 147
tgatgatgta aaagaacttt ttgg 24

<210> SEQ ID NO 148
<211> LENGTH: 24
<212> TYPE: DNA
<213> ORGANISM: Artificial Sequence
<220> FEATURE:

<223> OTHER INFORMATION: off-target site

<400> SEQUENCE: 148
ggaagatgga caacaagatt tagg 24

<210> SEQ ID NO 149
<211> LENGTH: 24
<212> TYPE: DNA
<213> ORGANISM: Artificial Sequence
<220> FEATURE:
<223> OTHER INFORMATION: off-target site

<400> SEQUENCE: 149
tgaagaagca caagagcttt ttgg 24

<210> SEQ ID NO 150
<211> LENGTH: 24
<212> TYPE: DNA
<213> ORGANISM: Artificial Sequence
<220> FEATURE:
<223> OTHER INFORMATION: off-target site

<400> SEQUENCE: 150
ggatgatata caagcatttt tagg 24

<210> SEQ ID NO 151
<211> LENGTH: 24
<212> TYPE: DNA
<213> ORGANISM: Artificial Sequence
<220> FEATURE:
<223> OTHER INFORMATION: off-target site

<400> SEQUENCE: 151
ggaagatgta ccataacttt aggg 24

<210> SEQ ID NO 152
<211> LENGTH: 24
<212> TYPE: DNA
<213> ORGANISM: Artificial Sequence
<220> FEATURE:
<223> OTHER INFORMATION: off-target site

<400> SEQUENCE: 152
gcaagatgca caagaccctt tggg 24

<210> SEQ ID NO 153
<211> LENGTH: 24
<212> TYPE: DNA
<213> ORGANISM: Artificial Sequence
<220> FEATURE:
<223> OTHER INFORMATION: off-target site

<400> SEQUENCE: 153
gcaagatcta caagaacttc acgg 24

<210> SEQ ID NO 154
<211> LENGTH: 24
<212> TYPE: DNA
<213> ORGANISM: Artificial Sequence
<220> FEATURE:
<223> OTHER INFORMATION: off-target site

<400> SEQUENCE: 154
ggaagatatt caataaattt tagg 24

-continued

```
<210> SEQ ID NO 155
<211> LENGTH: 24
<212> TYPE: DNA
<213> ORGANISM: Artificial Sequence
<220> FEATURE:
<223> OTHER INFORMATION: off-target site

<400> SEQUENCE: 155

ggaagatatg aaagaacttt atgg                                    24
```